(12) United States Patent
Miles et al.

(10) Patent No.: US 8,303,515 B2
(45) Date of Patent: *Nov. 6, 2012

(54) SURGICAL ACCESS SYSTEM AND RELATED METHODS

(75) Inventors: Patrick Miles, San Diego, CA (US); Scot Martinelli, Mountain Top, PA (US); Eric Finley, Poway, CA (US); Luiz Pimenta, Sao Paulo (BR)

(73) Assignee: NuVasive, Inc., San Diego, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 12/635,869

(22) Filed: Dec. 11, 2009

(65) Prior Publication Data

US 2010/0130827 A1  May 27, 2010

Related U.S. Application Data

(63) Continuation of application No. 10/967,668, filed on Oct. 18, 2004, now Pat. No. 7,905,840, which is a continuation-in-part of application No. PCT/US2004/031768, filed on Sep. 27, 2004.

(60) Provisional application No. 60/512,594, filed on Oct. 17, 2003, provisional application No. 60/506,136, filed on Sep. 25, 2003.

(51) Int. Cl.
*A61B 5/05* (2006.01)

(52) U.S. Cl. ............................................. 600/554

(58) Field of Classification Search .................. 600/554, 600/546, 547; 606/108, 86 A, 279
See application file for complete search history.

(56) References Cited

U.S. PATENT DOCUMENTS

| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |

(Continued)

FOREIGN PATENT DOCUMENTS

DE    299 08 259    7/1999

(Continued)

OTHER PUBLICATIONS

Bergey et al., "Endoscopic Lateral Transpsoas Approach to the Lumbar Spine," *Spine*, 2004, 29(15): 1681-1688.

(Continued)

*Primary Examiner* — Jeffrey G Hoekstra
*Assistant Examiner* — Fangemonique Smith
(74) *Attorney, Agent, or Firm* — Fish & Richardson P.C.

(57) ABSTRACT

A surgical access system including a tissue distraction assembly and a tissue retraction assembly, both of which may be equipped with one or more electrodes for use in detecting the existence of (and optionally the distance and/or direction to) neural structures before, during, and after the establishment of an operative corridor to a surgical target site. Some embodiments of the surgical access system may be particularly suited for establishing an operative corridor to a surgical target site in the spine. Such an operative corridor may be established through the retroperitoneal space and the psoas muscle during a direct lateral, retroperitoneal approach to the spine.

36 Claims, 50 Drawing Sheets

U.S. PATENT DOCUMENTS

| | | | |
|---|---|---|---|
| 3,785,368 A | 1/1974 | McCarthy et al. | |
| 3,830,226 A | 8/1974 | Staub et al. | |
| 3,957,036 A | 5/1976 | Normann | |
| 4,099,519 A | 7/1978 | Warren | |
| 4,164,214 A | 8/1979 | Stark et al. | |
| 4,207,897 A | 6/1980 | Lloyd et al. | |
| 4,224,949 A | 9/1980 | Scott et al. | |
| 4,226,228 A | 10/1980 | Shin et al. | |
| 4,235,242 A | 11/1980 | Howson et al. | |
| 4,285,347 A | 8/1981 | Hess | |
| 4,291,705 A | 9/1981 | Severinghaus et al. | |
| 4,461,300 A | 7/1984 | Christensen | |
| 4,515,168 A | 5/1985 | Chester et al. | |
| 4,519,403 A | 5/1985 | Dickhudt | |
| 4,545,374 A | 10/1985 | Jacobson | |
| 4,561,445 A | 12/1985 | Berke et al. | |
| 4,562,832 A | 1/1986 | Wilder et al. | |
| 4,573,448 A | 3/1986 | Kambin | |
| 4,592,369 A | 6/1986 | Davis et al. | |
| 4,595,018 A | 6/1986 | Rantala | |
| 4,611,597 A | 9/1986 | Kraus | |
| 4,633,889 A | 1/1987 | Talalla | |
| 4,658,835 A | 4/1987 | Pohndorf | |
| 4,744,371 A | 5/1988 | Harris | |
| 4,759,377 A | 7/1988 | Dykstra | |
| 4,784,150 A | 11/1988 | Voorhies et al. | |
| 4,807,642 A | 2/1989 | Brown | |
| 4,892,105 A | 1/1990 | Prass | |
| 4,913,134 A | 4/1990 | Luque | |
| 4,926,865 A | 5/1990 | Oman | |
| 4,962,766 A | 10/1990 | Herzon | |
| 4,964,411 A | 10/1990 | Johnson et al. | |
| 5,007,902 A | 4/1991 | Witt | |
| 5,052,373 A | 10/1991 | Michelson | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,171,279 A | 12/1992 | Mathews | |
| 5,195,541 A | 3/1993 | Obenchain | |
| 5,196,015 A | 3/1993 | Neubardt | |
| RE34,390 E | 9/1993 | Culver | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,295,994 A | 3/1994 | Bonutti | |
| 5,299,563 A | 4/1994 | Seton | |
| 5,312,417 A | 5/1994 | Wilk | |
| 5,313,956 A | 5/1994 | Knutsson et al. | |
| 5,313,962 A | 5/1994 | Obenchain | |
| 5,327,902 A | 7/1994 | Lemmen | |
| 5,331,975 A | 7/1994 | Bonutti | |
| 5,333,618 A | 8/1994 | Lekhtman et al. | |
| 5,342,384 A | 8/1994 | Sugarbaker | |
| 5,375,067 A | 12/1994 | Berchin | |
| 5,375,594 A | 12/1994 | Cueva | |
| 5,383,876 A | 1/1995 | Nardella | |
| 5,395,317 A | 3/1995 | Kambin | |
| 5,450,845 A | 9/1995 | Alexgaard | |
| 5,474,057 A | 12/1995 | Makower et al. | |
| 5,474,558 A | 12/1995 | Neubardt | |
| 5,480,440 A | 1/1996 | Kambin | |
| 5,482,038 A | 1/1996 | Ruff | |
| 5,484,437 A | 1/1996 | Michelson | |
| 5,509,893 A | 4/1996 | Pracas | |
| 5,514,153 A | 5/1996 | Bonutti | |
| 5,540,235 A | 7/1996 | Wilson | |
| 5,549,656 A | 8/1996 | Reiss | |
| 5,560,372 A | 10/1996 | Cory | |
| 5,566,678 A | 10/1996 | Cadwell | |
| 5,571,149 A | 11/1996 | Liss et al. | |
| 5,579,781 A | 12/1996 | Cooke | |
| 5,593,429 A | 1/1997 | Ruff | |
| 5,599,279 A | 2/1997 | Slotman et al. | |
| 5,630,813 A | 5/1997 | Kieturakis | |
| 5,667,508 A | 9/1997 | Errico et al. | |
| 5,671,752 A | 9/1997 | Sinderby et al. | |
| 5,681,265 A | 10/1997 | Maeda et al. | |
| 5,707,359 A | 1/1998 | Bufalini | |
| 5,711,307 A | 1/1998 | Smits | |
| 5,728,046 A | 3/1998 | Mayer et al. | |
| 5,741,253 A | 4/1998 | Michelson | |
| 5,759,159 A | 6/1998 | Masreliez | |
| 5,762,629 A | 6/1998 | Kambin | |
| 5,772,661 A | 6/1998 | Michelson | |
| 5,775,331 A | 7/1998 | Raymond et al. | |
| 5,776,144 A | 7/1998 | Leysieffer et al. | |
| 5,779,642 A | 7/1998 | Nightengale | |
| 5,785,658 A | 7/1998 | Benaron | |
| 5,792,044 A | 8/1998 | Foley et al. | |
| 5,797,854 A | 8/1998 | Hedgecock | |
| 5,814,073 A | 9/1998 | Bonutti | |
| 5,830,151 A | 11/1998 | Hadzic et al. | |
| 5,851,191 A | 12/1998 | Gozani | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,210 A | 3/1999 | Cox | |
| 5,885,219 A | 3/1999 | Nightengale | |
| 5,888,196 A | 3/1999 | Bonutti | |
| 5,891,147 A | 4/1999 | Moskovitz et al. | |
| 5,902,231 A | 5/1999 | Foley et al. | |
| 5,928,139 A | 7/1999 | Koros et al. | |
| 5,928,158 A | 7/1999 | Aristides | |
| 5,931,777 A | 8/1999 | Sava | |
| 5,935,131 A | 8/1999 | Bonutti et al. | |
| 5,938,688 A | 8/1999 | Schiff | |
| 5,944,658 A | 8/1999 | Koros et al. | |
| 5,976,094 A | 11/1999 | Gozani et al. | |
| 6,004,262 A | 12/1999 | Putz et al. | |
| 6,004,312 A | 12/1999 | Finneran | |
| 6,007,487 A | 12/1999 | Foley et al. | |
| 6,024,696 A | 2/2000 | Hoftman et al. | |
| 6,027,456 A | 2/2000 | Feler et al. | |
| 6,038,469 A | 3/2000 | Karlsson et al. | |
| 6,038,477 A | 3/2000 | Kayyali | |
| 6,050,992 A | 4/2000 | Nichols | |
| 6,074,343 A | 6/2000 | Nathanson et al. | |
| 6,083,154 A | 7/2000 | Liu et al. | |
| 6,095,987 A | 8/2000 | Schmulewitz | |
| 6,104,957 A | 8/2000 | Alo et al. | |
| 6,104,960 A | 8/2000 | Duysens et al. | |
| 6,120,503 A | 9/2000 | Michelson | |
| 6,126,660 A | 10/2000 | Dietz | |
| 6,132,386 A | 10/2000 | Gozani et al. | |
| 6,132,387 A | 10/2000 | Gozani et al. | |
| 6,135,965 A | 10/2000 | Tumer et al. | |
| 6,139,493 A | 10/2000 | Koros et al. | |
| 6,146,335 A | 11/2000 | Gozani | |
| 6,152,871 A | 11/2000 | Foley et al. | |
| 6,161,047 A | 12/2000 | King et al. | |
| 6,174,311 B1 | 1/2001 | Branch et al. | |
| 6,181,961 B1 | 1/2001 | Prass | |
| 6,196,969 B1 | 3/2001 | Bester et al. | |
| 6,206,826 B1 | 3/2001 | Mathews et al. | |
| 6,217,509 B1 | 4/2001 | Foley et al. | |
| 6,224,549 B1 | 5/2001 | Drongelen | |
| 6,259,945 B1 | 7/2001 | Epstein et al. | |
| 6,264,651 B1 | 7/2001 | Underwood et al. | |
| 6,266,558 B1 | 7/2001 | Gozani et al. | |
| 6,273,905 B1 | 8/2001 | Streeter | |
| 6,292,701 B1 | 9/2001 | Prass et al. | |
| 6,306,100 B1 | 10/2001 | Prass | |
| 6,308,712 B1 | 10/2001 | Shaw | |
| 6,312,392 B1 | 11/2001 | Herzon | |
| 6,325,764 B1 | 12/2001 | Griffith et al. | |
| 6,334,068 B1 | 12/2001 | Hacker | |
| 6,348,058 B1 | 2/2002 | Melkent et al. | |
| 6,360,750 B1 | 3/2002 | Gerber et al. | |
| 6,371,968 B1 | 4/2002 | Kogasaka et al. | |
| 6,425,859 B1 | 7/2002 | Foley et al. | |
| 6,425,901 B1 | 7/2002 | Zhu et al. | |
| 6,450,952 B1 | 9/2002 | Rioux et al. | |
| 6,451,015 B1 | 9/2002 | Rittman, III et al. | |

| | | |
|---|---|---|
| 6,466,817 B1 | 10/2002 | Kaula et al. |
| 6,468,205 B1 | 10/2002 | Mollenauer et al. |
| 6,468,207 B1 | 10/2002 | Fowler, Jr. |
| 6,500,128 B2 | 12/2002 | Marino |
| 6,520,907 B1 | 2/2003 | Foley et al. |
| 6,524,320 B2 | 2/2003 | DiPoto |
| 6,535,759 B1 | 3/2003 | Epstein et al. |
| 6,564,078 B1 | 5/2003 | Marino et al. |
| 6,579,244 B2 | 6/2003 | Goodwin |
| 6,620,157 B1 | 9/2003 | Dabney et al. |
| 6,645,194 B2 | 11/2003 | Briscoe et al. |
| 6,679,833 B2 | 1/2004 | Smith et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,810,281 B2 | 10/2004 | Brock et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,869,398 B2 | 3/2005 | Obenchain |
| 6,871,099 B1 | 3/2005 | Whitehurst et al. |
| 6,902,569 B2 | 6/2005 | Parmer et al. |
| 6,926,728 B2 | 8/2005 | Zucherman et al. |
| 6,929,606 B2 | 8/2005 | Ritland |
| 6,945,933 B2 | 9/2005 | Branch |
| 6,951,538 B2 | 10/2005 | Ritland |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,198,598 B2 | 4/2007 | Smith et al. |
| 7,207,949 B2 | 4/2007 | Miles et al. |
| 7,226,451 B2 | 6/2007 | Shluzas et al. |
| 7,261,688 B2 | 8/2007 | Smith et al. |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,522,953 B2 | 4/2009 | Kaula et al. |
| 7,556,601 B2 | 7/2009 | Branch et al. |
| 7,582,058 B1 | 9/2009 | Miles et al. |
| 7,643,884 B2 | 1/2010 | Pond et al. |
| 7,691,057 B2 | 4/2010 | Miles et al. |
| 7,717,959 B2 | 5/2010 | William et al. |
| 7,819,801 B2 | 10/2010 | Miles et al. |
| 7,935,051 B2 | 5/2011 | Miles et al. |
| 2001/0039949 A1 | 11/2001 | Loubser |
| 2001/0056280 A1* | 12/2001 | Underwood et al. ........... 606/41 |
| 2002/0007129 A1 | 1/2002 | Marino |
| 2002/0010392 A1 | 1/2002 | Desai |
| 2002/0072686 A1 | 6/2002 | Hoey et al. |
| 2002/0077632 A1 | 6/2002 | Tsou |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0105503 A1 | 6/2003 | Marino |
| 2003/0139648 A1 | 7/2003 | Foley et al. |
| 2003/0149341 A1 | 8/2003 | Clifton |
| 2003/0225405 A1 | 12/2003 | Weiner |
| 2003/0236544 A1 | 12/2003 | Lunsford et al. |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0080320 A1 | 4/2005 | Lee et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0300465 A1 | 12/2008 | Feigenwinter et al. |
| 2009/0124860 A1 | 5/2009 | Miles et al. |
| 2009/0138050 A1 | 5/2009 | Ferree |
| 2009/0192403 A1 | 7/2009 | Gharib et al. |
| 2009/0204016 A1 | 8/2009 | Gharib et al. |
| 2010/0069783 A1 | 3/2010 | Miles et al. |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0174148 A1 | 7/2010 | Miles et al. |

FOREIGN PATENT DOCUMENTS

| | | |
|---|---|---|
| EP | 0 972 538 | 1/2000 |
| FR | 2 795 624 | 1/2001 |
| WO | WO 00/38574 | 7/2000 |
| WO | WO 00/66217 | 11/2000 |
| WO | WO 00/67645 | 11/2000 |
| WO | WO 01/37728 | 5/2001 |
| WO | WO 02/054960 | 7/2002 |
| WO | WO 03/005887 | 1/2003 |
| WO | WO 03/026482 | 4/2003 |
| WO | WO 03/037170 | 5/2003 |
| WO | WO 2005/013805 | 2/2005 |
| WO | WO 2005/030318 | 4/2005 |
| WO | WO 2006/042241 | 4/2006 |
| WO | WO 2006/066217 | 6/2006 |

OTHER PUBLICATIONS

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulpost: analise inicial," *Journal Brasileiro de Neurocirurgia*, 2001, 12(2): 93-96.

Request for Inter Partes Reexamination in re U.S. Patent 7,905,840, dated Feb. 8, 2012, 204 pages.

Traynelis, "Spinal Arthroplasty," *Neurological Focus*, 2002, 13(2): 12 pages.
Zdeblick, Thomas A. (ed.). Anterior Approaches to the Spine. 1999. 43 pages.
Amended Complaint for *NuVasive, Inc. v. Globus Medical, Inc.*, Case No. 1:10-cv-0849 (D. Del., Oct. 5, 2010), 28 pages.
Mayer and Brock, "Percutaneous endoscopic discectomy: surgical technique and preliminary results compared to microsurgical discectomy," *J. Neurosurg*, 1993, 78: 216-225.
Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.
Friedman, "Percutaneous discectomy: An alternative to chemonucleolysis," *Neurosurgery*, 1983, 13(5): 542-547.
Crock, H.V. MD., "Anterior Lumbar Interbody Fusion," Clinical Orthopaedics and Related Research, Number One Hundred Sixty Five, 1982, pp. 157-163, 13 pages.
Larson and Maiman, "Surgery of the Lumbar Spine," Thieme Medical Publishers, Inc., 1999, pp. 305-319.
Medtronic XOMED Surgical Products, Inc., NIM-Response Nerve Integrity Monitor Intraoperative EMG Monitor User's Guide, Revision B, 2000, 47 pages.
"NuVasive's spine surgery system cleared in the US," Pharm & Medical Industry Week, Dec. 10, 2001, 1 page.
Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May 2002, 1 page.
Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia & Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, The Williams & Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6.
Raj et al., "Use of the Nerve Stimulator for Peripheral Blocks," *Regional Anesthesia*, Apr.-Jun. 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Anatomy of the Lumbar Spine in MED TM MicroEndoscopic Discectomy (1997 Ludann Grand Rapids MI), 14 pgs.

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re US Patents 7,207,949; 7,470,236 and 7,582,058, Sep. 18, 2009, 19 pages.
Plaintiffs' Preliminary Invalidity Contentions—Appendices, Sep. 18, 2009, 191 pages.
Plaintiffs' Supplemental Preliminary Invalidity Contentions re US Patents 7,207,949, 7,470,236, and 7,582,058, Sep. 29, 2009, 21 pages.
Plaintiffs' Supplemental Preliminary Invalidity Contentions—Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 1 page (prior to Sep. 25, 2003).
NuVasive Triad™ Tri-Columnar Spinal EndoArthrodesis™ via Minimally Invasive Guidance, 1 page (prior to Sep. 25, 2003).
NuVasive Triad™ Cortical Bone Allograft, 1 page (prior to Sep. 25, 2003).
NuVasive Vertebral Body Access System, 1 page (prior to Sep. 25, 2003).
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
NuVasive letter re 510(k) Premarket Notification INS-1 Intraoperative Nerve Surveillance System, Aug. 24, 2000, 81 pages.
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
Medtronic Sofamor Danek "UNION™ / UNION-L™ Anterior & Lateral Impacted Fusion Devices: Surgical Technique" *Medtronic Sofamor Danek*, 2001, 20 pages.
Defendant's Disclosure of Asserted Claims and Preliminary Infringement Contentions Regarding USP 7,207,949; 7,470,236 and 7,582,058, Aug. 31, 2009, 21 pages.
Kossman et al., "The use of a retractor system (SynFrame) for open, minimal invasive reconstruction of the anterior column of the thoracic and lumbar spine," *Eur Spine J*, 2001, 10: 396-402.
de Peretti et al., "New possibilities in L2-L5 lumbar arthrodesis using a lateral retroperitoneal approach assisted by laparoscopy: preliminary results," *Eur Spine J*, 1996, 5: 210-216.
Litwin et al., "Hand-assisted laparoscopic surgery (HALS) with the handport system," *Annals of Surgery*, 2000, 231(5): 715-723.
Acland's Video Atlas of Human Anatomy, Section 3.1.7: Paravertebral Muscles. Available online: http://aclandanatomy.com/abstract/4010463. Accessed Jul. 11, 2012.
MedlinePlus, a Service of the U.S. National Library of Medicine and National Institutes of Health. Available online: http://www.nlm.nih.gov/medlineplus/. Accessed Jul. 11, 2012.

* cited by examiner

SURGICAL ACCESS SYSTEM AND RELATED METHODS

CROSS REFERENCE TO RELATED APPLICATIONS

This application is a continuation of U.S. patent application Ser. No. 10/967,668 (filed on Oct. 18, 2004) entitled "Surgical Access System and Related Methods," which: (1) claims the benefit of priority from U.S. Provisional Patent Application Ser. No. 60/512,594 (filed on Oct. 17, 2003) entitled "System and Methods for Performing Lateral Lumbar Surgery," and (2) is a continuation-in-part of International Patent Application Serial No. PCT/US04/31768 (filed on Sep. 27, 2004 by Miles et al.) entitled "Surgical Access System and Related Methods," which claims the benefit of priority from U.S. Provisional Patent Application Ser. No. 60/506,136 (filed on Sep. 25, 2003), the entire contents of all these prior applications are hereby expressly incorporated by reference into this disclosure as if set forth fully herein. The present application also incorporates by reference the following co-assigned patent applications in their entireties: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003 (collectively "NeuroVision PCT Applications").

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator of split construction, and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't infringe upon the region of the exiting nerve roots.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior refractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

According to another aspect of the invention, a minimally invasive lateral lumber surgery may be performed using various embodiments of the surgical access system. The surgical method may be accomplished by guiding at least a portion of the tissue distraction assembly to the surgical target site using a lateral, retroperitoneal approach. According to some embodiments, the access system is used to access the lumbar spine via a direct lateral, retroperitoneal approach. In such embodiments, blunt finger dissection may be used to safely enter the retroperitoneal space posteriorly and sweep the peritoneal cavity anteriorly. A distal end of the K-wire, and possibly other components of the tissue distraction assembly, are then escorted through the retroperitoneal space to the psoas muscle utilizing finger dissection. In some instances, the initial dilator is guided through the retroperitoneal space by a finger in contact with the distal end, so the potential of peritoneal disruption may be reduced.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
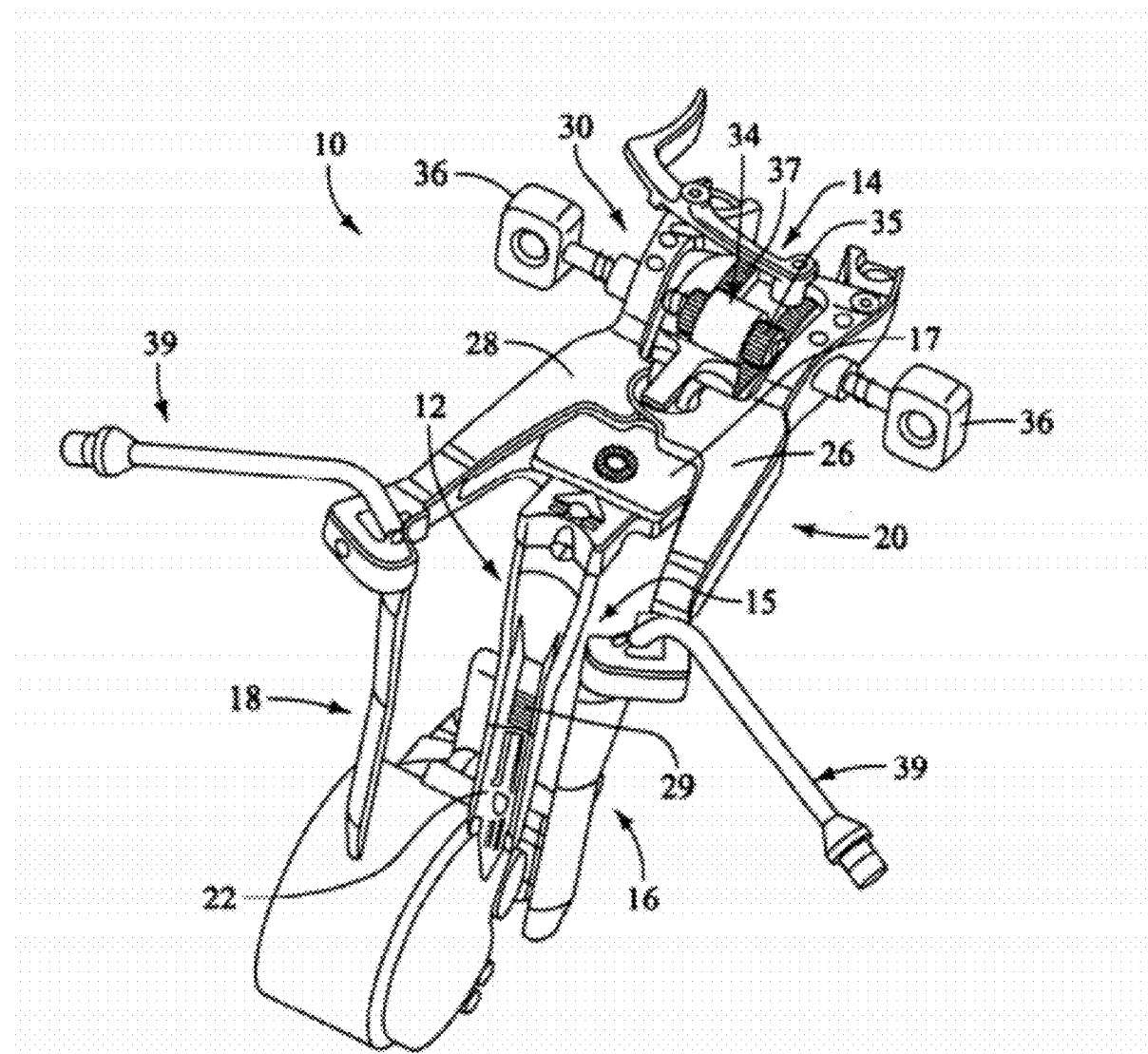
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures. In some embodiments, the surgical access system may be used access a surgical target site on the spine via a substantially lateral, retroperitoneal approach (as shown, for example, in FIGS. 23-50).

These electrodes are preferably provided for use with a nerve surveillance system such as, by way of example, the type shown and described in the co-pending and commonly assigned NeuroVision PCT Applications referenced above, the entire contents of which are expressly incorporated by reference as if set forth herein in their entirety. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue refraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a distal shim extension in positioned within the posterior region of the disc space. If done before retraction, this helps ensure that the posterior refractor blade will not move posteriorly during the retraction process, even though the other retractor blades (i.e. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (i.e. nerves, vasculature, etc. . . . ) into or out of the operative corridor. Once the operative corridor is established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a plurality of retractor blades extending from a handle assembly 20. By way of example only, the handle assembly 20 is provided with a first retractor blade 12, a second retractor blade 16, and a third refractor blade 18. The retractor assembly 10 is shown in a fully retracted or "open" configuration, with the retractor blades 12, 16, 18 positioned a distance from one another so as to form an operative corridor 15 there between and extending to a surgical target site (e.g. an annulus of an intervertebral disc). Although shown and described below with regard to the three-bladed configuration, it is to be readily appreciated that the number of retractor blades may be increased or decreased without departing from the scope of the present invention. Moreover, although described and shown herein, for example in FIGS. 1, 9-18, and 23-50, with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

Figure 2:
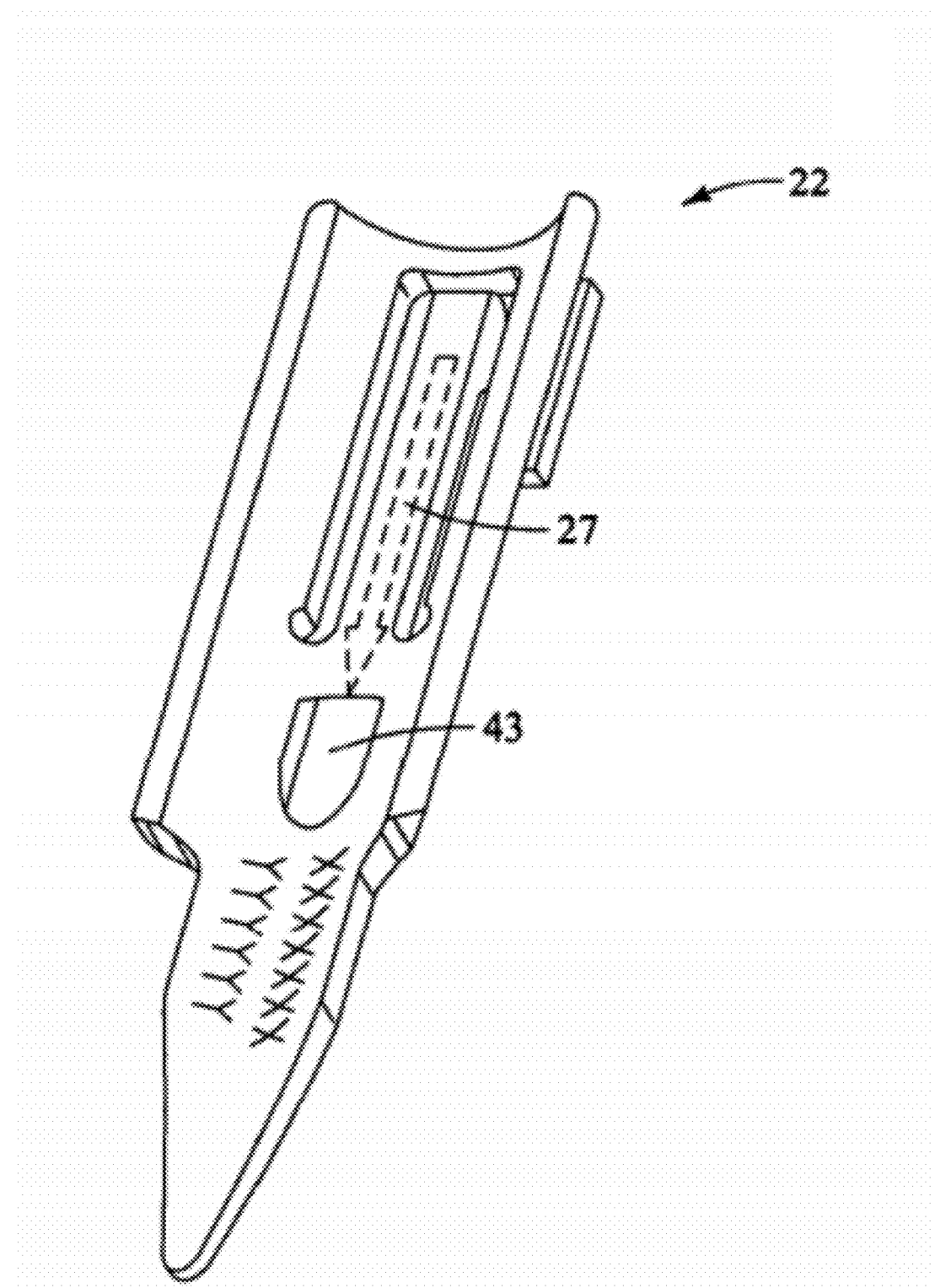
FIGS. 2-3 are perspective views illustrating the front and back of a shim element for use with a posterior retractor blade of the retractor according to the retractor of the present invention.
Figure 3:
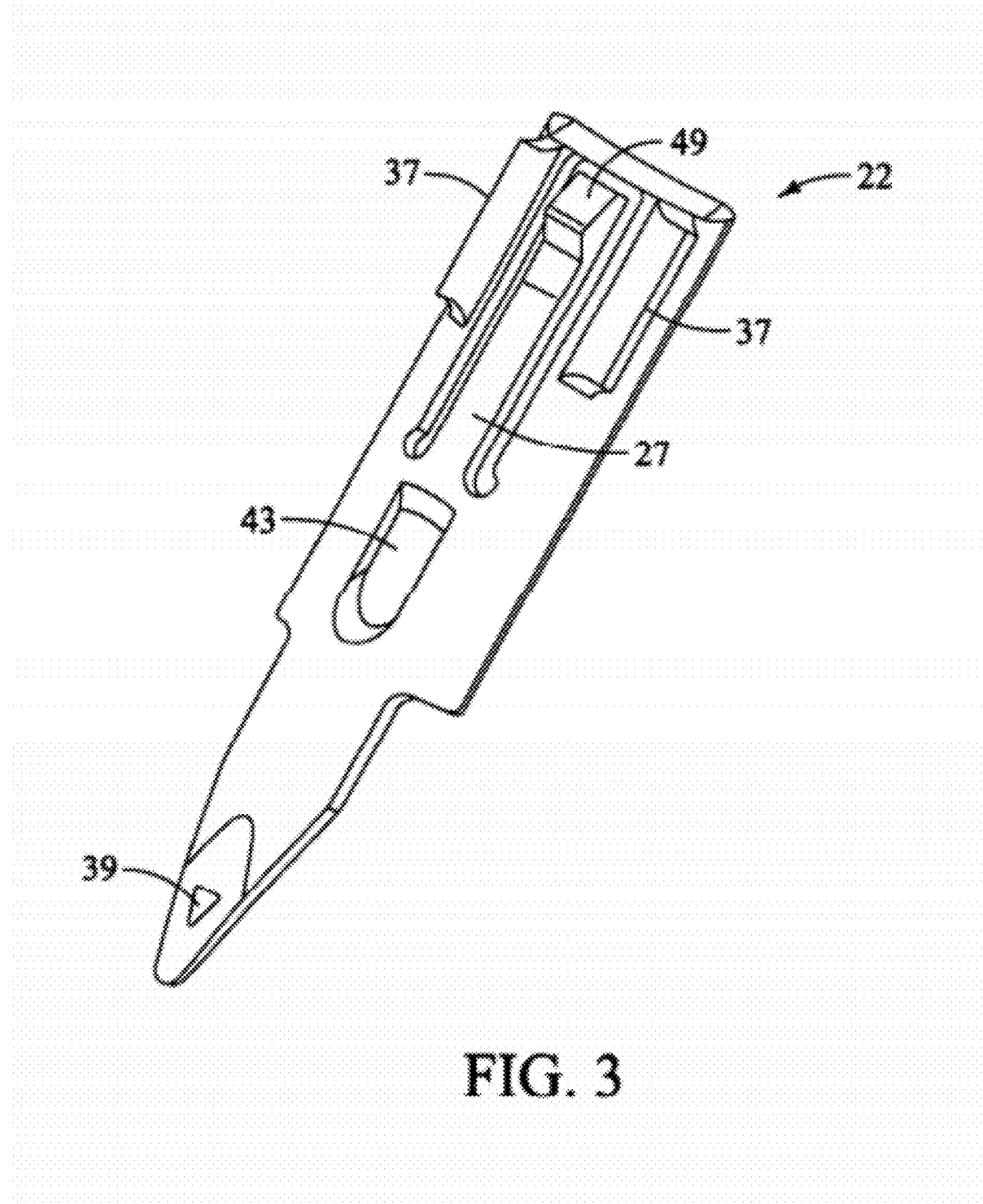
Figure 4:
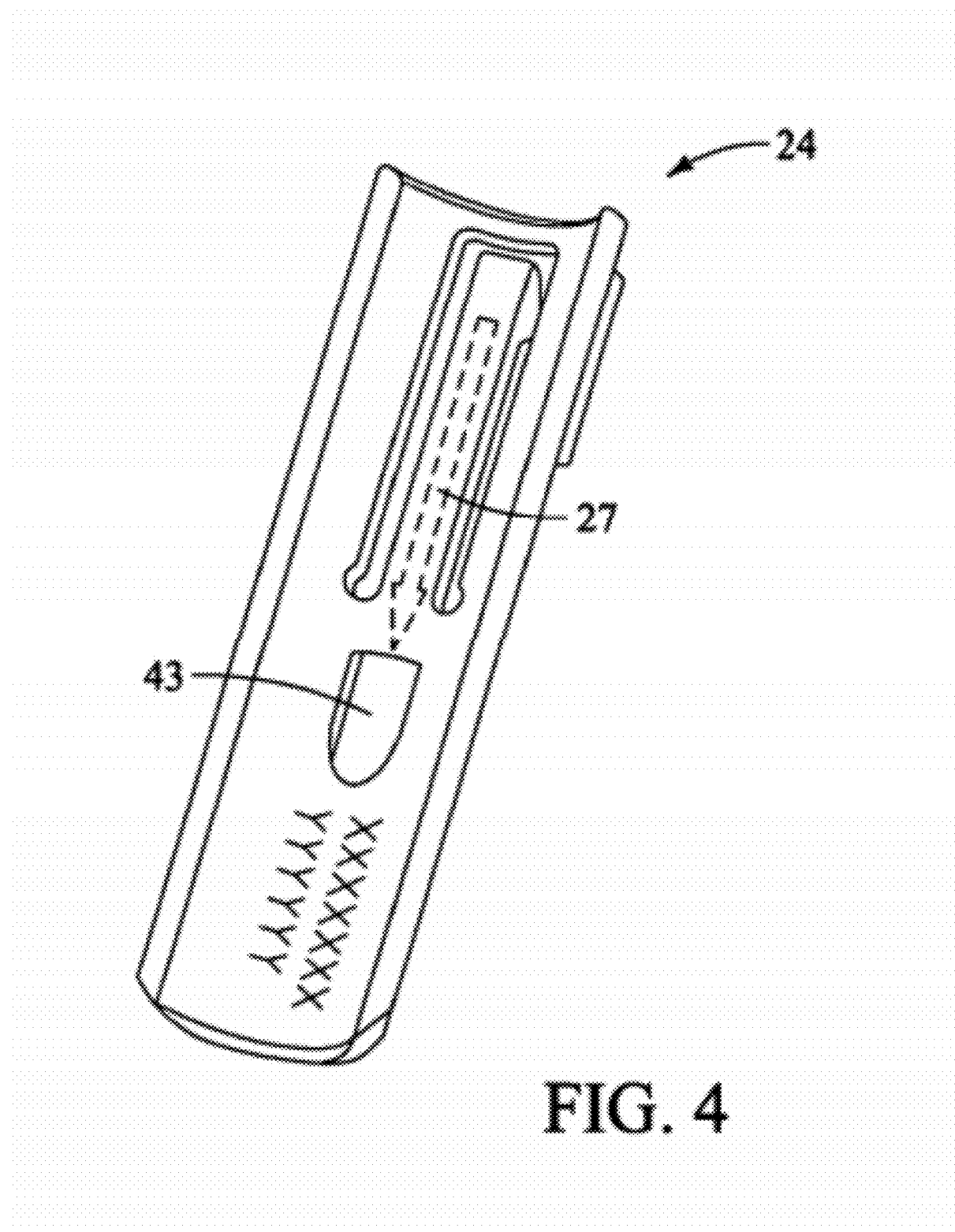
FIGS. 4-5 are perspective views illustrating the front and back of a narrow retractor extender for use with one of a cephalad and caudal retractor blade according to the retractor of the present invention.
Figure 5:
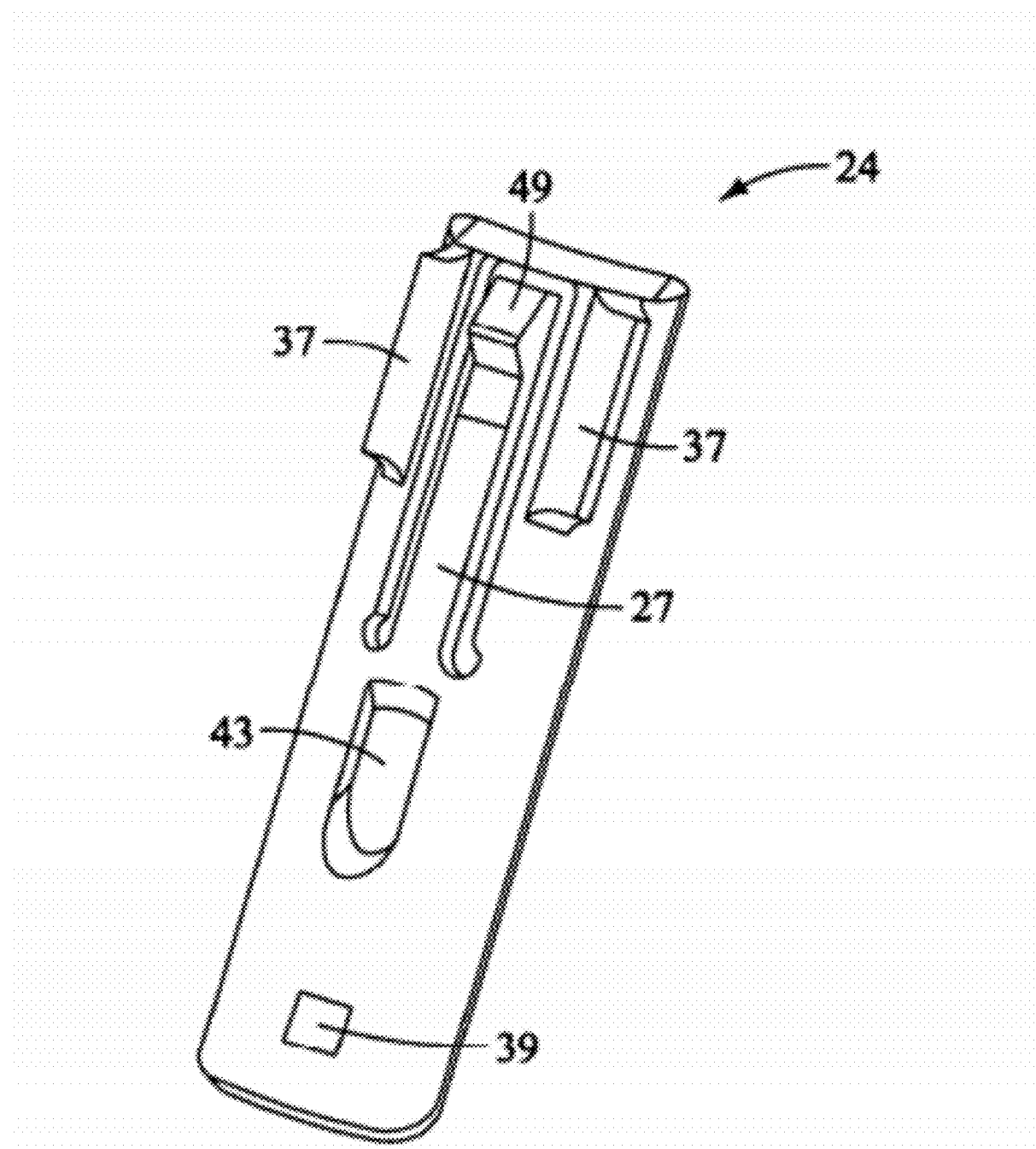
Figure 6:
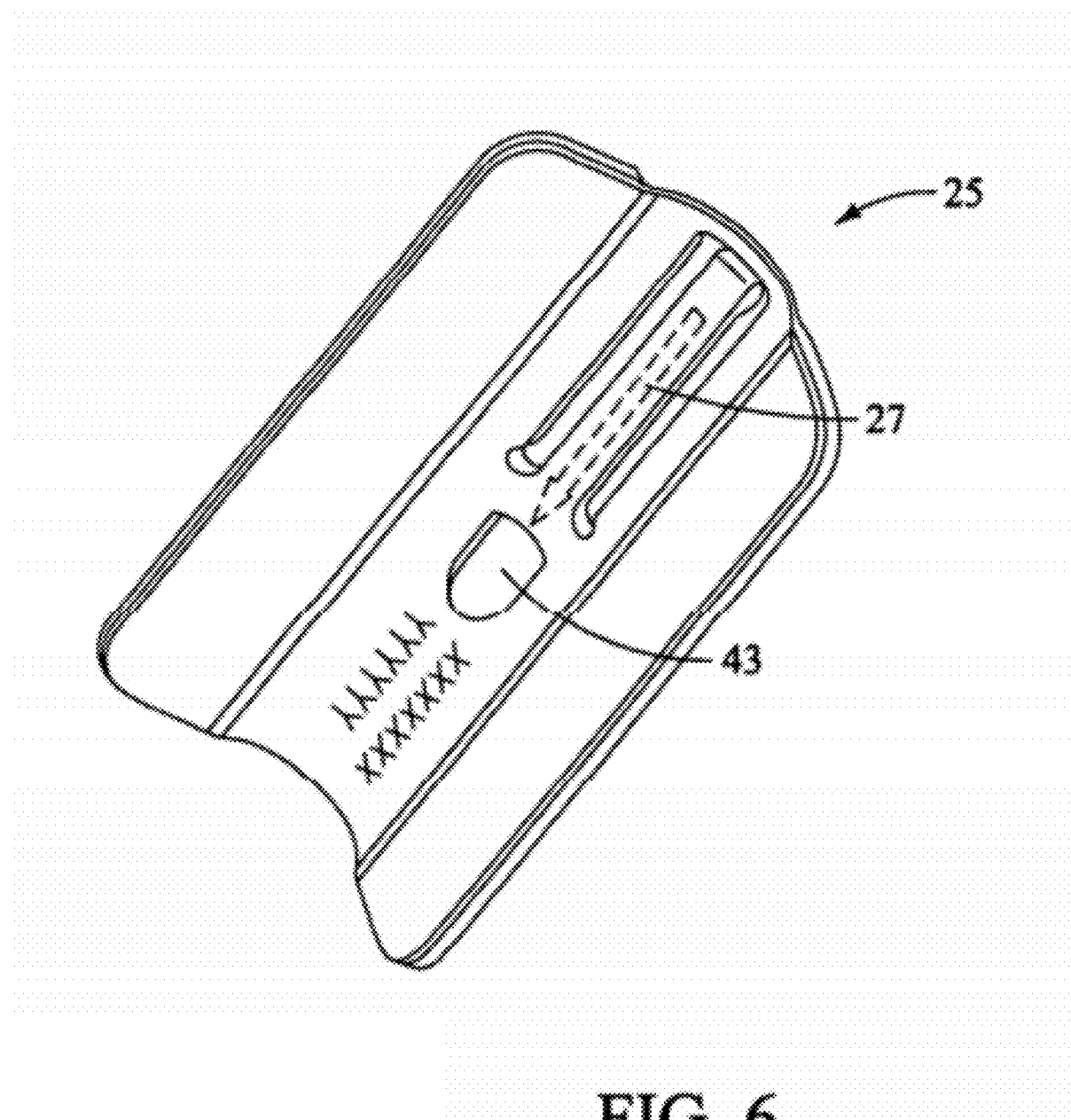
FIGS. 6-7 are perspective views illustrating the front and back of a wide retractor extender for use with one of a cephalad and caudal retractor blade according to the retractor of the present invention.
Figure 7:
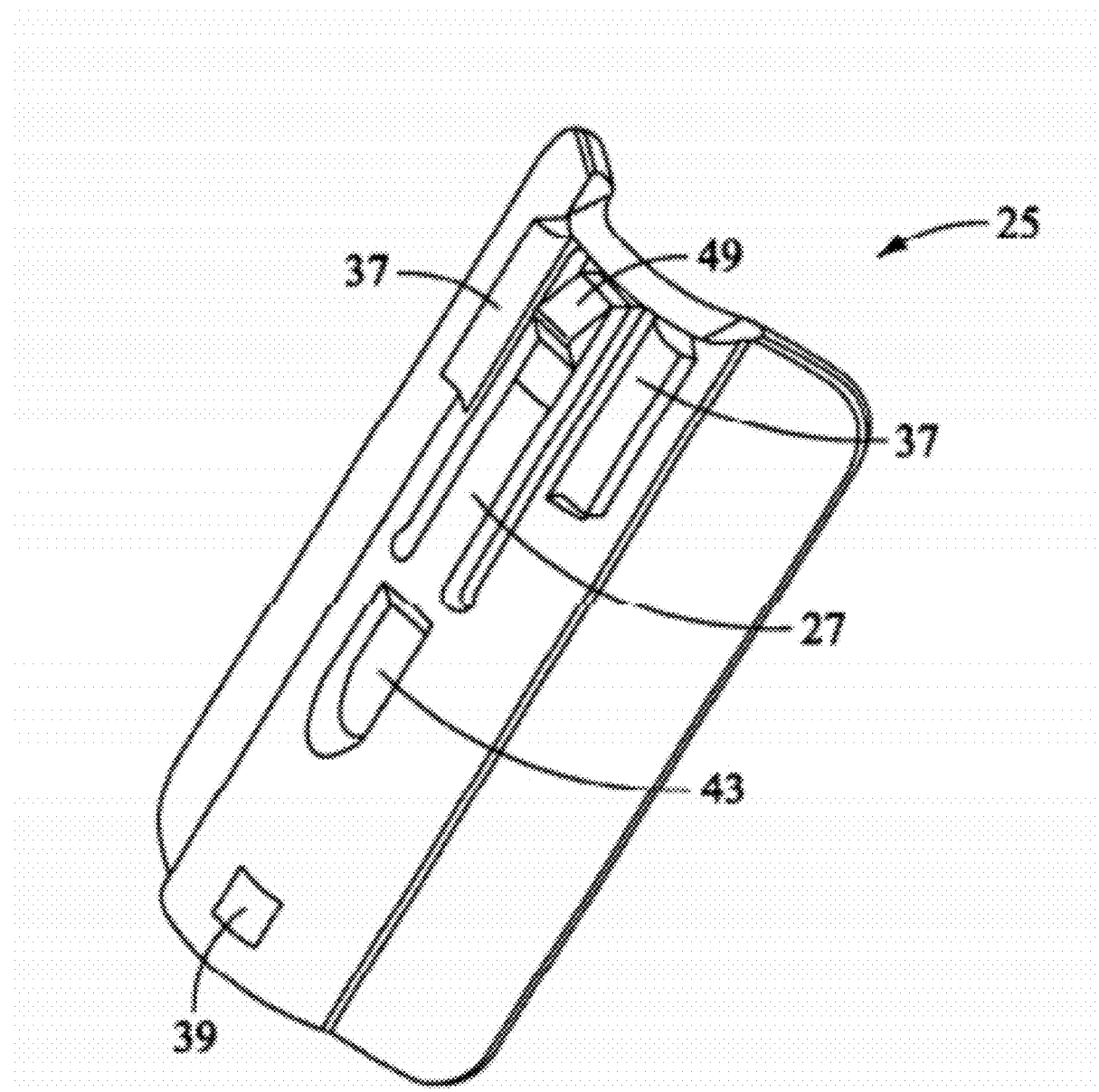

The retractor blades 12, 16, 18 may be equipped with various additional features or components. By way of example only, posterior retractor blade 12 may be equipped with a shim element 22 (shown more clearly in FIGS. 2-3). Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc. . . . ) into or out of the operative corridor. Each of the remaining refractor blades (cephalad-most blade 16 and caudal-most blade 18) may be equipped with a refractor extender, such as the narrow retractor extender 24 shown in FIGS. 4-5 or the wide retractor extender 25 shown in FIGS. 6-7. The retractor extenders 24/25 extend from the cephalad-most and caudal-most retractor blades 16, 18 to form a protective barrier to prevent the ingress or egress of instruments or biological structures (i.e. nerves, vasculature, etc. . . . ) into or out of the operative corridor 15.

According to the present invention, any or all of the retractor blades 12, 16, 18, the shim element 22 and/or the retractor extenders 24/25 may be provided with one or more electrodes 39 (preferably at their distal regions) equipped for use with a nerve surveillance system, such as, by way of example, the type shown and described in the NeuroVision PCT Applications. Each of the shim element 22 and/or the retractor extenders 24/25 may also be equipped with a mechanism to selectively and releasably engage with the respective retractor blades 12, 16, 18. By way of example only, this may be accomplished by configuring the shim element 22 and/or the retractor extenders 24/25 with a tab element 27 capable of engaging with corresponding rachet-like grooves (shown at 29 in FIG. 1) along the inner-facing surfaces of the retractor blades 12, 16, 18. Each of the shim element 22 and/or the retractor extenders 24/25 is provided with a pair of engagement elements 37 having, by way of example only, a generally dove-tailed cross-sectional shape. The engagement elements 37 are dimensioned to engage with receiving portions on the respective retractor blades 12, 16, 18. In a preferred embodiment, each of the shim element 22 and/or the retractor extenders 24/25 are provided with an elongate slot 43 for engagement with an insertion tool (not shown). Each tab member 27 is also equipped with an enlarged tooth element 49 which engages within corresponding grooves 29 provided along the inner surface of the retractor blades 12, 16, 18.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism shown generally at 30. The cephalad-most retractor blade 16 is rigidly coupled (generally perpendicularly) to the end of the first arm member 26. The caudal-most retractor blade 18 is rigidly coupled (generally perpendicularly) to the end of the second arm member 28. The posterior retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Figure 8:
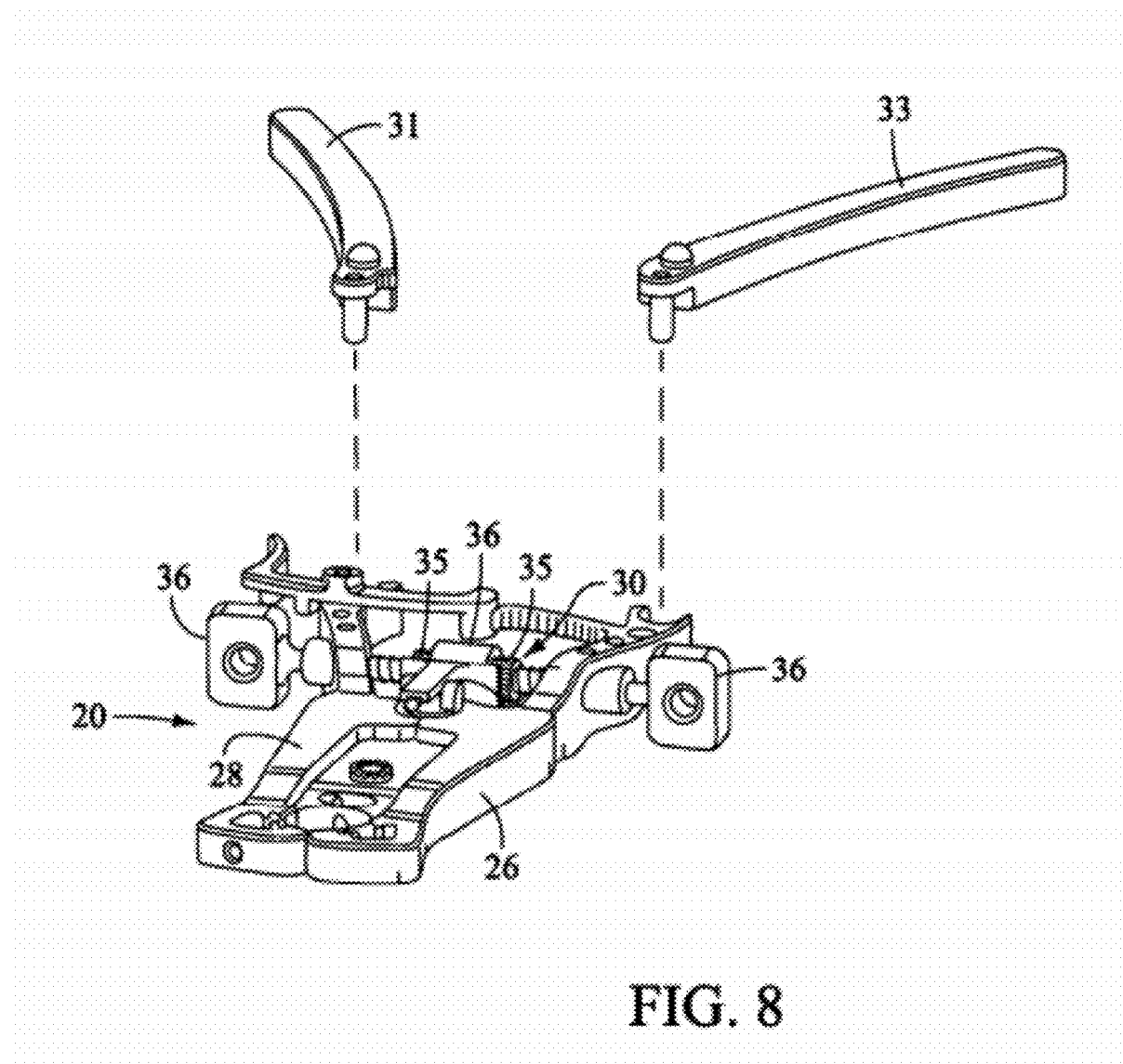
FIG. 8 is a perspective, partially exploded view of the retractor assembly of the present invention, without the retractor blades.

Through the use of handle extenders 31, 33 (FIG. 8), the arms 26, 28 may be simultaneously opened such that the cephalad-most and caudal-most retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices 39 may be coupled to one or more of the refractor blades 12, 16, 18 to direct light down the operative corridor 15.

Figure 9:
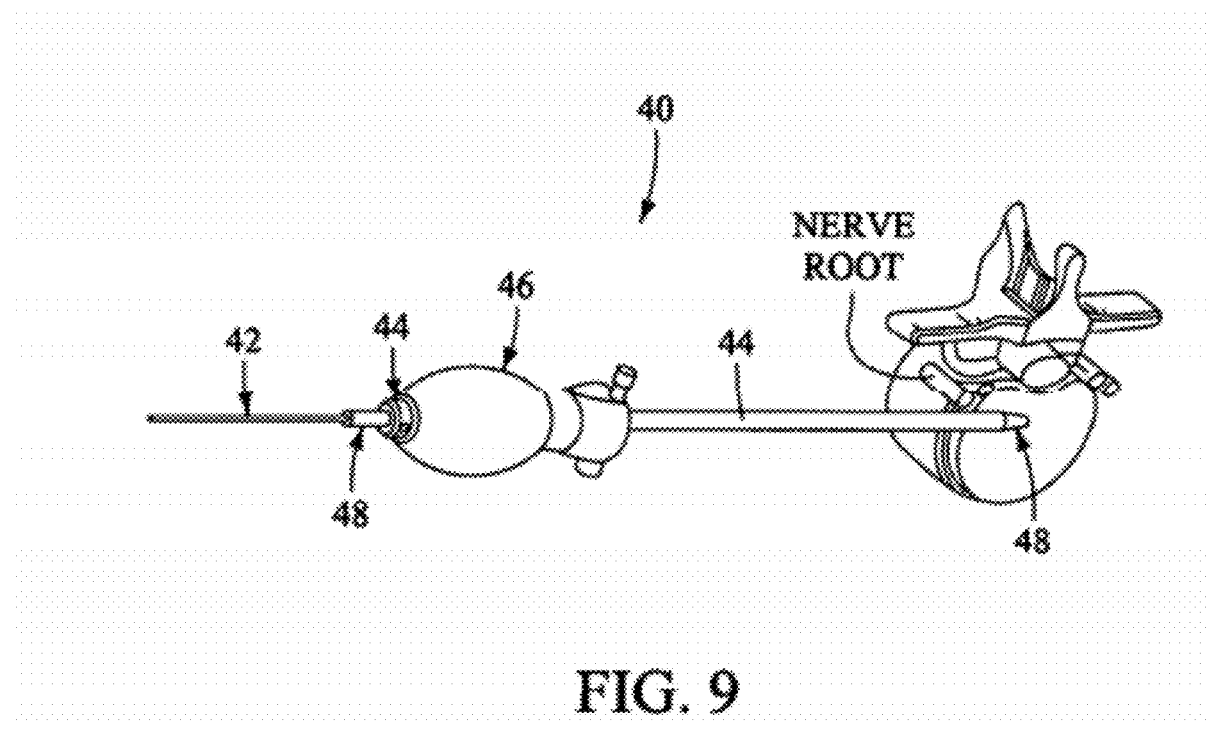
FIG. 9 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 10:
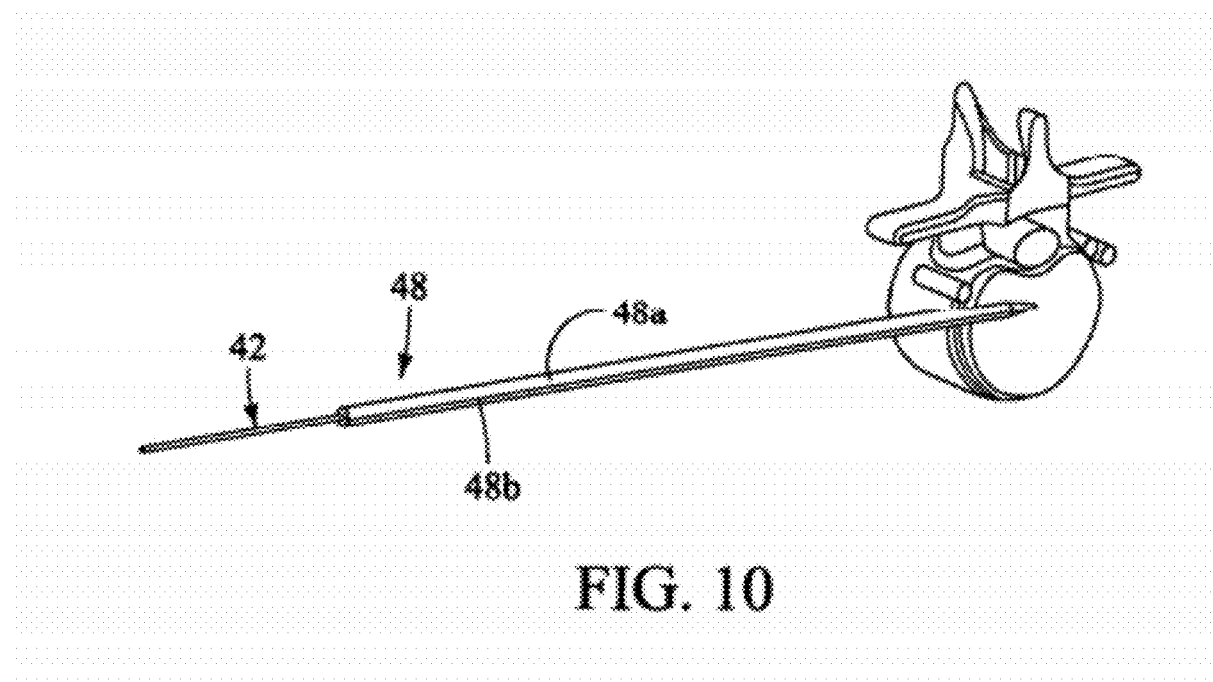
FIG. 10 is a perspective view illustrating the K-wire and split-dilator of the initial distraction assembly with the initial dilating cannula and handle removed.
Figure 11:
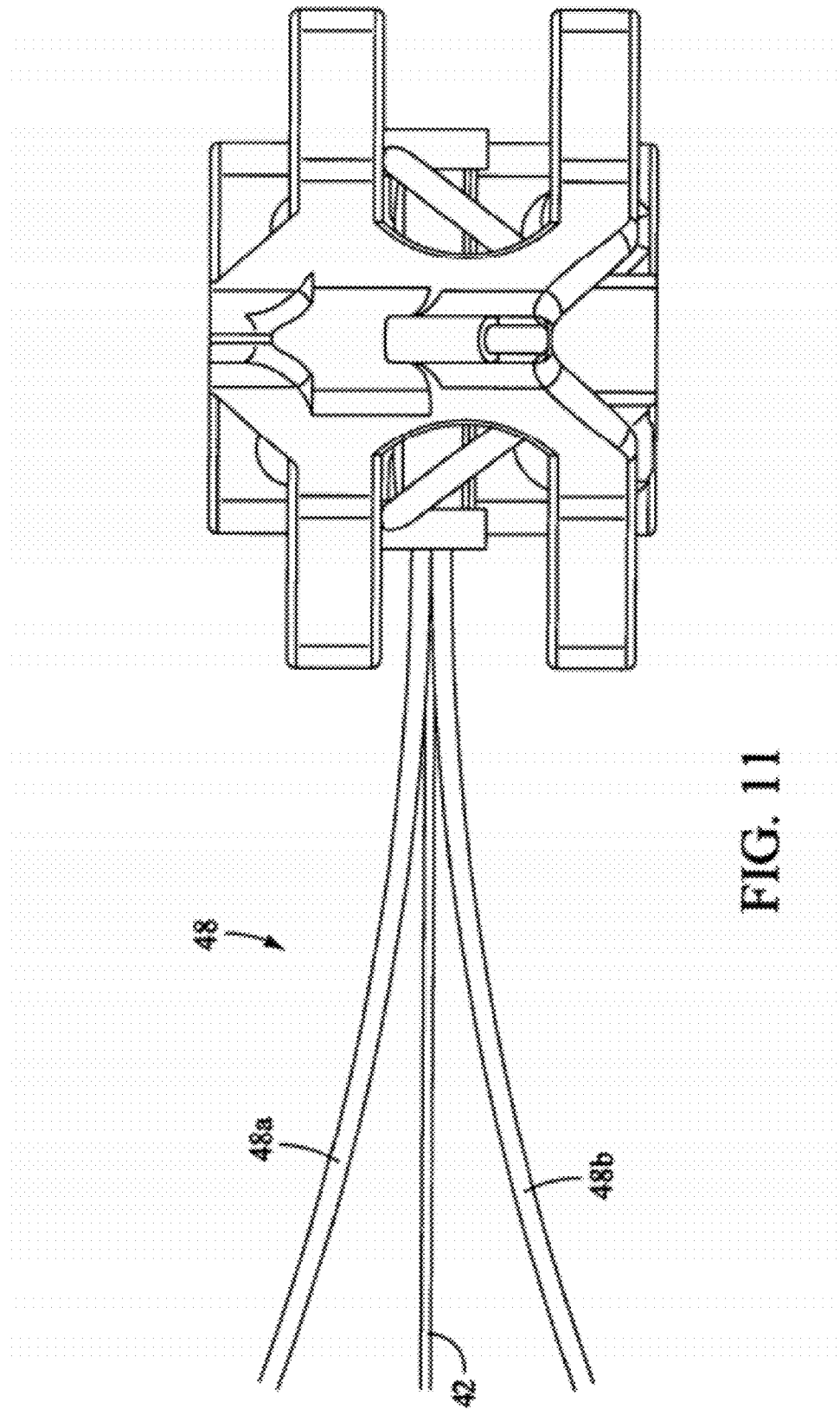
FIG. 11 is a posterior view of the vertebral target site illustrating the split-dilator of the present invention in use distracting in a generally cephalad-caudal fashion according to one aspect of the present invention.

FIG. 9 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). One exemplary method for advancing an initial dilator towards a spinal target site is described in more detail later in connection with FIGS. 23-50. Again, this is preferably accomplished while employing the nerve detection and/or direction features described above. After the initial dilating assembly 40 is advanced such that the distal ends of the split-dilator 48 and initial dilator 44 are positioned within the disc space (FIG. 9), the initial dilator 44 and handle 46 are removed (FIG. 10) to thereby leave the split-dilator 48 and K-wire 42 in place. As shown in FIG. 11, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications.

Figure 12:
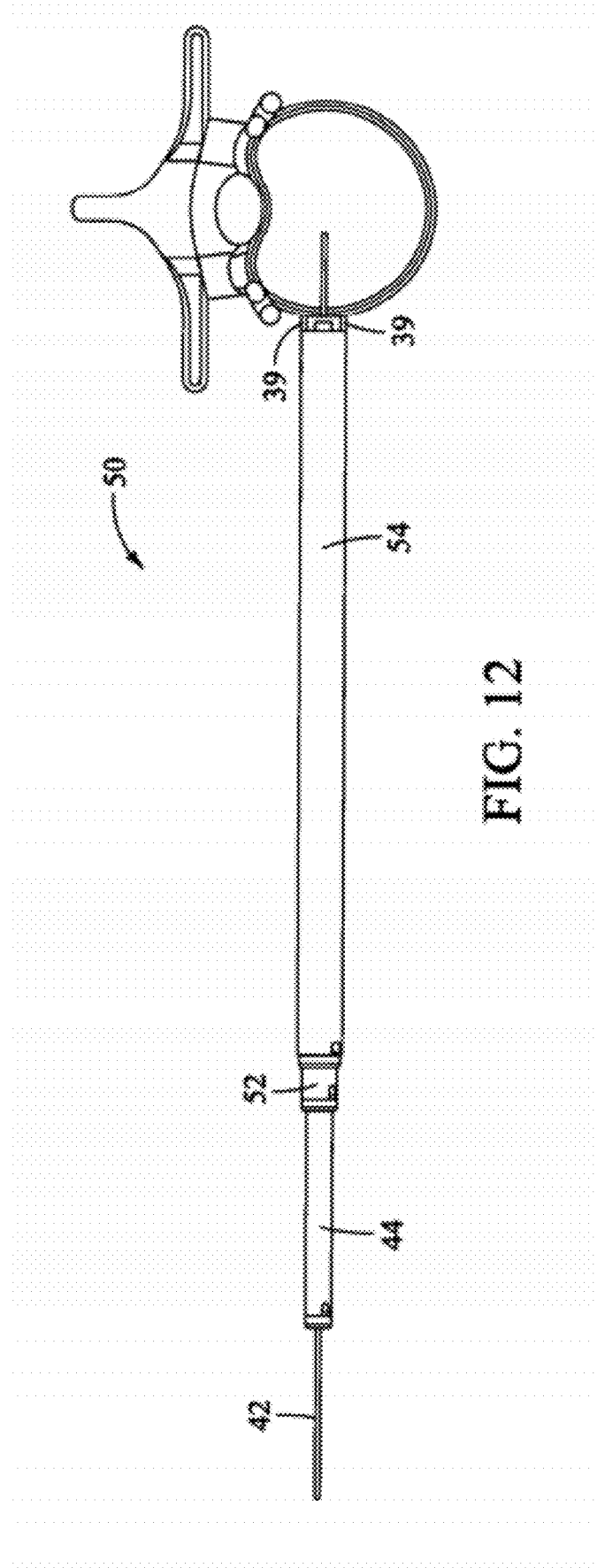
FIG. 12 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 12. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54 may be, according to the present invention, provided with one or more electrodes (preferably at their distal regions) equipped for use with a nerve surveillance system, such as, by way of example, the type shown and described in the Neuro-Vision PCT Applications.

Figure 13:
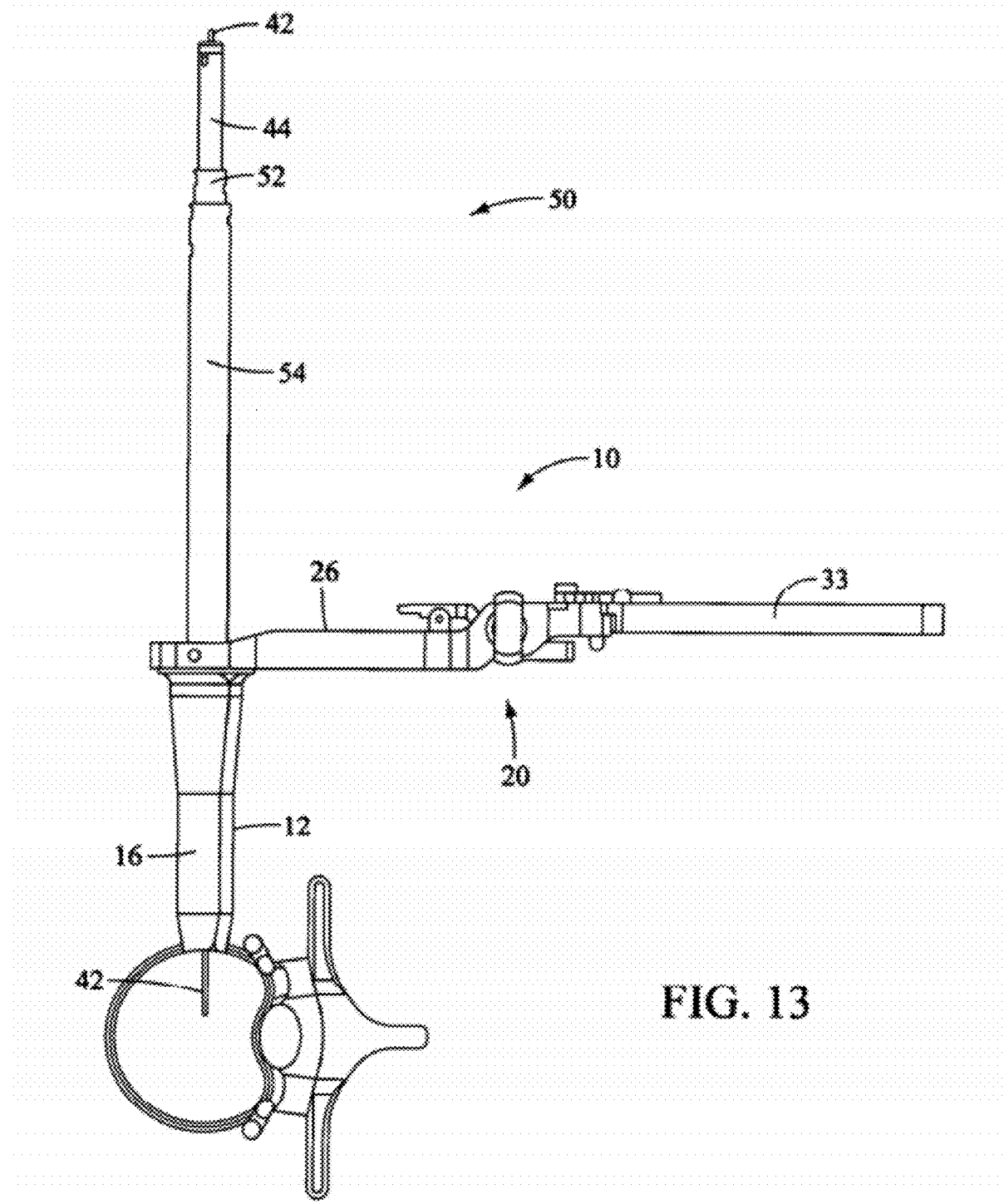
FIG. 13 is a side view of a retractor assembly according to the present invention, comprising a handle assembly having three (3) retractor blades extending there from (posterior, cephalad-most, and caudal-most) disposed over the secondary distraction assembly of FIG. 12 (shown in a first, closed position)
Figure 14:
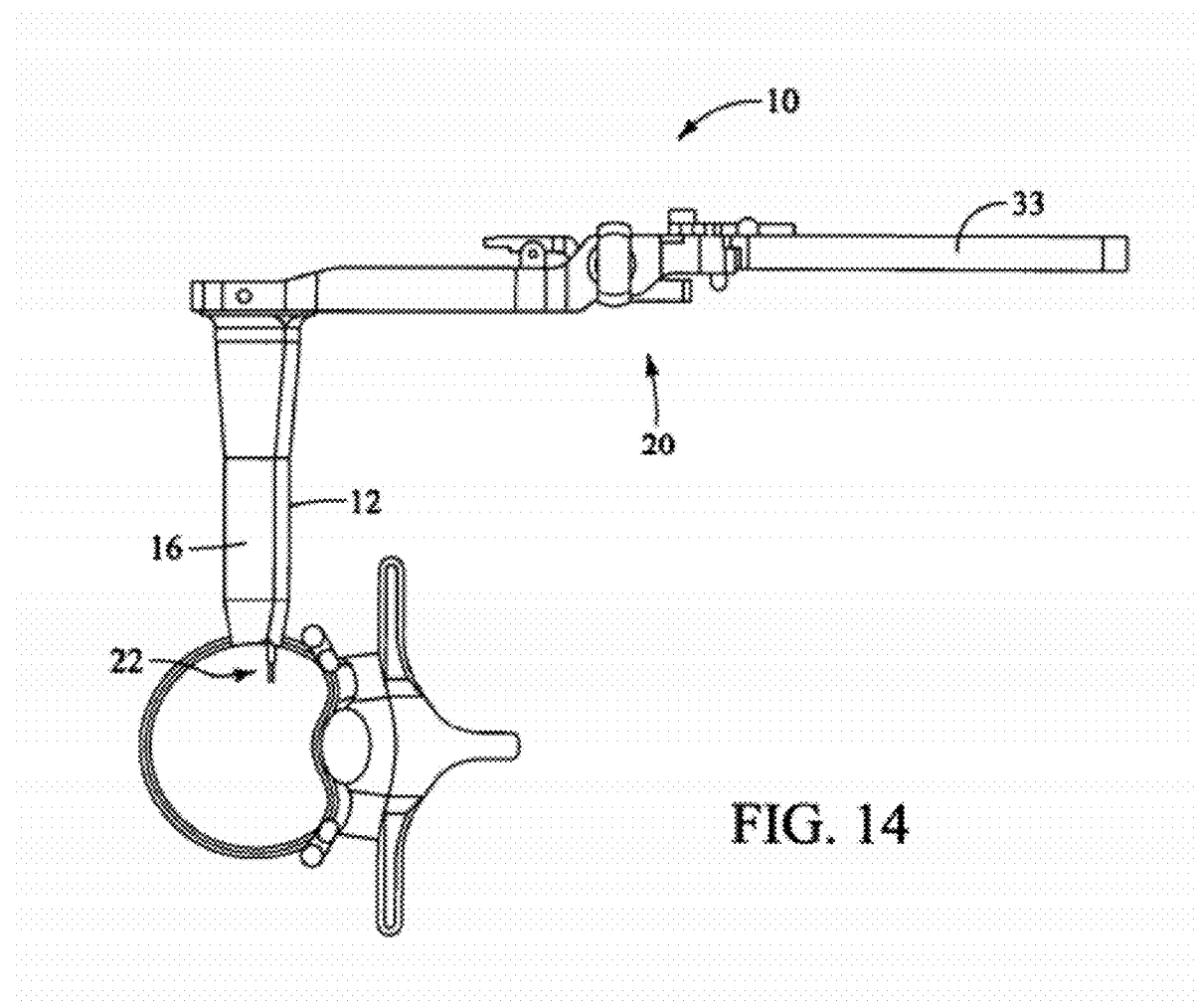
FIG. 14 is a side view of a retractor assembly according to the present invention, comprising a handle assembly having three (3) retractor blades extending there from (posterior, cephalad-most, and caudal-most) with the secondary distraction assembly of FIG. 12 removed and shim element introduced.
Figure 15:
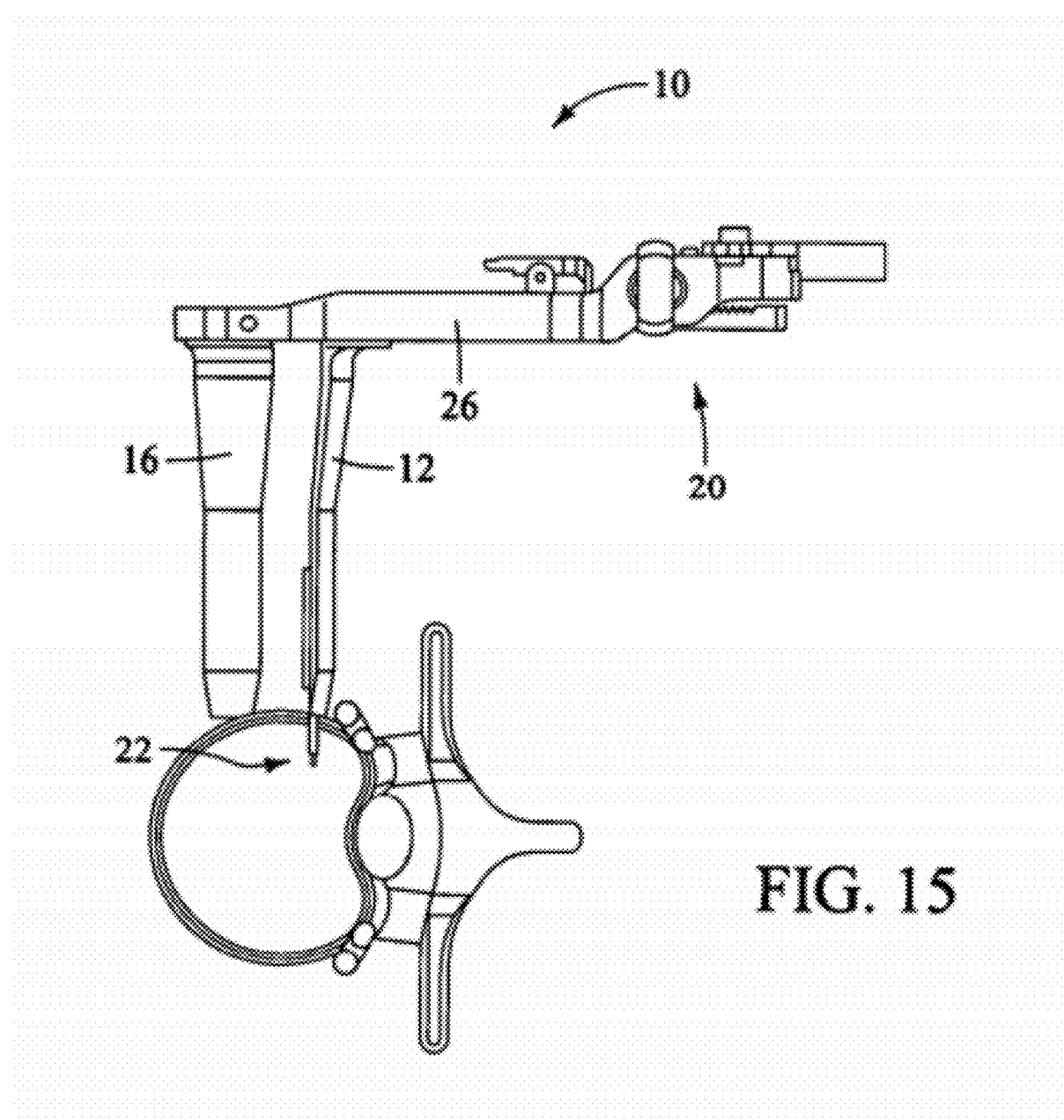
FIGS. 15-16 are perspective and top views, respectively, of the retractor assembly in a second, opened (i.e. retracted) position to thereby create an operative corridor to a surgical target site according to the present invention.
Figure 16:
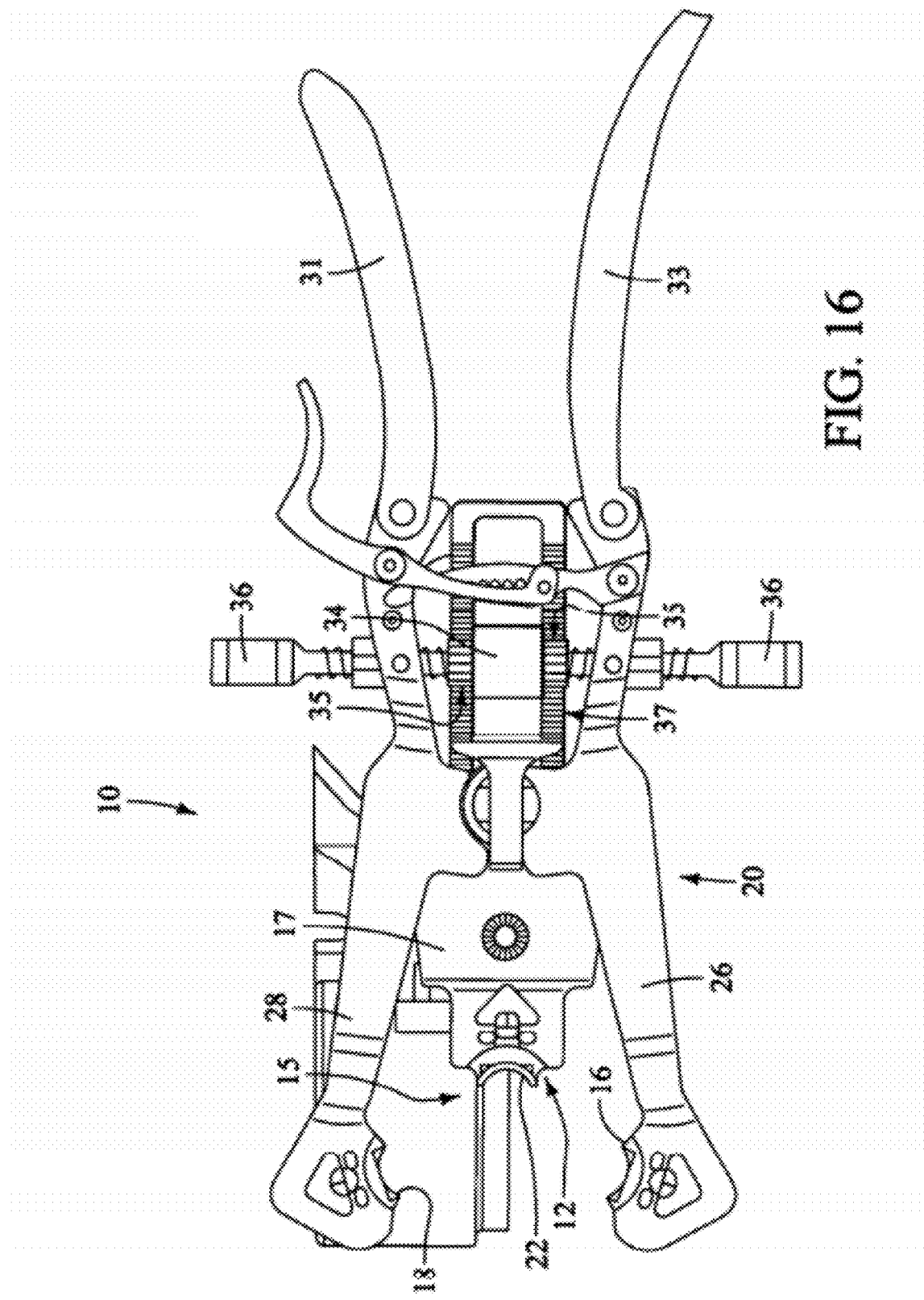
Figure 17:
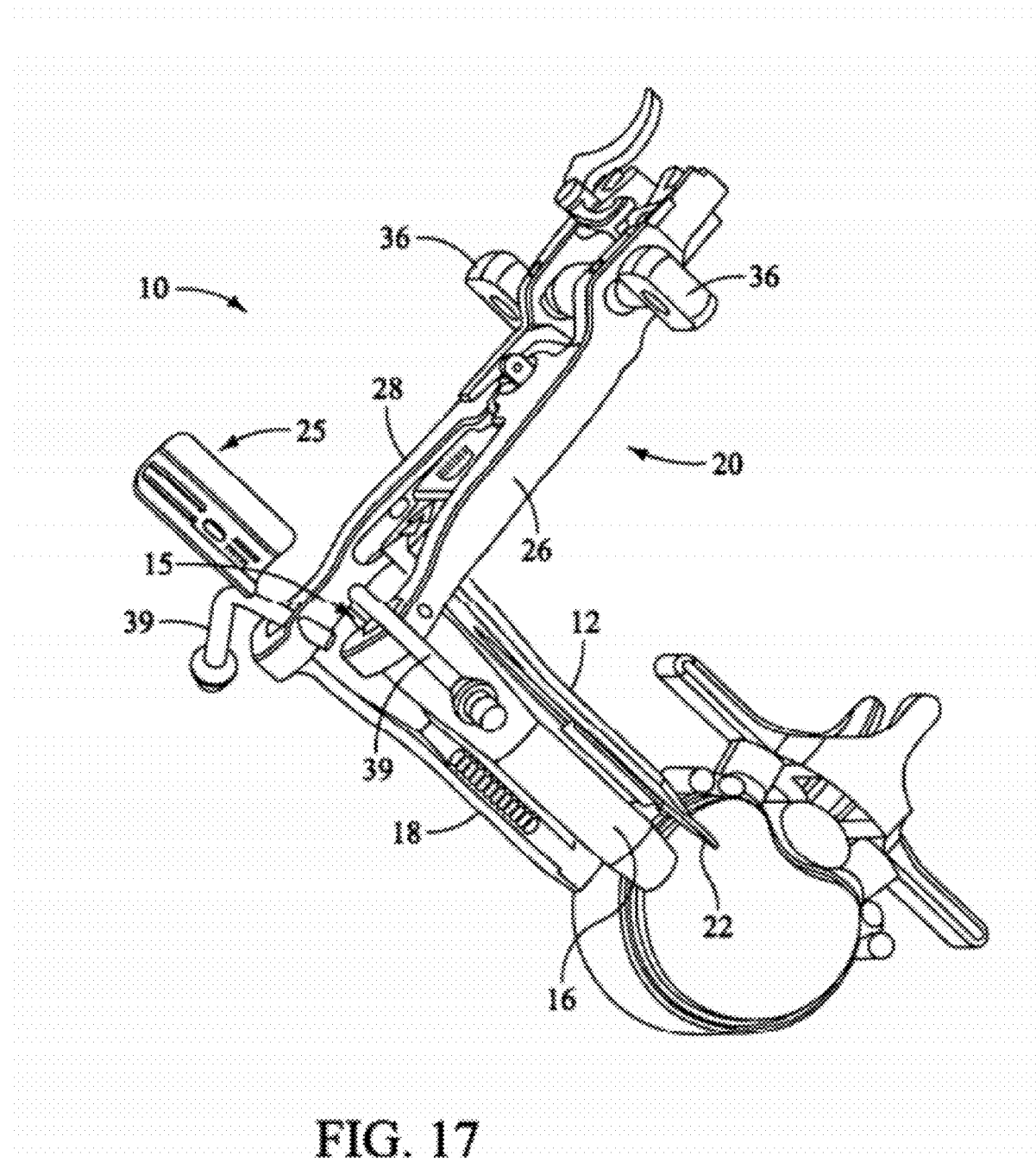
FIGS. 17-18 are perspective and side views, respectively, of the retractor assembly in the second, opened (i.e. retracted) position (with the secondary distraction assembly removed) and with the retractor extenders of FIGS. 4-5 and 6-7 coupled to the retractor according to the present invention.
Figure 18:
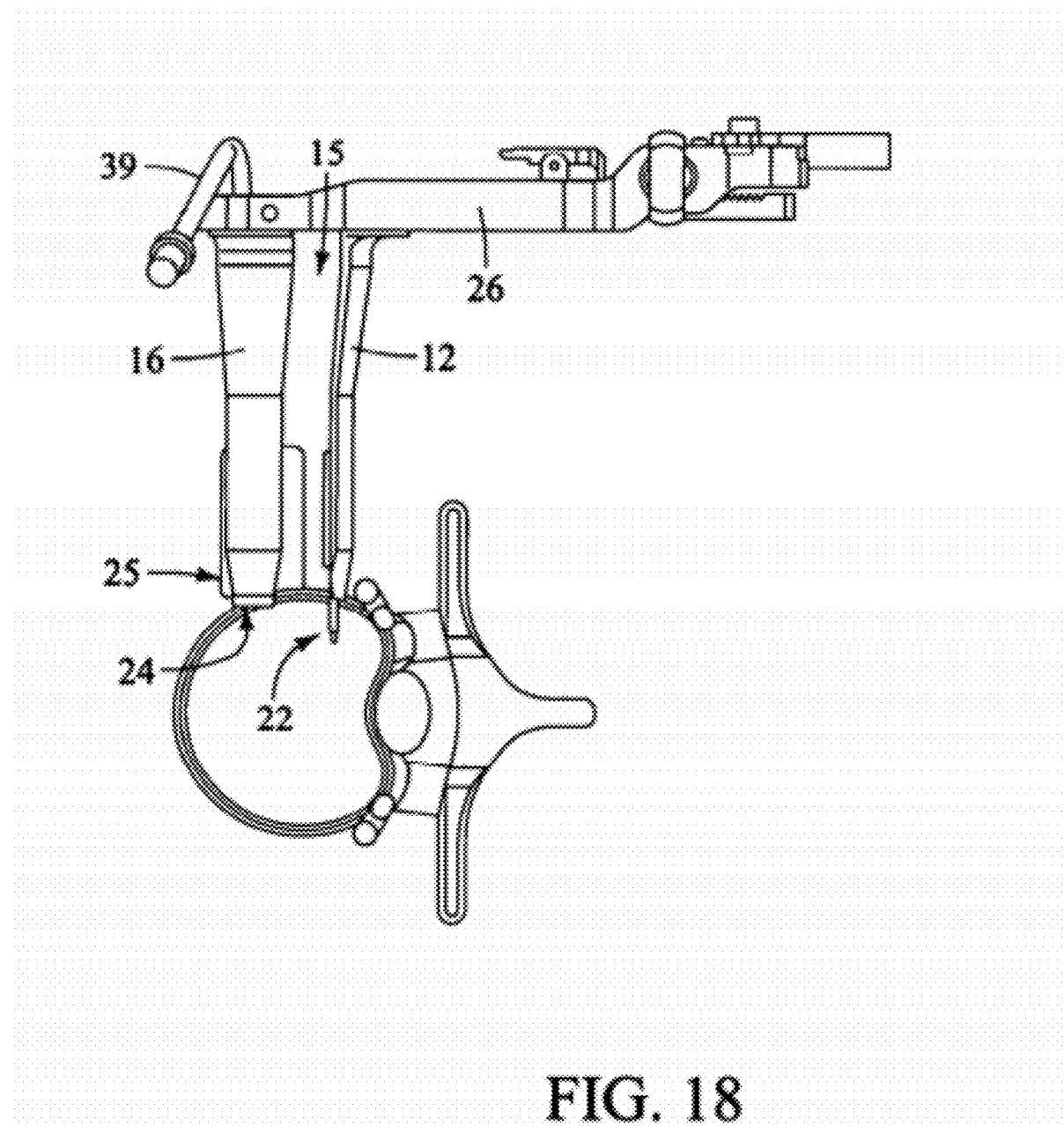

As shown in FIG. 13, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another). Once advanced to the surgical target site, the sequential dilation assembly 50 may be removed and the shim element 22 engaged with the posterior retractor blade 12 such that the distal end thereof extends into the disc space as shown in FIG. 14. At this point, the handle assembly 20 may be operated to move the retractor blades 16, 18 into a second, open or "retracted" position as shown generally in FIGS. 15-16. As one can see, the posterior retractor blade 12 is allowed to stay in the same general position during this process, such that the cephalad-most and caudal-most retractor blades 14, 16 move away from the posterior retractor blade 12. At this point, the narrow and wide retractor extenders 24, 25 may be engaged with the caudal-most retractor blade 18 and cephalad-most retractor blade 16, respectively, as shown in FIGS. 17-18.

As mentioned above, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or refraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the following commonly owned and co-pending NeuroVision PCT Applications referenced above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed. For example, the surgical access system may be advantageously used to traverse tissue through the retroperitoneal space and the psoas muscle during a substantially lateral, retroperitoneal approach to the lumbar spine, as shown in FIGS. 23-50.

Figure 19:
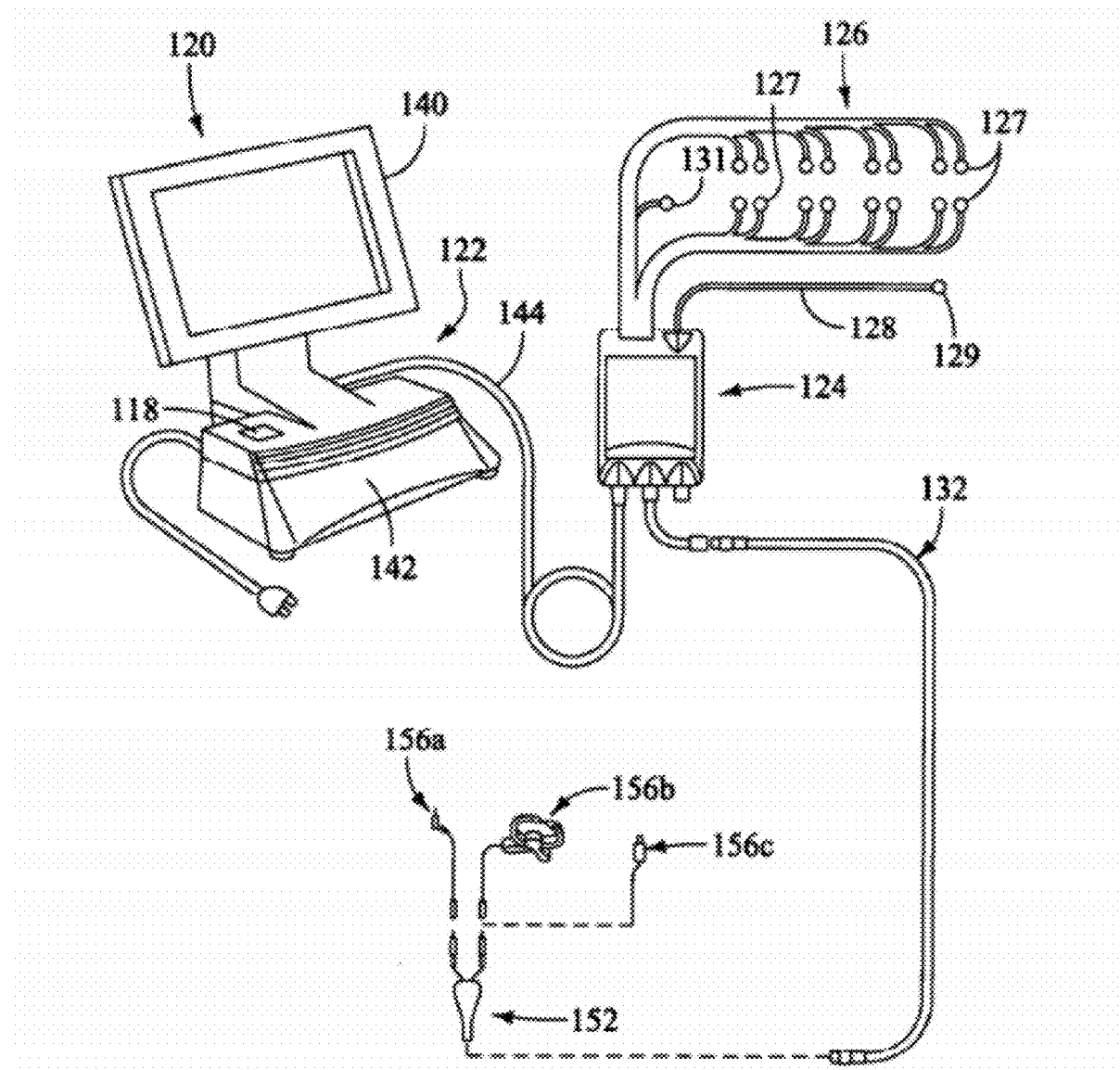
FIG. 19 is a perspective view of an exemplary nerve monitoring system capable of performing nerve monitoring before, during and after the creating of an operative corridor to a surgical target site using the surgical access system in accordance with the present invention.
Figure 20:
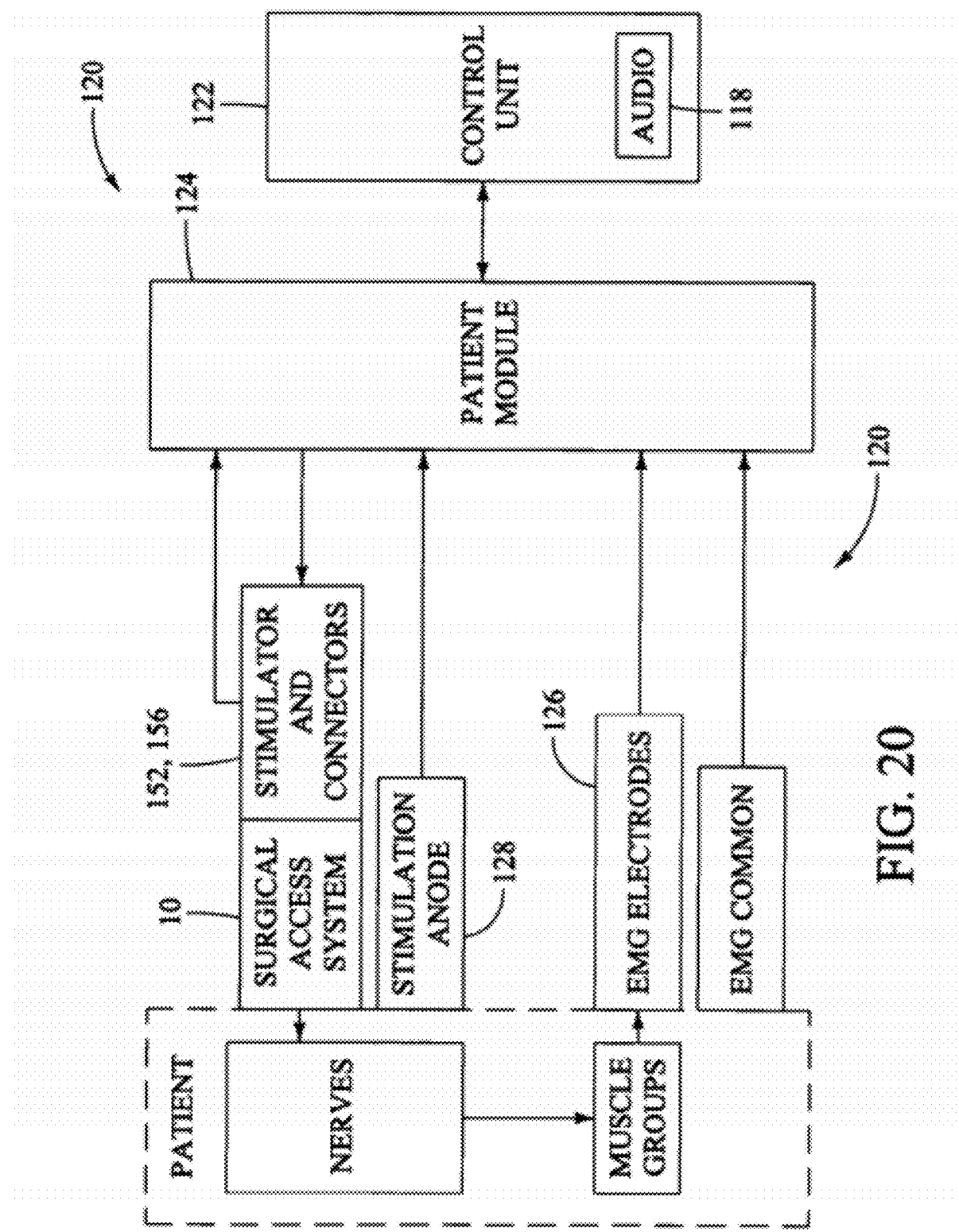
FIG. 20 is a block diagram of the nerve monitoring system shown in FIG. 19.

FIGS. 19-20 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system of the present invention (retractor assembly 10 of FIG. 1 and distraction assemblies 40, 50 of FIGS. 9-12). More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156*a*, 156*b*, 156*c*. The connectors 156*a*, 156*b*, 156*c* are suitable to establish electrical communication between the hand-held stimulation controller 152 and (by way of example only) the stimulation electrodes on the K-wire 42, the dilators 44, 48, 52, 54, the retractor blades 12, 16, 18 and/or the shim members 22, 24, 25 (collectively "surgical access instruments").

In order to use the monitoring system 120, then, these surgical access instruments must be connected to the connectors 156*a*, 156*b* and/or 156*c*, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the K-wire 42, the dilators 44, 48, 52, 54, the retractor blades 12, 16, 18 and/or the shim elements 22, 24, 25 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column. For example, one such operative corridor to an intervertebral target site may be established through the retroperitoneal space and the psoas muscle during a substantially lateral, retroperitoneal approach to the lumbar spine, as shown in FIGS. 23-50.

Figure 21:
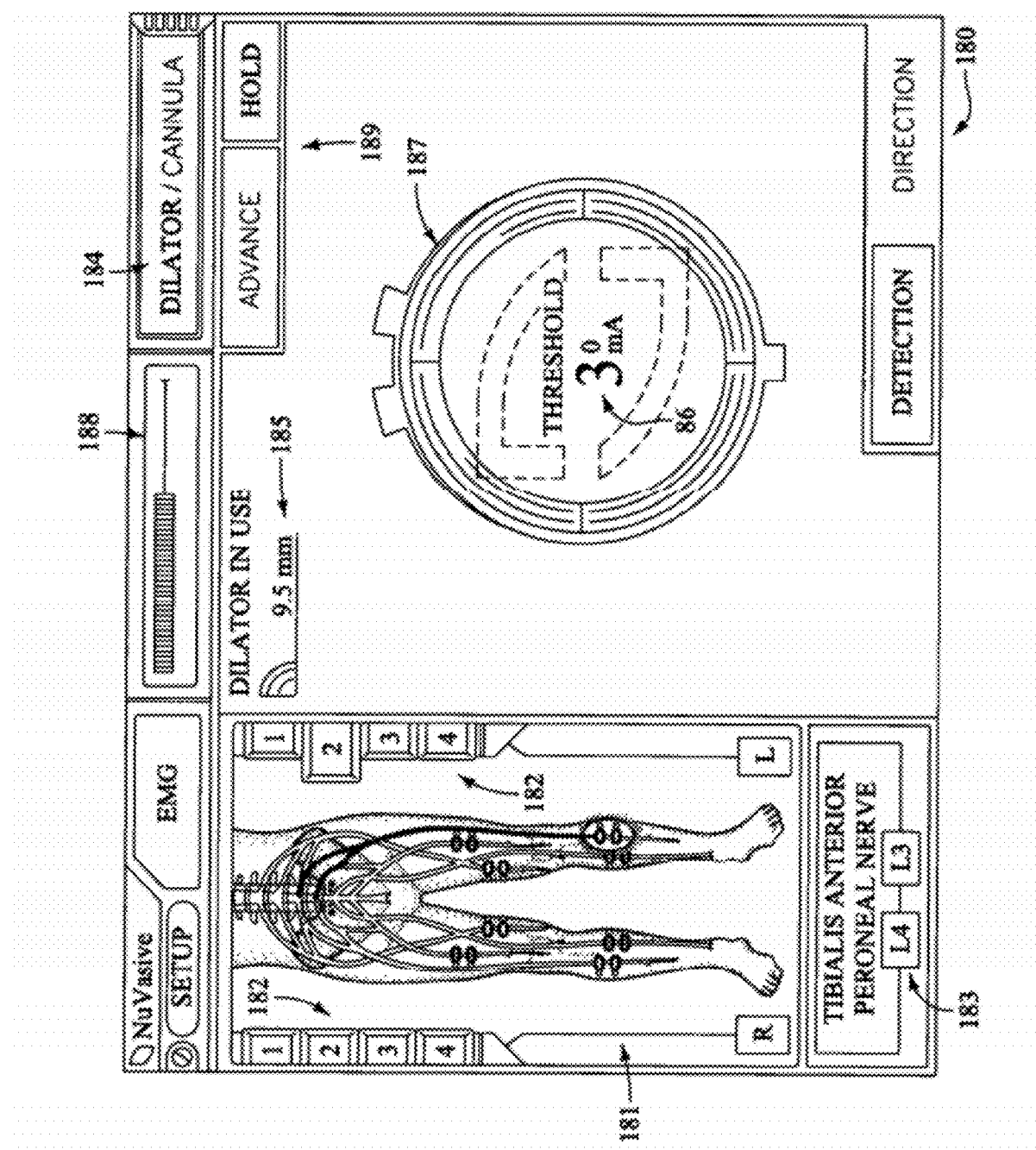
FIGS. 21-22 are screen displays illustrating exemplary features and information communicated to a user during the use of the nerve monitoring system of FIG. 19.
Figure 22:
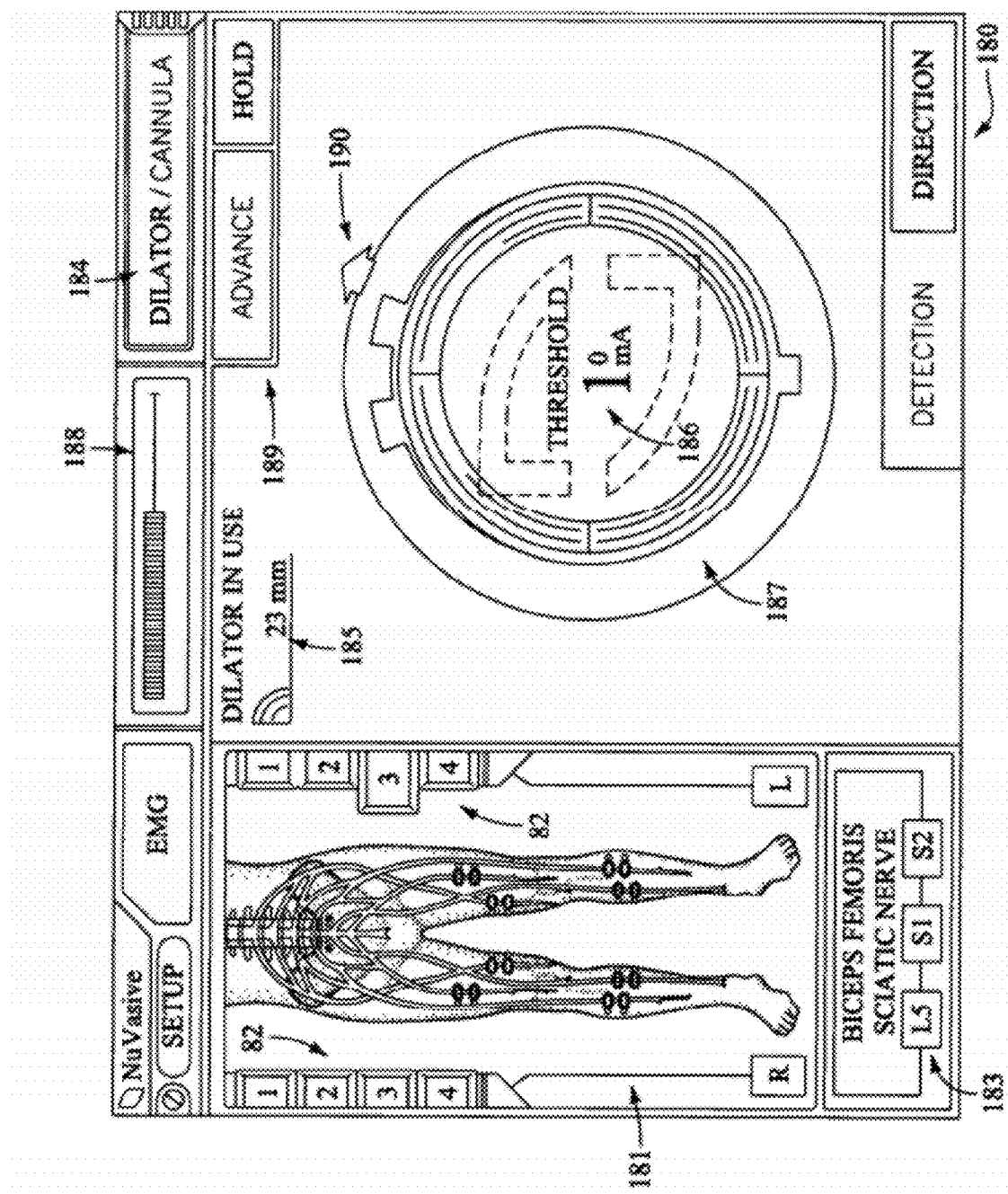

FIGS. 21-22 are exemplary screen displays (to be shown on the display 140) illustrating one embodiment of the nerve direction feature of the monitoring system shown and described with reference to FIGS. 19-20. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 44, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 22) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the initial distraction assembly 40 (i.e. the K-wire 42 and dilators 44, 48) and/or the retractor blades 12, 16, 18 and/or the shim elements 22, 24, 25.

Referring now to FIGS. 23-50, some embodiments of the surgical access system 10 may be particularly suited for establishing an operative corridor to a surgical target site in the spine. Such an operative corridor may be established through the retroperitoneal space and the psoas muscle during a direct lateral, retroperitoneal approach to the spine. A surgeon may have direct visualization of the patient's anatomy without the cumbersome requirements associated with using endoscopes or operating coaxial through narrow tubes. Moreover, when using the access system 10 through a lateral approach to the spine, the potential of damaging nerves while advancing instruments through the psoas muscle may be substantially reduced. It will, of course, be appreciated that the surgical access system and related methods of the present invention may find applicability in any of a variety of surgical and/or medical applications such that the following description relative to the direct lateral, retroperitoneal approach to the spine is not to be limiting of the overall scope of the present invention.

When accessing a spinal target site via the substantially lateral, retroperitoneal approach described in connection with FIGS. 23-50, the surgeon should consider several anatomical reference points, such as the iliac crest, the twelfth rib, and the lateral border of the erector spinae muscle groups. In certain embodiments, blunt finger dissection is used to pass between these muscle groups and access the retroperitoneal space. Such a technique offers simple access to the retroperitoneal space while minimizing the potential of visceral lesion. Furthermore, in such embodiments, the finger may be used to escort one or more dilators through the retroperitoneal space, thus reducing the potential of peritoneal disruption. In some instances, each dilator is preferably advanced through the psoas muscle between the middle and anterior third of the muscle so that the nerves of the lumbar plexus are located posterior and outside the operative corridor. A monitoring system 120 of the type disclosed in the NeuroVision PCT Applications may be used to avoid damage to any peripheral nerves embedded throughout the psoas muscle as the dilator is advanced through the muscle to the surgical target site in the spine.

Figure 23:
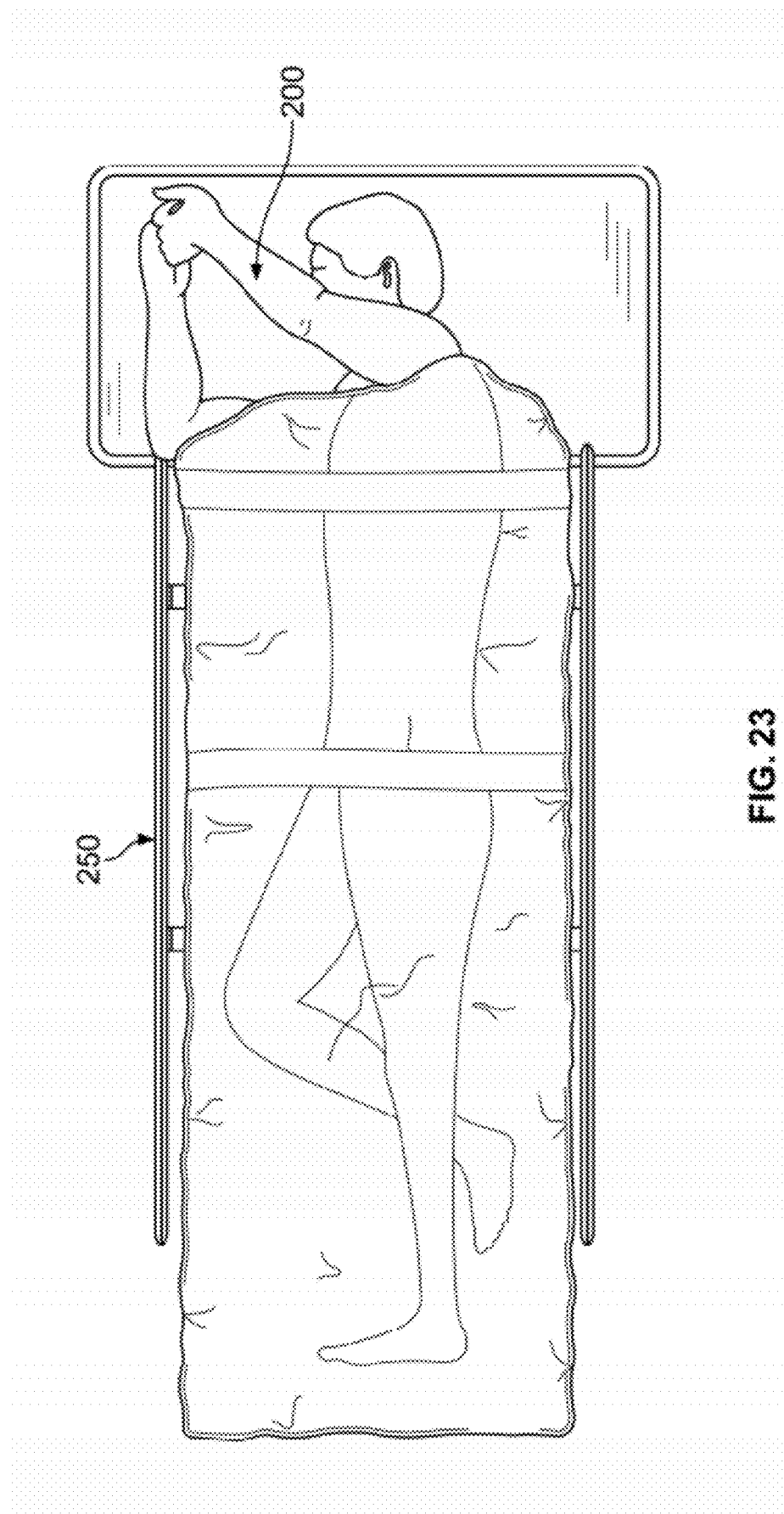
FIGS. 23-50 illustrate a method for accessing a surgical target site in the spine using a substantially lateral, retroperitoneal approach.
Figure 24:
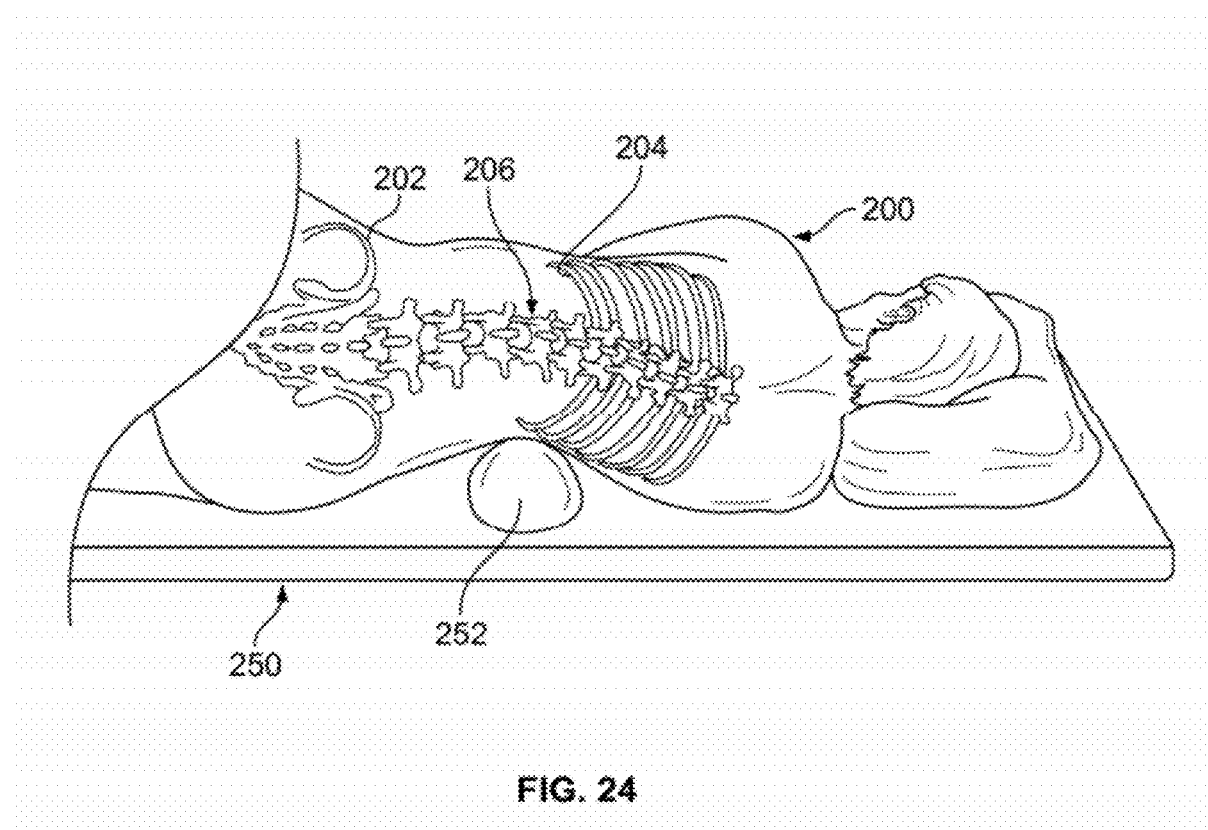

Referring now to FIGS. 23-24, a patient 200 is positioned on a surgical table 250 in preparation of spinal surgery. In some embodiments, a cushion 252 is positioned between the patient's lateral side and the surgical table 250 to arrange the patient 200 in such a way as to increase the distance between the patient's iliac crest 202 and rib cage 204. Alternatively, a flexion of the surgical table 250 may be used to accomplish the desired arrangement. Such an arrangement helps to open the invertebral disc space 206 at or near the surgical target site.

Figure 25:
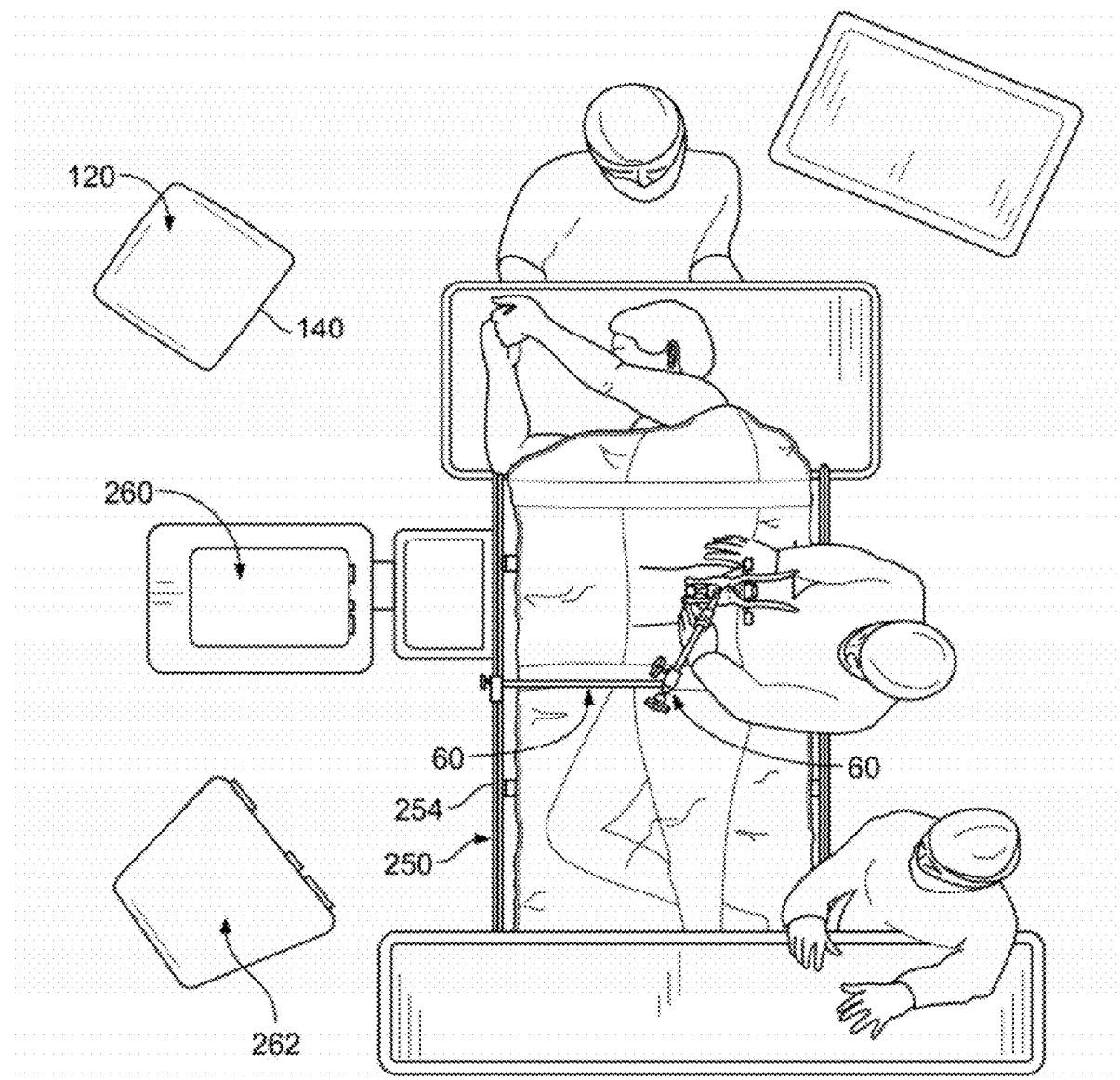

Referring to FIG. 25, an articulating arm assembly 60 is coupled to the surgical table 250 to maintain the access system 10 in a substantially fixed position relative to the surgical target site when the operative corridor has been established. In this embodiment, the articulating arm assembly 60 is mounted to a bedrail 254 of the surgical table 250. In some instances, a fluoroscopy system 260 is disposed proximal to the surgical table 250 to provide the surgeon with visualization of the surgical target area. This fluoroscopy system 260 includes a display monitor 262 that is positioned such that the surgeon may view the monitor 262 during the operation. In addition, a monitoring system 120 of the type disclosed in the NeuroVision PCT Applications may be positioned near the surgical table 250 so that the surgeon may view a display 140 of the monitoring system 120 during the operation.

Figure 26:
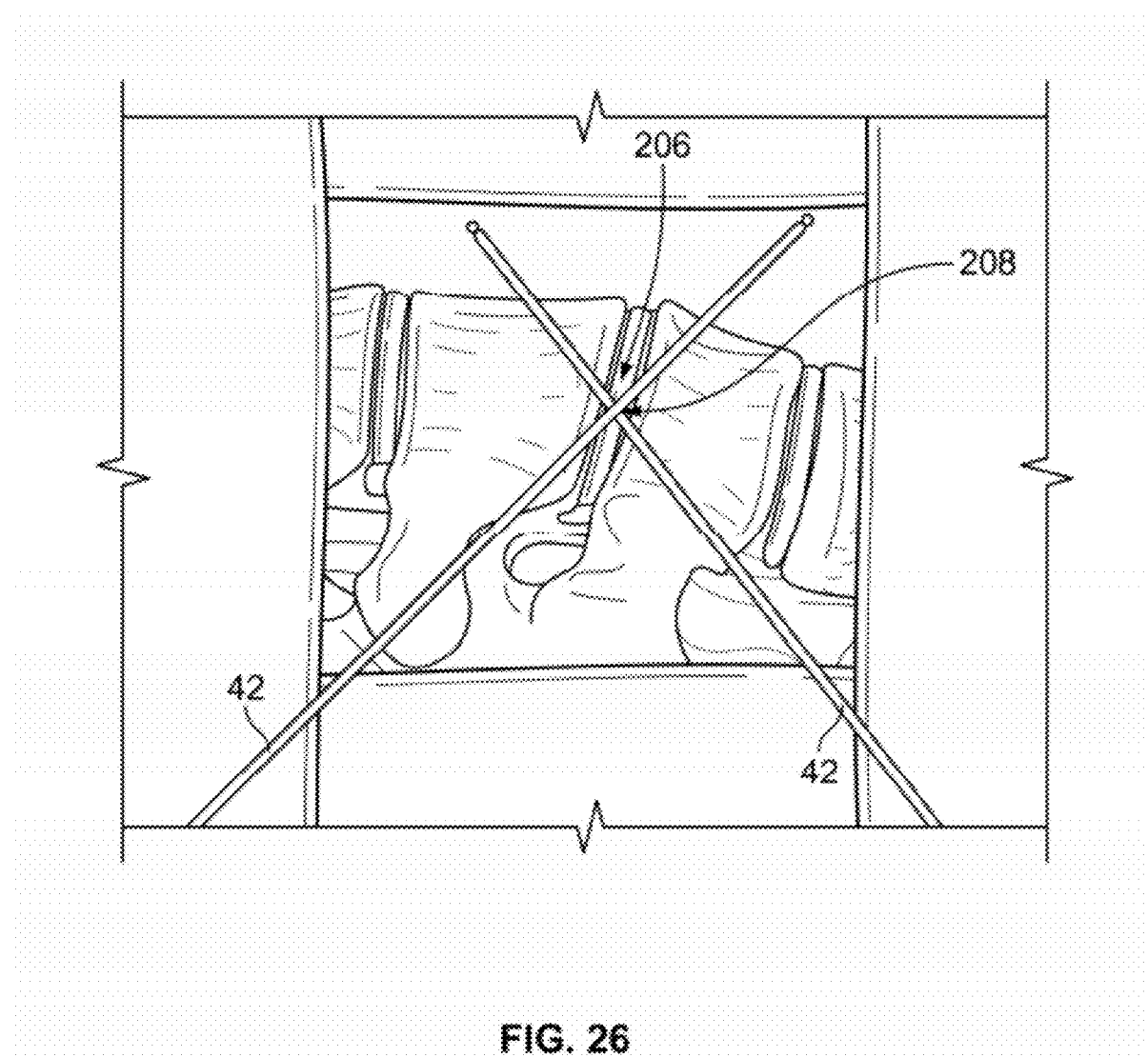
Figure 27:
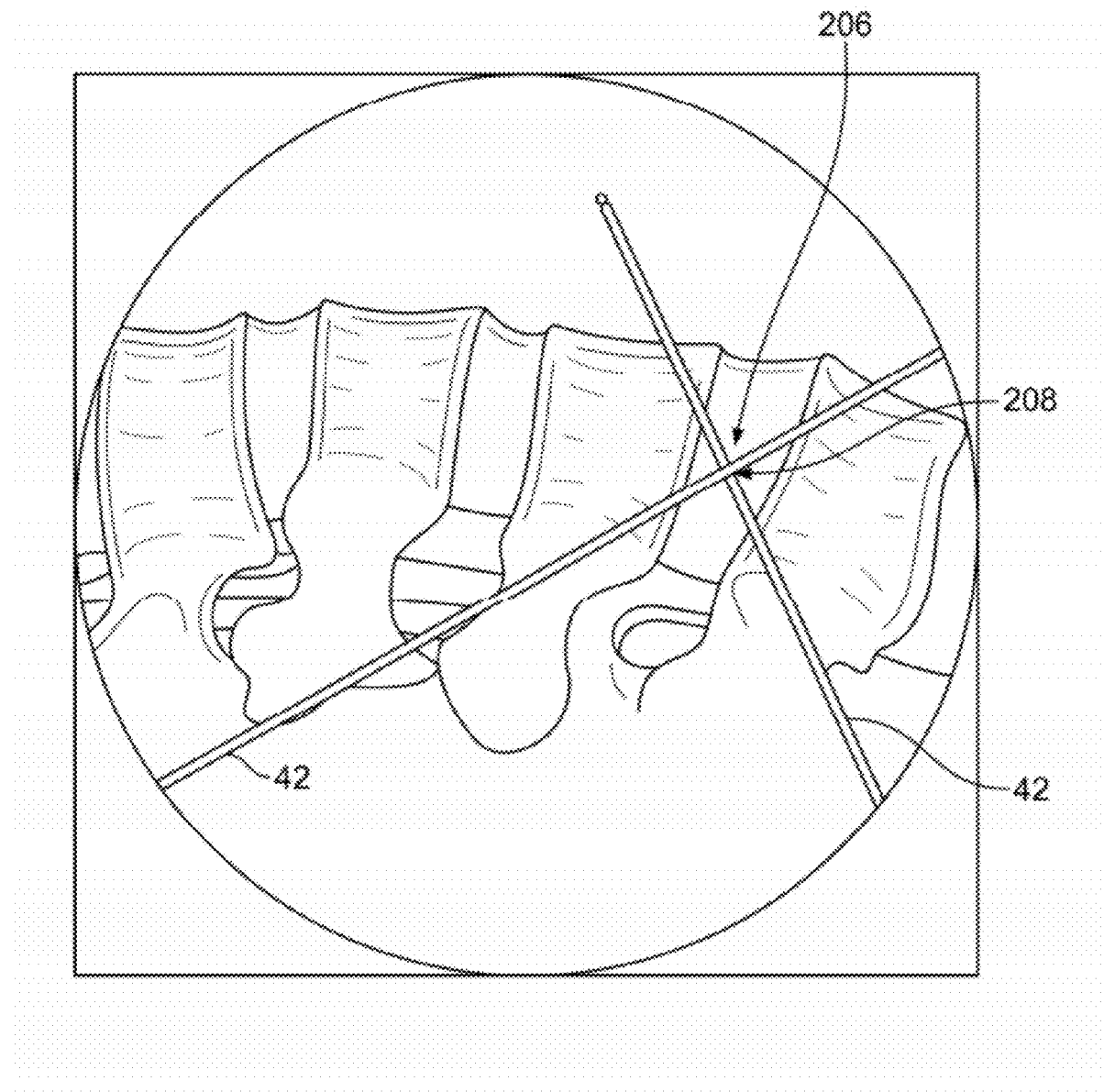
Figure 28:
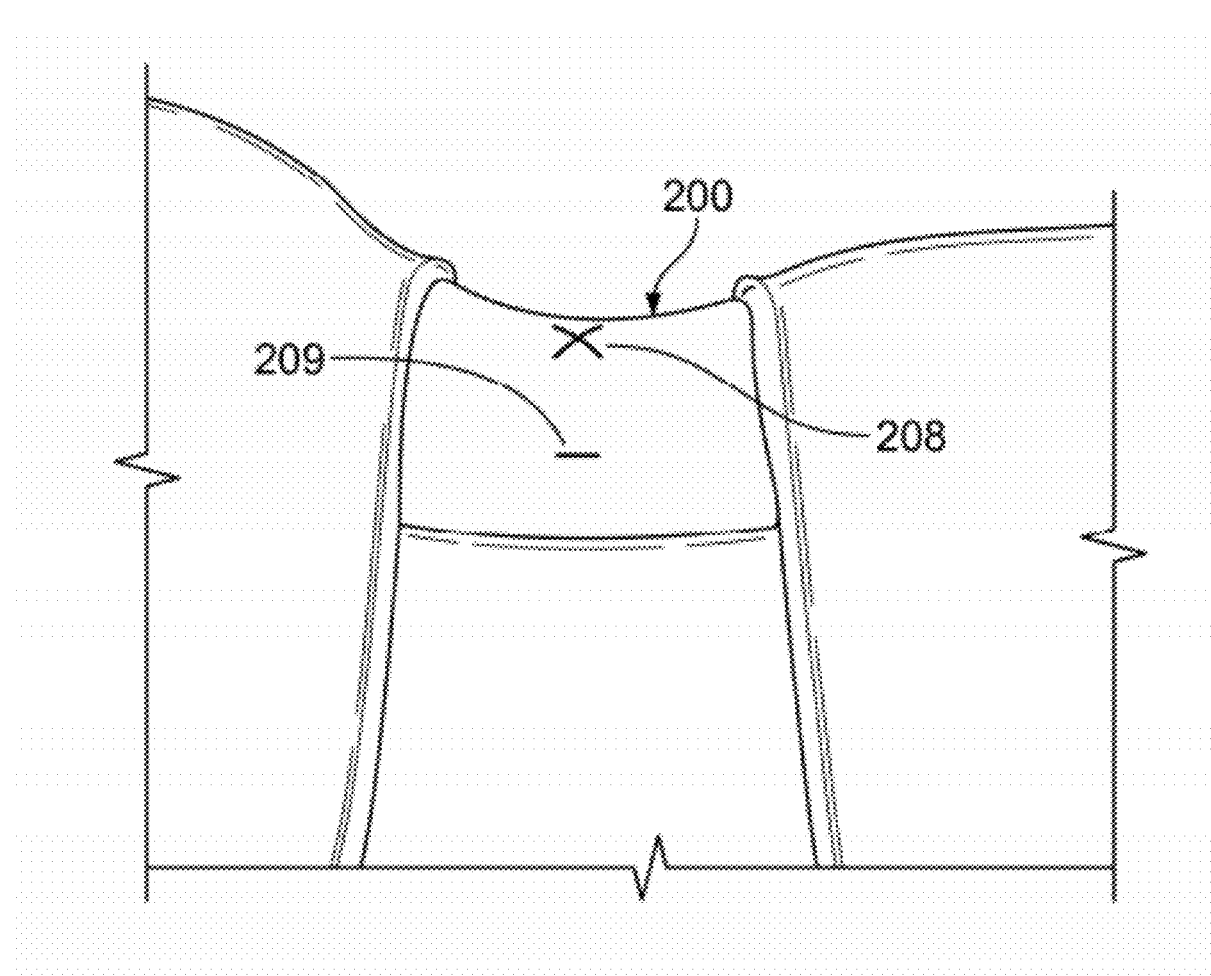

Referring now to FIGS. 26-28, one or more instruments, such as K-wires 42, are positioned laterally over an area of the patient 200 and then viewed using the lateral fluoroscopy. The instruments are used to identify a lateral incision location 208 that is substantially lateral to the surgical target site (e.g., the invertebral disc space 206). As shown in FIG. 28, a first mark is made on the patient 200 at the lateral incision location 208. In addition, a second mark is made on the patient at a posteriolateral incision location 209 near the lateral incision location 208. In this embodiment, the posteriolateral incision location 209 is approximately at the lateral border of the erector spine muscle. Preferably, the posteriolateral incision location 209 is within a finger's length of the lateral incision location 208.

Figure 29:
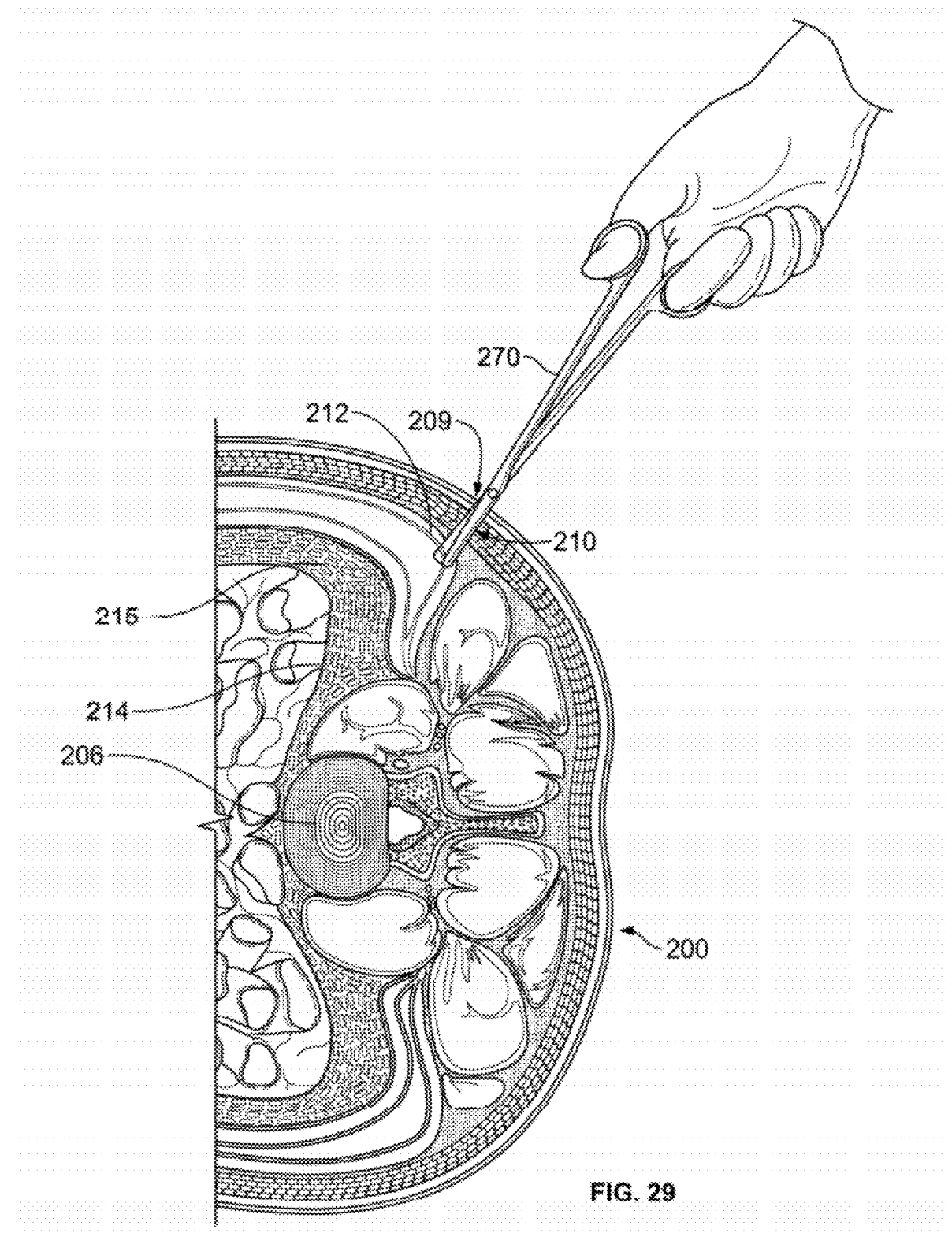

Referring to FIG. 29, an incision is made at the posteriolateral incision location 209, and the subcutaneous layers 210 are dissected until reaching the muscular masses 212. A dissection instrument, such as blunt dissection scissors 270, is used to spread the muscle fibers 212 until the retroperitoneal space 215 is reached. Preferably, the surgeon uses great caution to avoid perforation of the peritoneum 214.

Figure 30:
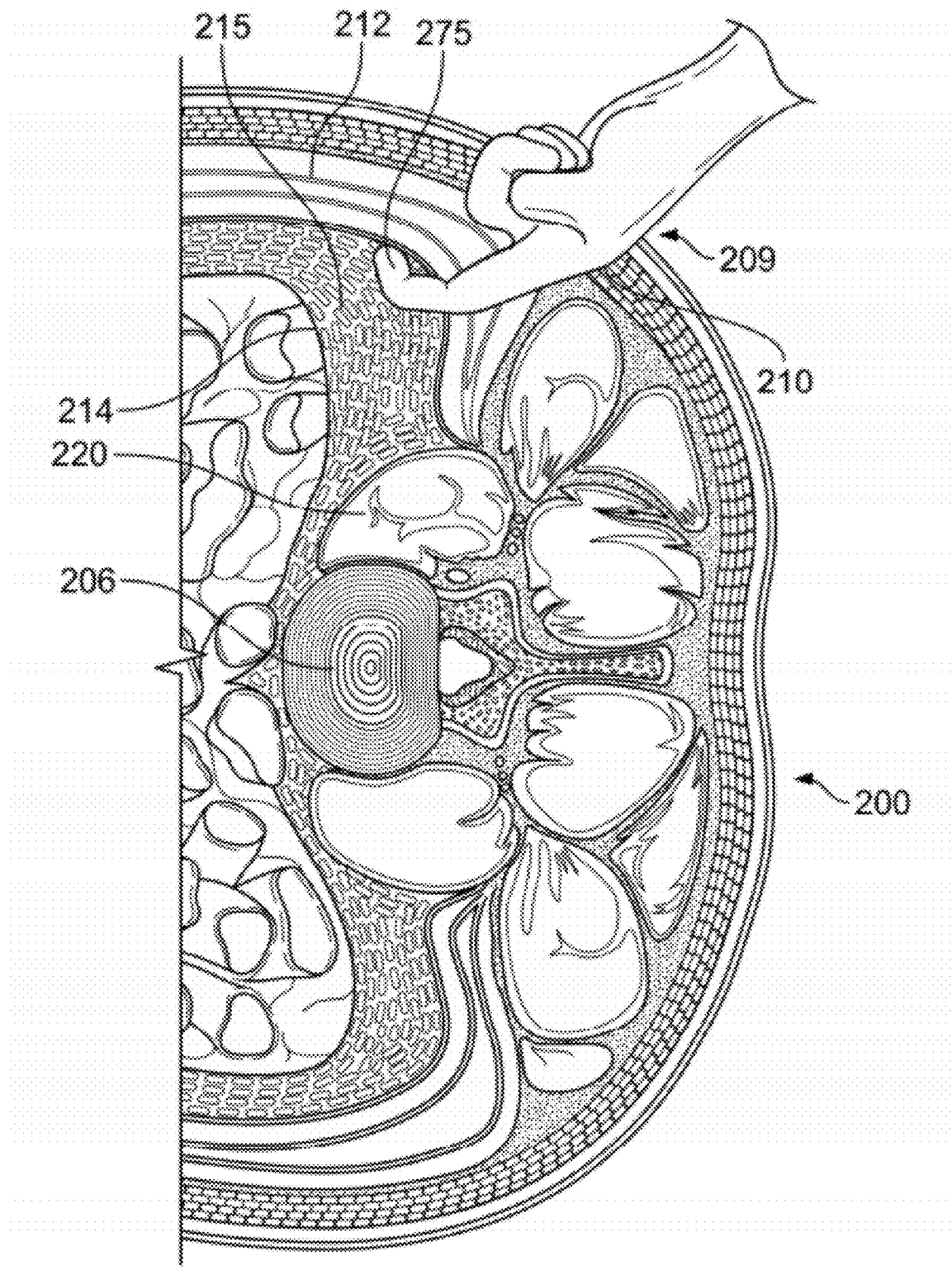
Figure 31:
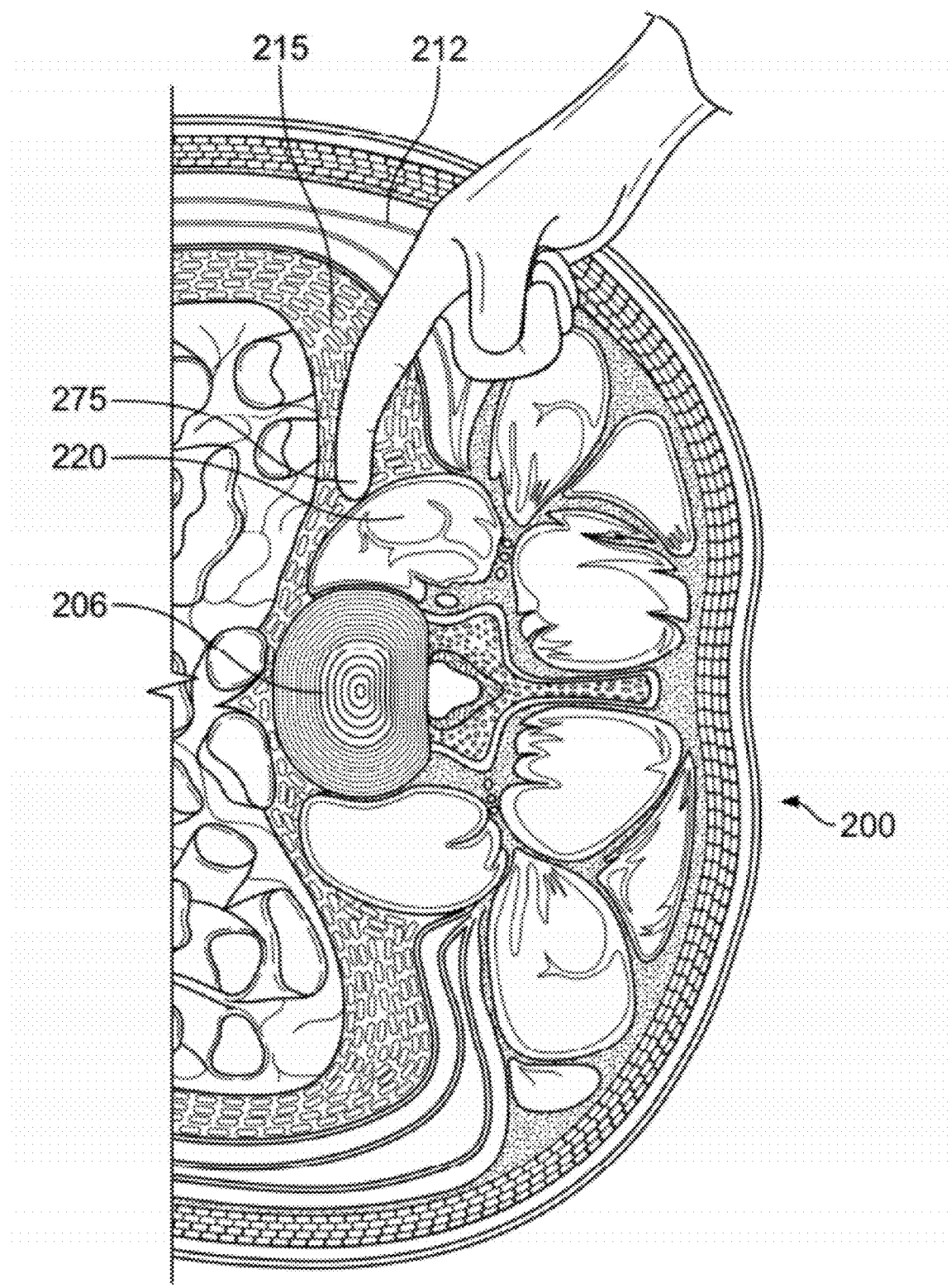

Referring to FIGS. 30-31, after the retroperitoneal space 215 is reached, a guide member 275 is inserted through the posteriolateral incision 209 into the retroperitoneal space 215. In a presently preferred embodiment, the guide member is a finger 275 of the surgeon, which is preferably covered with a surgical glove for hygienic purposes. In other embodiments, the guide member 275 may be an instrument or tool configured to extend and maneuver in the retroperitoneal space as described herein. As shown in FIGS. 30-31, the finger 275 may sweep a portion of the retroperitoneal space 215 and then palpate down to the psoas muscle 220. This motion of the finger 275 in the retroperitoneal space 215 may loosen some fatty tissue before a dilator is advanced therethrough.

Figure 32:
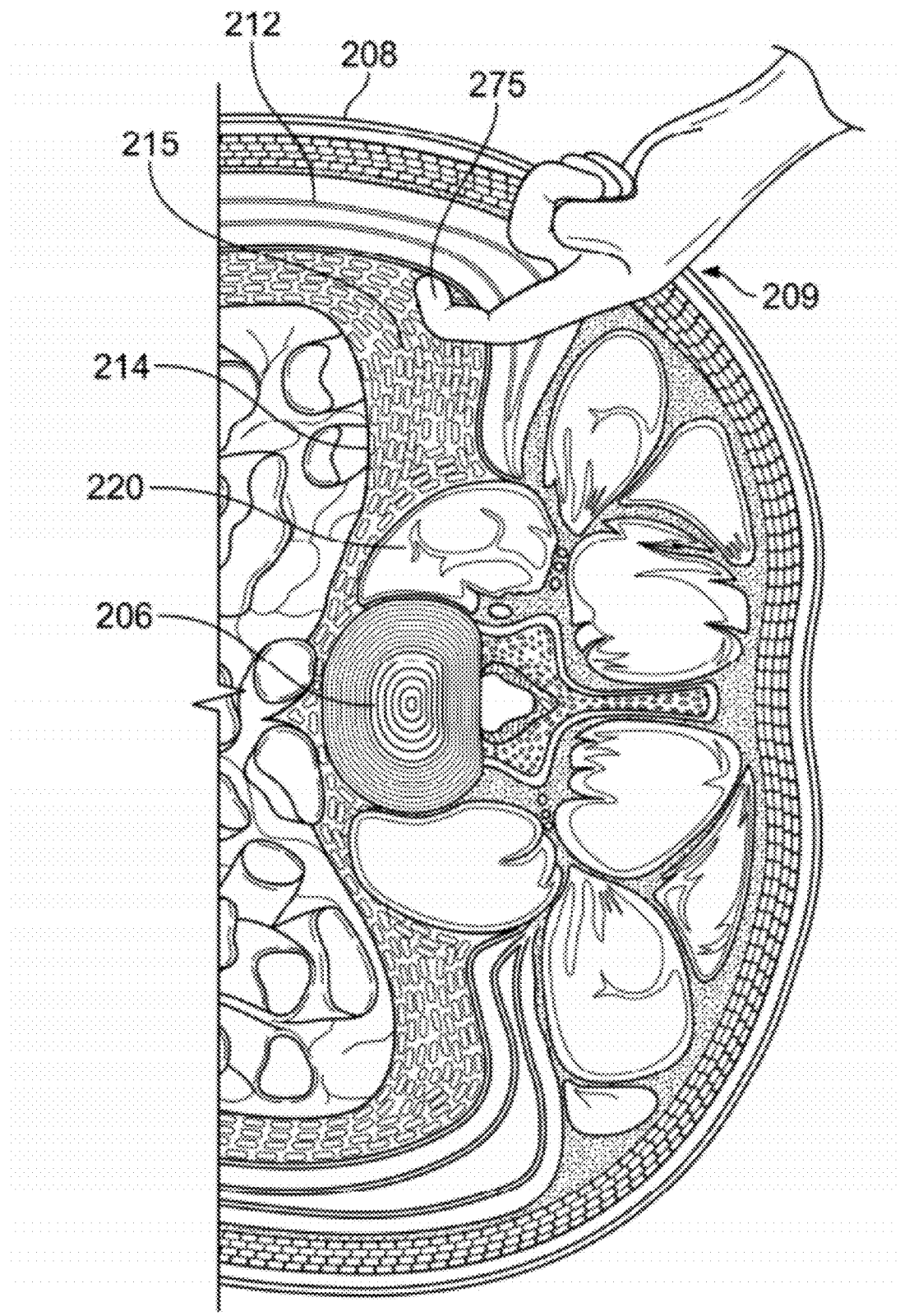
Figure 33:
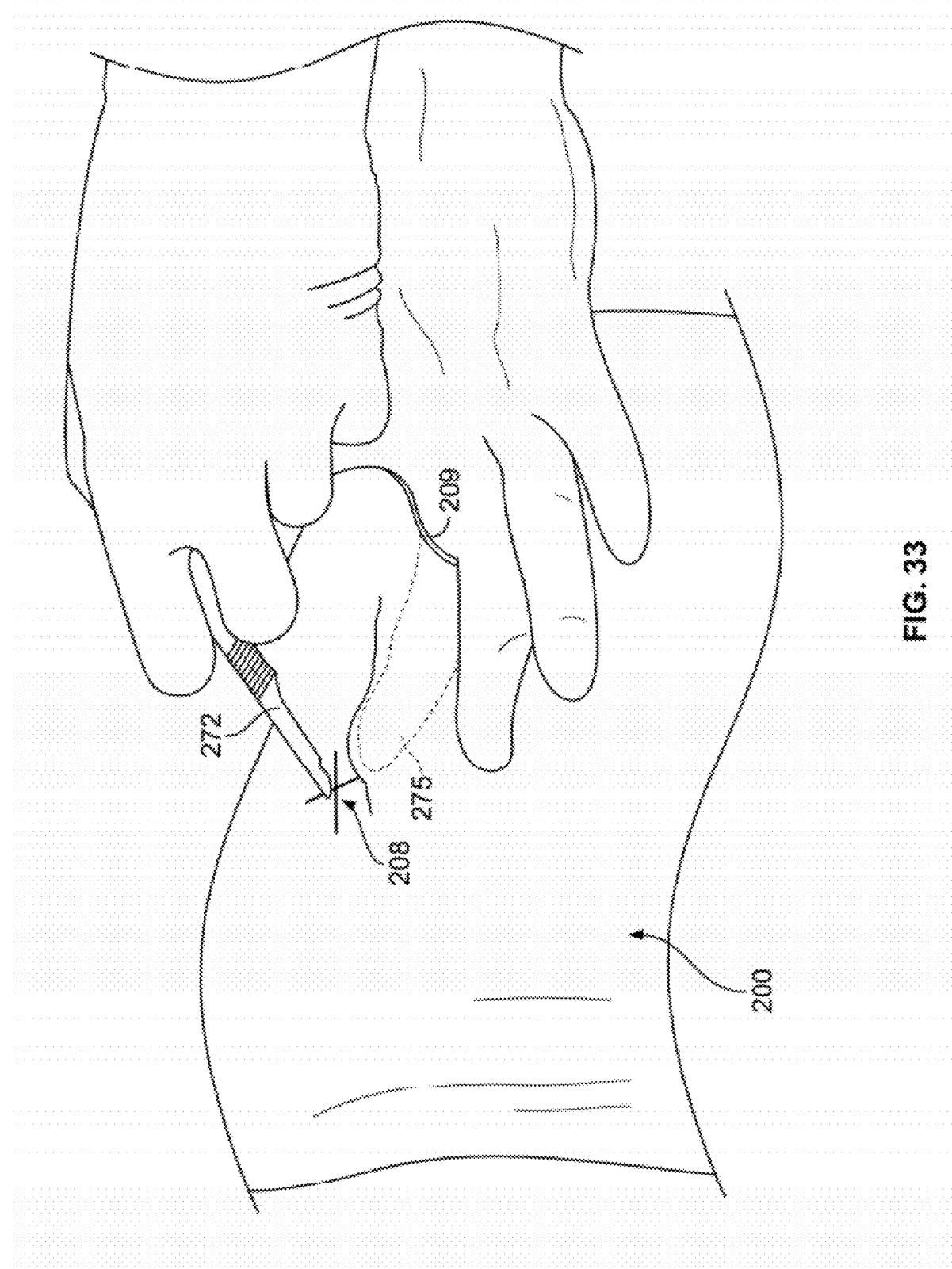

Referring to FIGS. 32-33, after the psoas muscle 220 is identified, the finger 275 is swept away from the psoas muscle 220 toward the lateral incision location 208. A scalpel 272 or other like instrument is used to make and incision at this location 208. The incision should be of a sufficient size to receive a distal end 41 an initial dilator 40.

Figure 34:
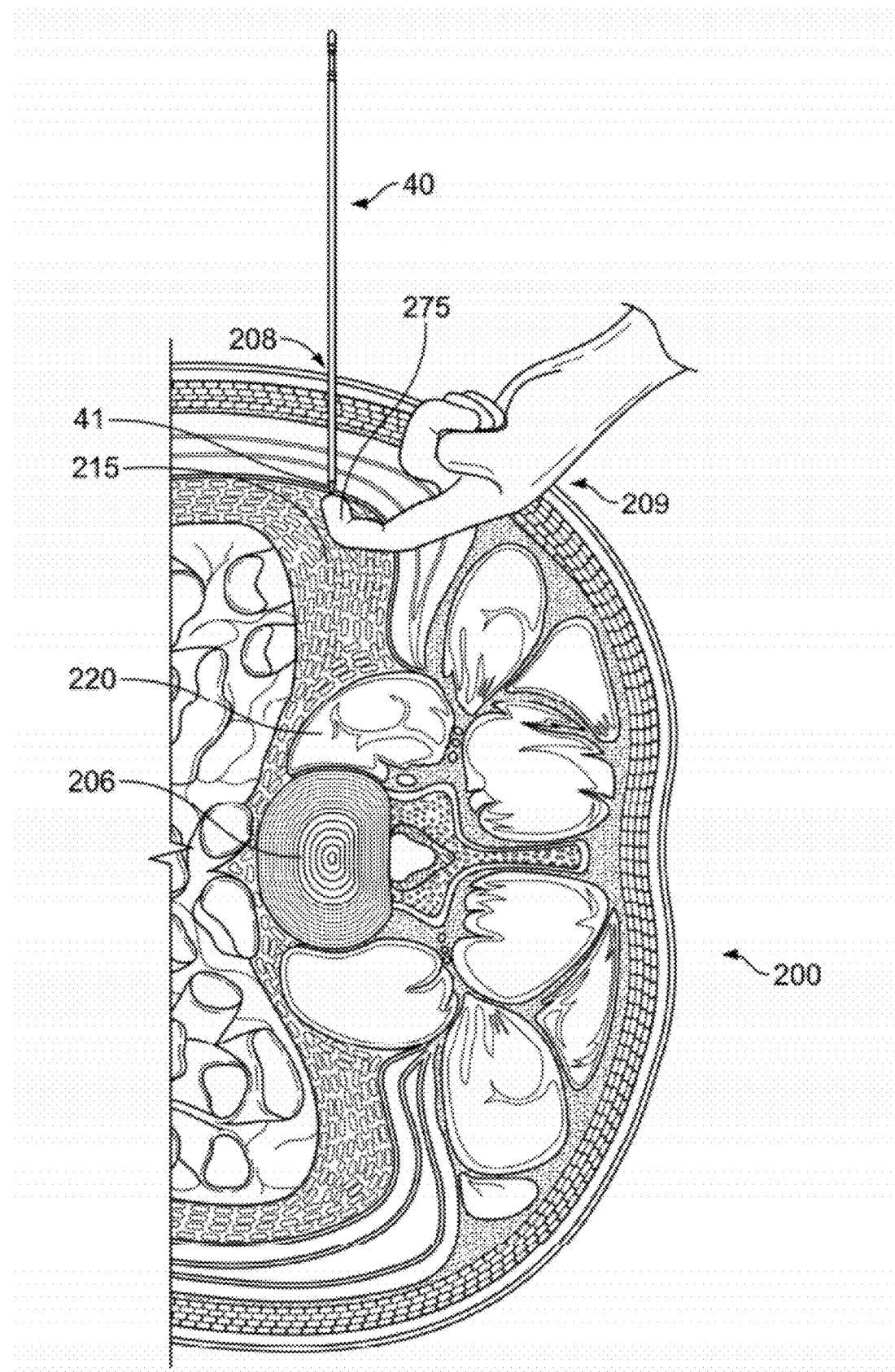
Figure 35:
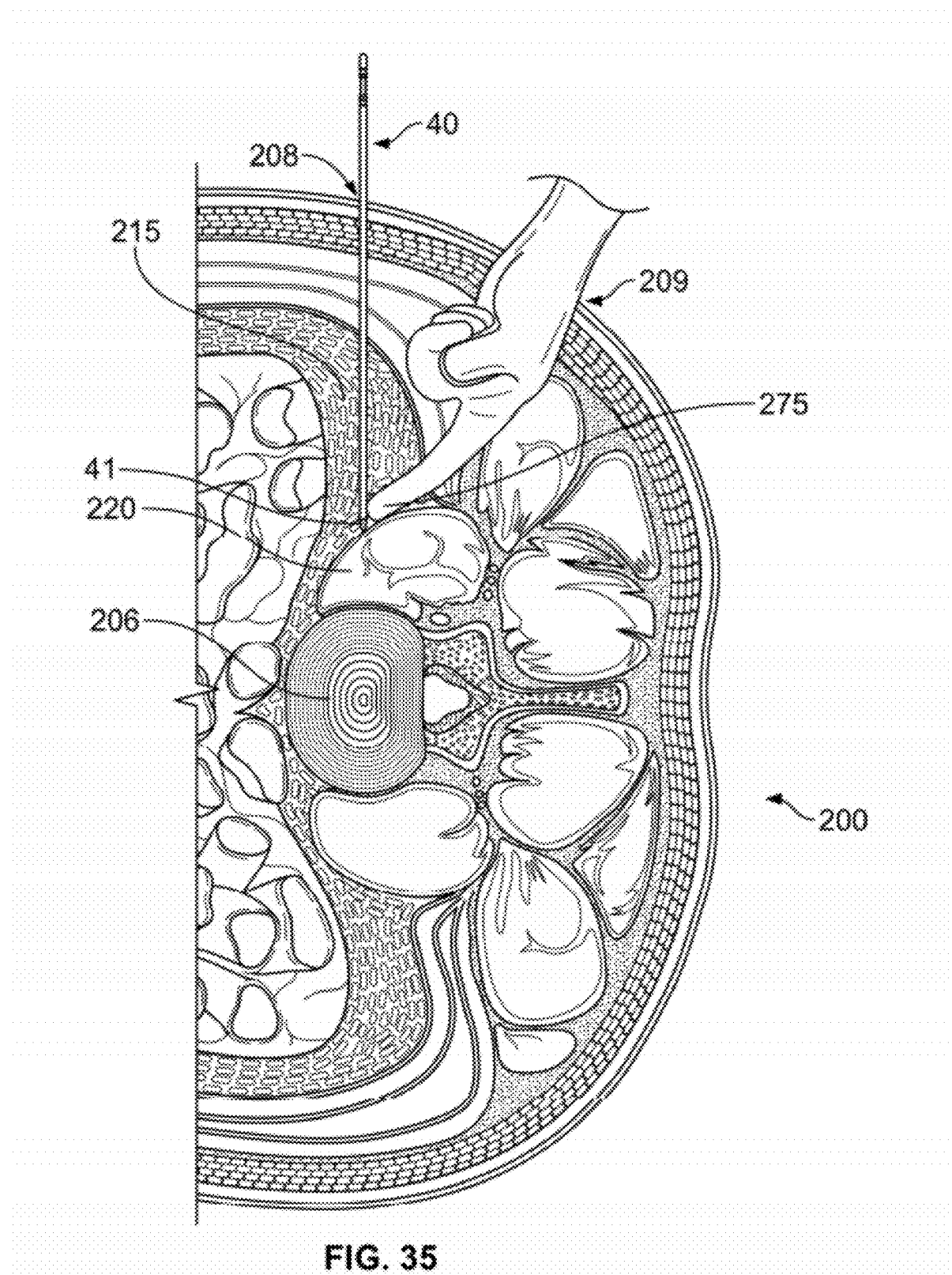

Referring to FIGS. 34-35, the finger 275 is used to direct the distal end 41 of the initial dilator 40 through the retroperitoneal space 215 toward the psoas muscle 220. In the presently preferred embodiment, the initial dilator 40 includes at least a K-wire 42 and may also include a split-dilator 48 slideably passed over the K-wire 42 (see, for example, FIG. 10). As shown in FIG. 34, the distal end 41 is introduced through the lateral incision location 208 and directed to the finger 275 in the retroperitoneal space 215. As shown in FIG. 35, the finger 275 engages the initial dilator 40 proximal to the distal end 41 and guides the distal end 41 to the psoas muscle 220. By escorting the dilator 40 through the retroperitoneal space 215 using the finger 275, the potential for breaching or disrupting the peritoneal is reduced. Upon reaching the psoas muscle 220, the location of the distal end 41 relative to the target site may be verified using an imaging system, such as an image intensifier.

Figure 36:
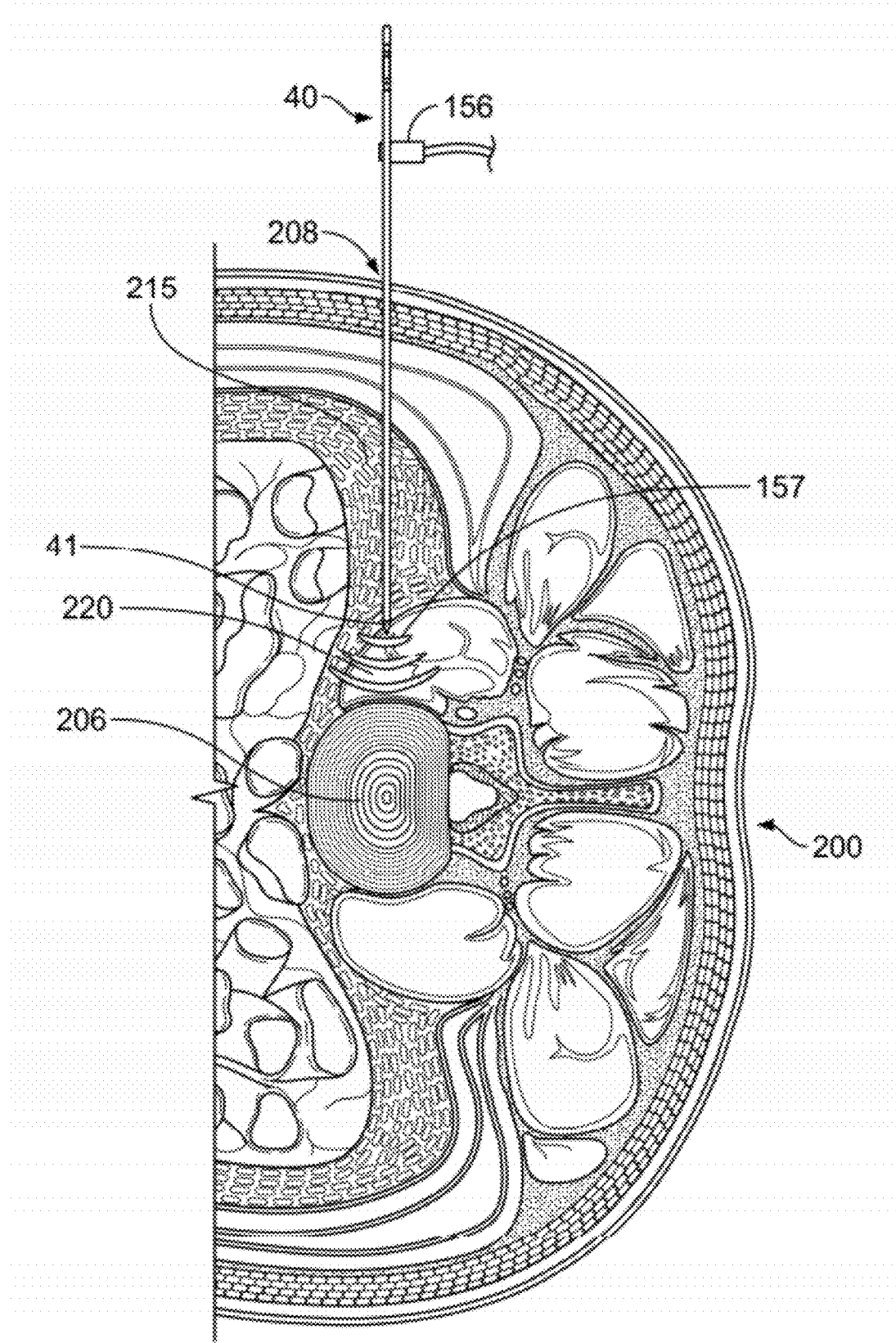
Figure 37:
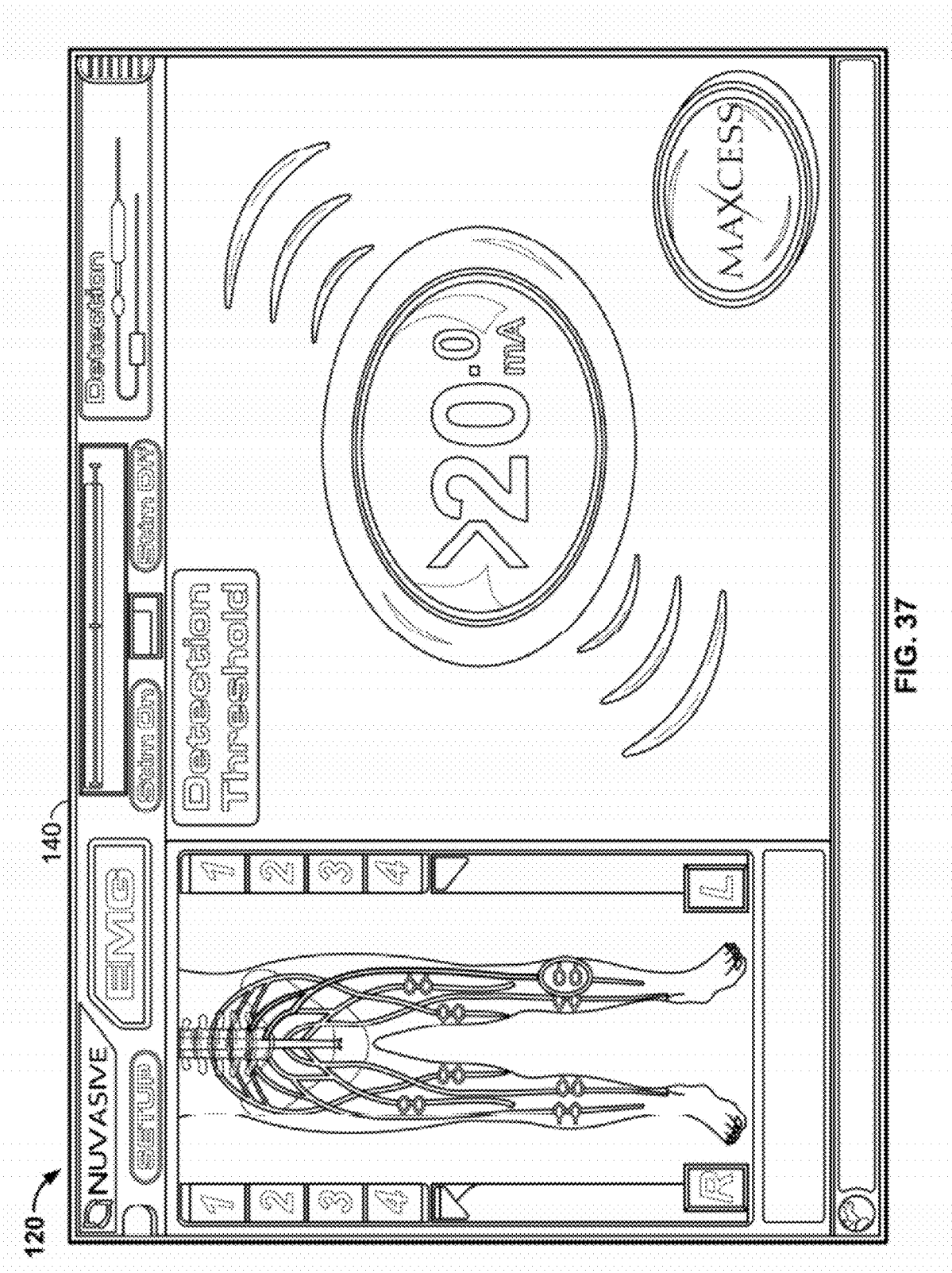

Referring to FIGS. 36-37, the distal end 41 of the initial dilator 40 is advanced in a substantially lateral direction through the psoas muscle 220 toward the invertebral disc space 206 at or near the surgical target site. In the presently preferred embodiment, the fibers of the psoas muscle 220 are split using blunt dissection and NeuroVision neurophysiologic monitoring of the type disclosed in the NeuroVision PCT Applications. A stimulation connector 156 of the NeuroVision monitoring system 120 (see FIG. 19) is coupled to the initial dilator 40 to provide a stimulation signal 157 as the dilator 40 is advanced through the psoas muscle 220. It should be understood that the stimulation signal 157 is depicted in FIG. 36 for illustrative purposes and is generally not visible.

Descending nerves of the lumbar plexus normally lie in the posterior one-third of the psoas muscle 220. The NeuroVision monitoring system 120 of the type disclosed in the NeuroVision PCT Applications assists with the safe passage by these nerves and/or confirmation of the nerves' posterior location. The NeuroVision monitoring system 120 will continuously search for the stimulus threshold that elicits an EMG response on the myotomes monitored and then reports such thresholds on a display 140 as shown in FIG. 37. As the dilator is advanced through the psoas muscle 220, the stimulus necessary to elicit an EMG response will vary with distance from the nerve. In the presently preferred embodiment, experience has shown that threshold values greater than 10 mA indicate a distance that allows for safe passage through the psoas muscle 220 and continued nerve safety.

Figure 38:
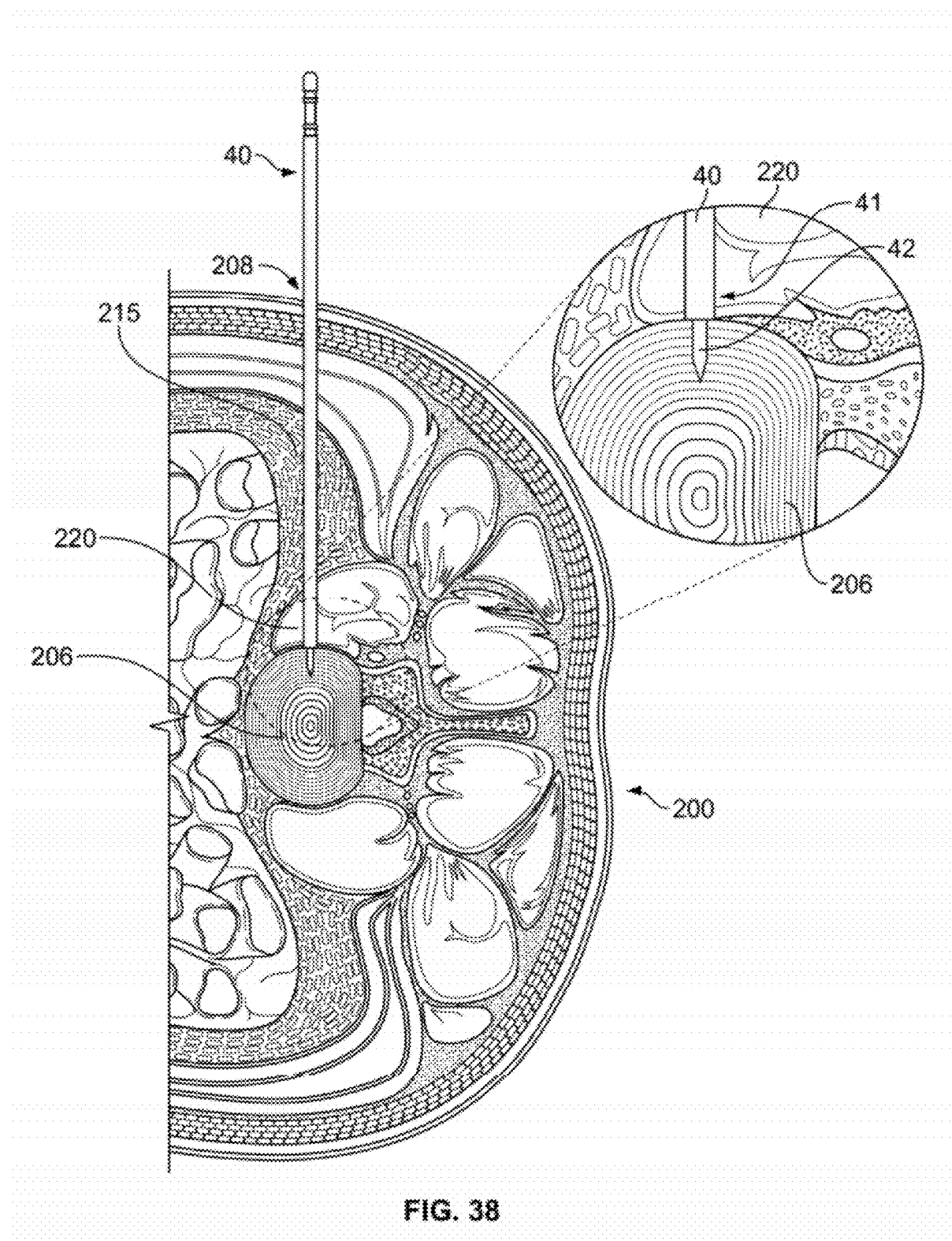
Figure 39:
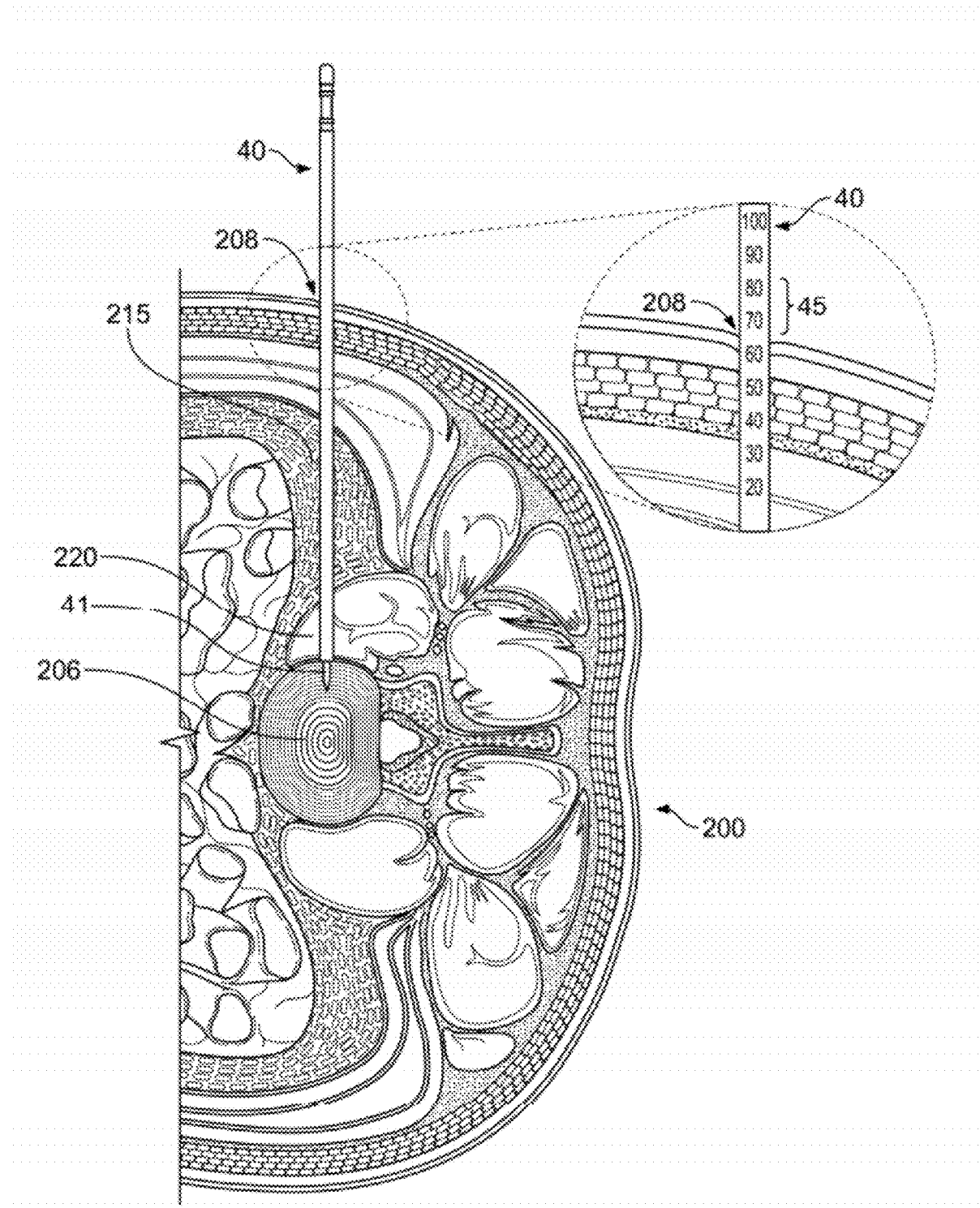
Figure 40:
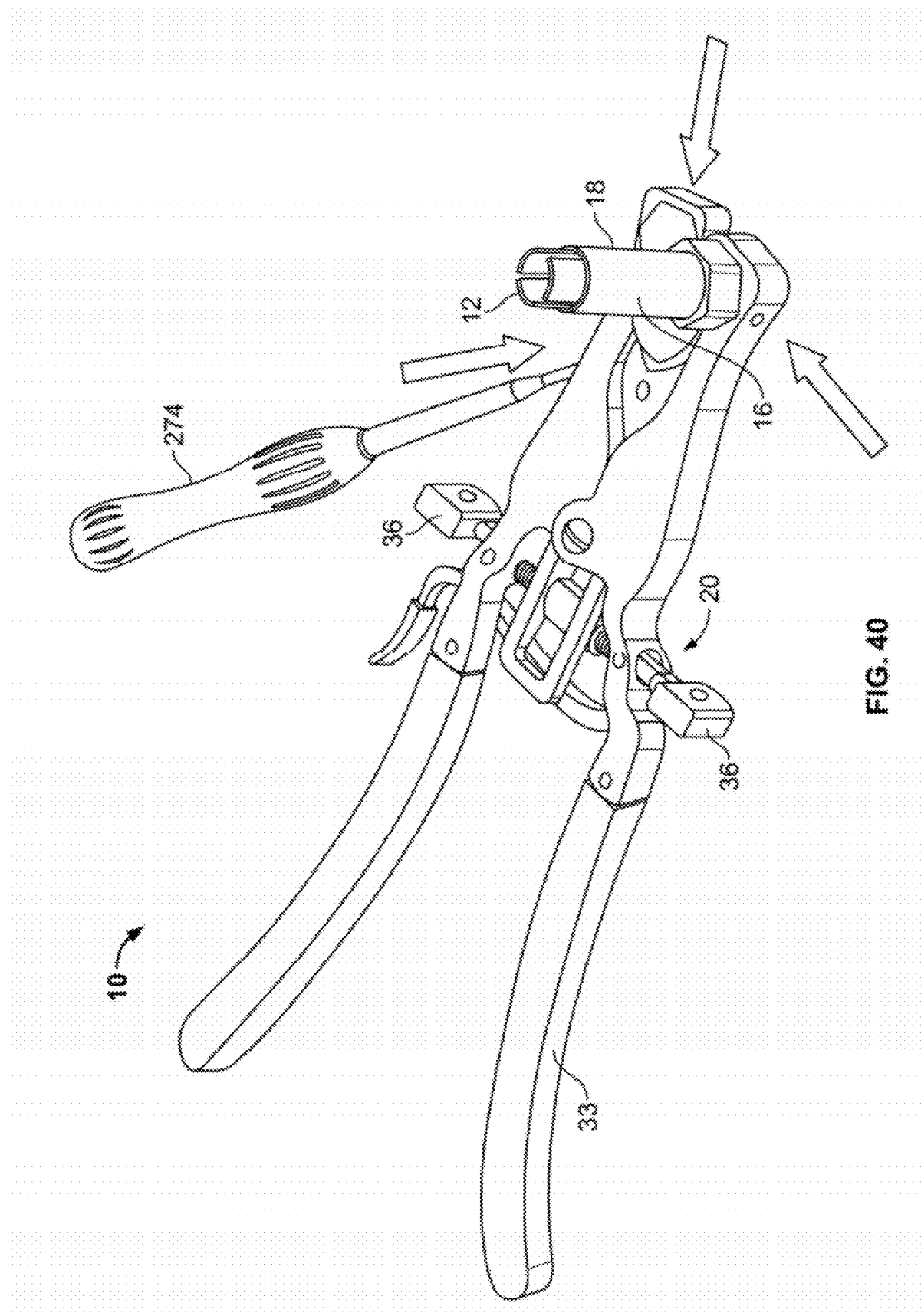

Referring to FIGS. 38-40, a K-wire 42 of the initial dilator 40 is introduced into the targeted disc space 206 after the dilator 40 is passed through the psoas muscle 220. Preferably, the position of the distal end 41 of the dilator 40 is confirmed using fluoroscopic imaging before the K-wire 42 is introduced into the disc space 206. After a distal portion of the K-wire 42 is inserted into the targeted disc space 206, depth markings 45 (FIG. 39) on the dilator 40 may be read at the skin level to determine the appropriate length of retractor blades 12, 16, 18 that will be used with the handle assembly 20 of the access system 10. As shown in FIG. 40, the appropriate length blades 12, 16, and 18 may be secured to the handle portion 20 by tightening fasteners with a driver instrument 274.

Figure 41:
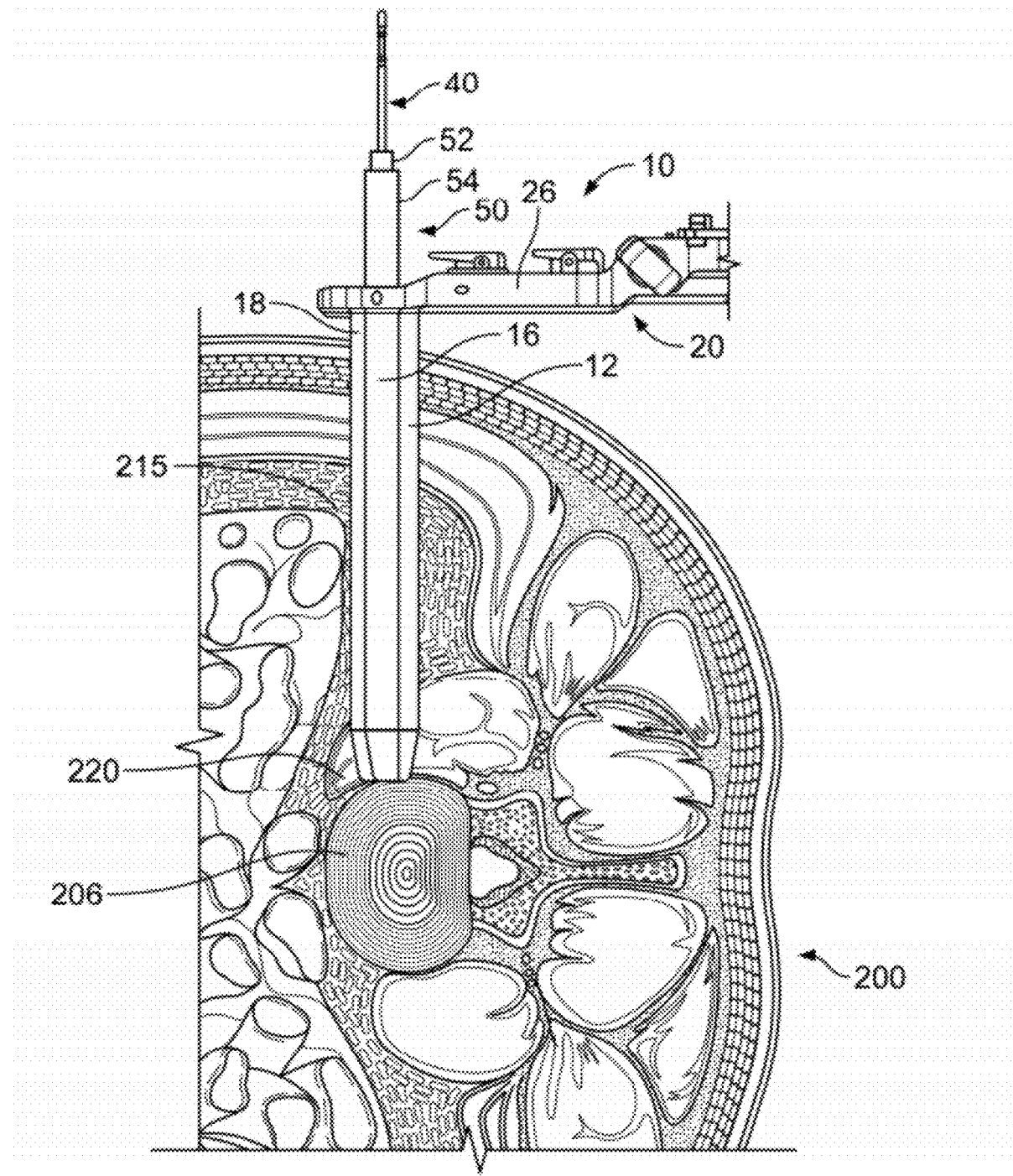

Referring to FIG. 41, the sequential dilation system 50 (previously described in connection with FIG. 12), including one or more supplemental dilators 52, 54, may be guided over the initial dilator 40 for the purpose of further dilating the tissue down to the surgical target site. In the presently preferred embodiment, the NeuroVision monitoring system 120 of the type disclosed in the NeuroVision PCT Applications is used with the supplemental dilators 52, 54 to provide safe passage through the psoas muscle 220. The initial dilator 40 and the supplemental dilators 52, 54 are advanced through the lateral incision location 208 to the targeted disc space 206 in a substantially lateral direction to create a distraction corridor.

Still referring to FIG. 41, the refractor blades 12, 16, 18 of the access system 10 are introduced over the supplemental dilator 54 (or the initial dilator 40 if the sequential dilation system 50 is not employed) toward the disc space 206. Again, the NeuroVision monitoring system 120 of the type disclosed in the NeuroVision PCT Applications may be used with the blades 12, 16, 18 to provide safe passage through the psoas muscle 220. In some embodiments, the posterior shim element 22 and/or the retractor extenders 24, 25 are engaged with the retractor blades 12, 16, 18 (as previously described in connection with FIGS. 1-7). After the retractor blades 12, 16, 18 are introduced along the distraction corridor, fluoroscopic imaging may be used to confirm the position of the blades 12, 16, 18 proximal to the disc space 206.

Figure 42:
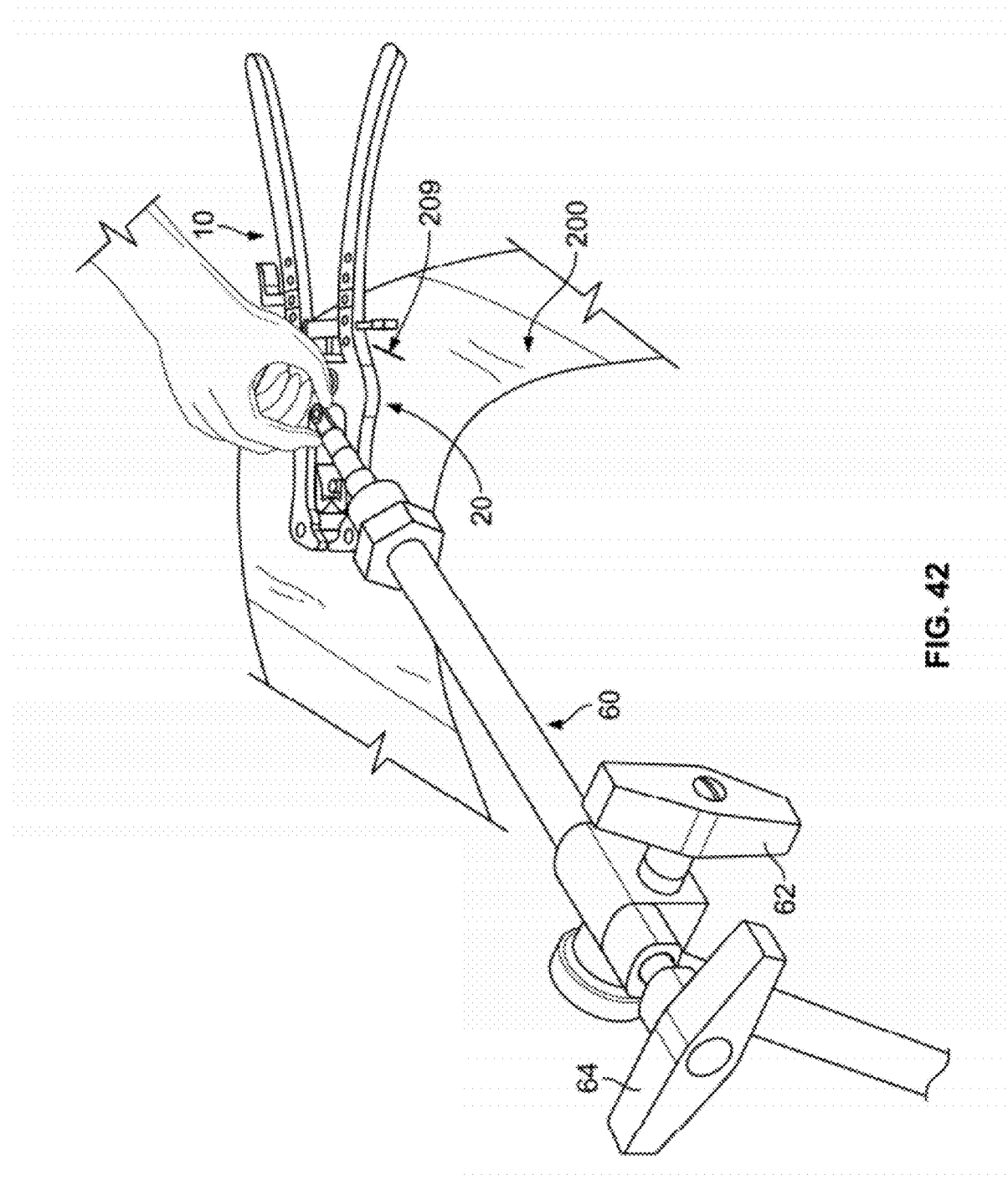

Referring to FIG. 42, the articulating arm assembly 60 is coupled to the handle member 20 of the access system 10. As previous described in connection with FIG. 25, the articulating arm assembly 60 is also coupled to the surgical table 250 so as to maintain the access system 10 in a substantially fixed position. Handles 62 and 64 may be turned to substantially fix the position of articulating arm assembly 60.

Figure 43:
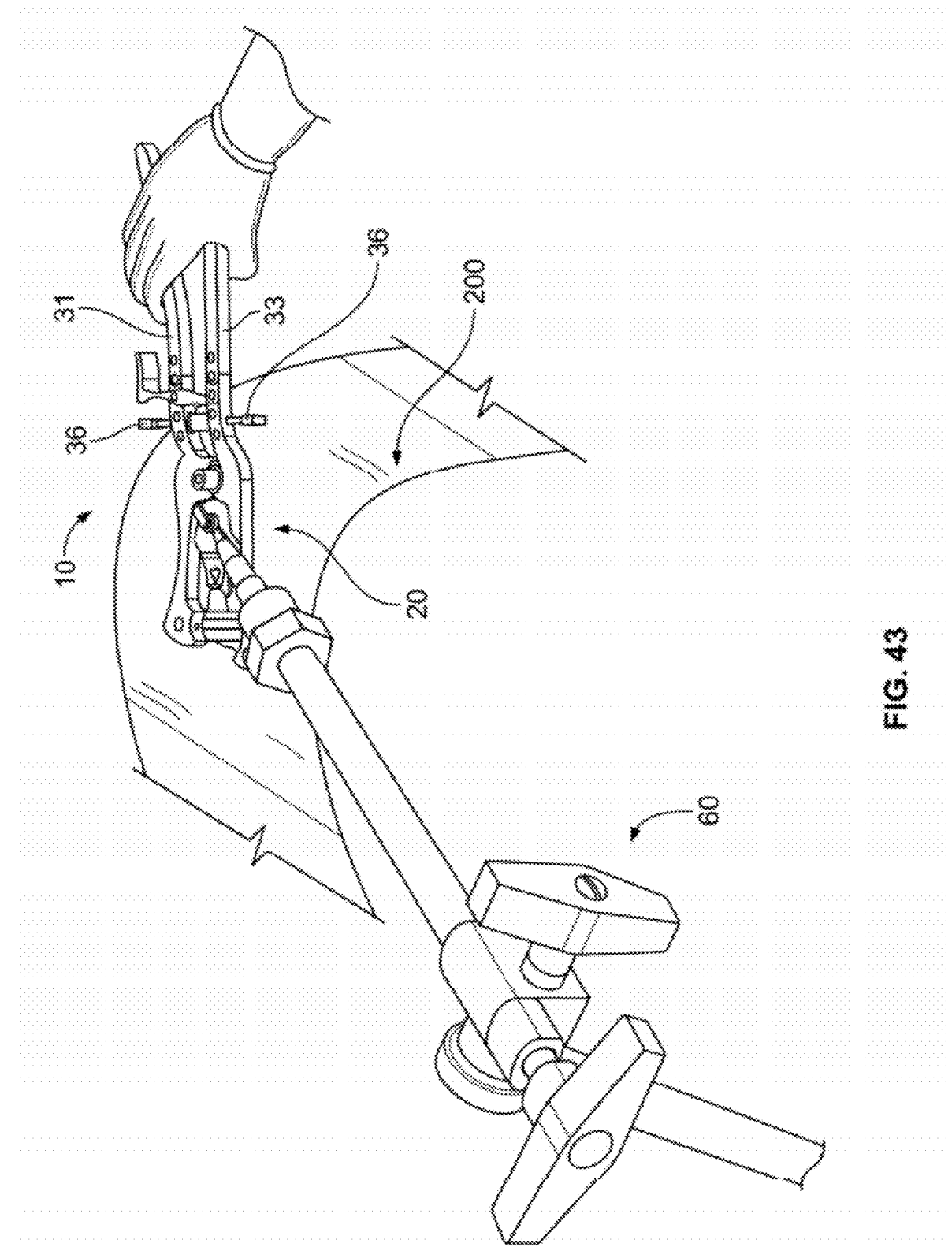
Figure 44:
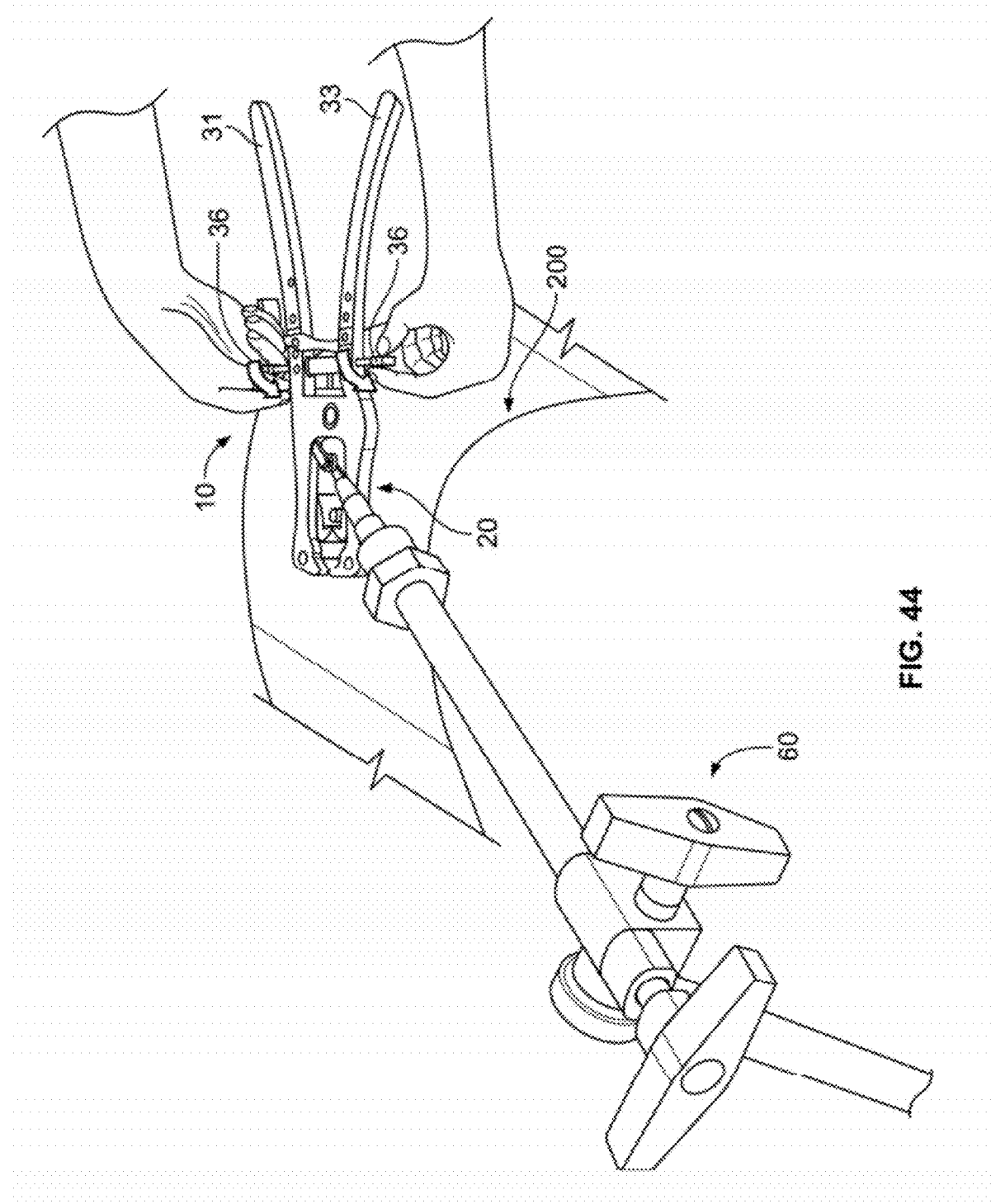

Referring now to FIGS. 43-44, handle extenders 31 and 33 may be squeeze to spread the blades 12, 16, 18 and knob members 36 may be turned to selectively adjust the posterior retractor blade 12 (previously described in connection with FIGS. 13-18). Such movement by the blades 12, 16, 18 retracts the distraction corridor so as to form an operative corridor 15.

Figure 45:
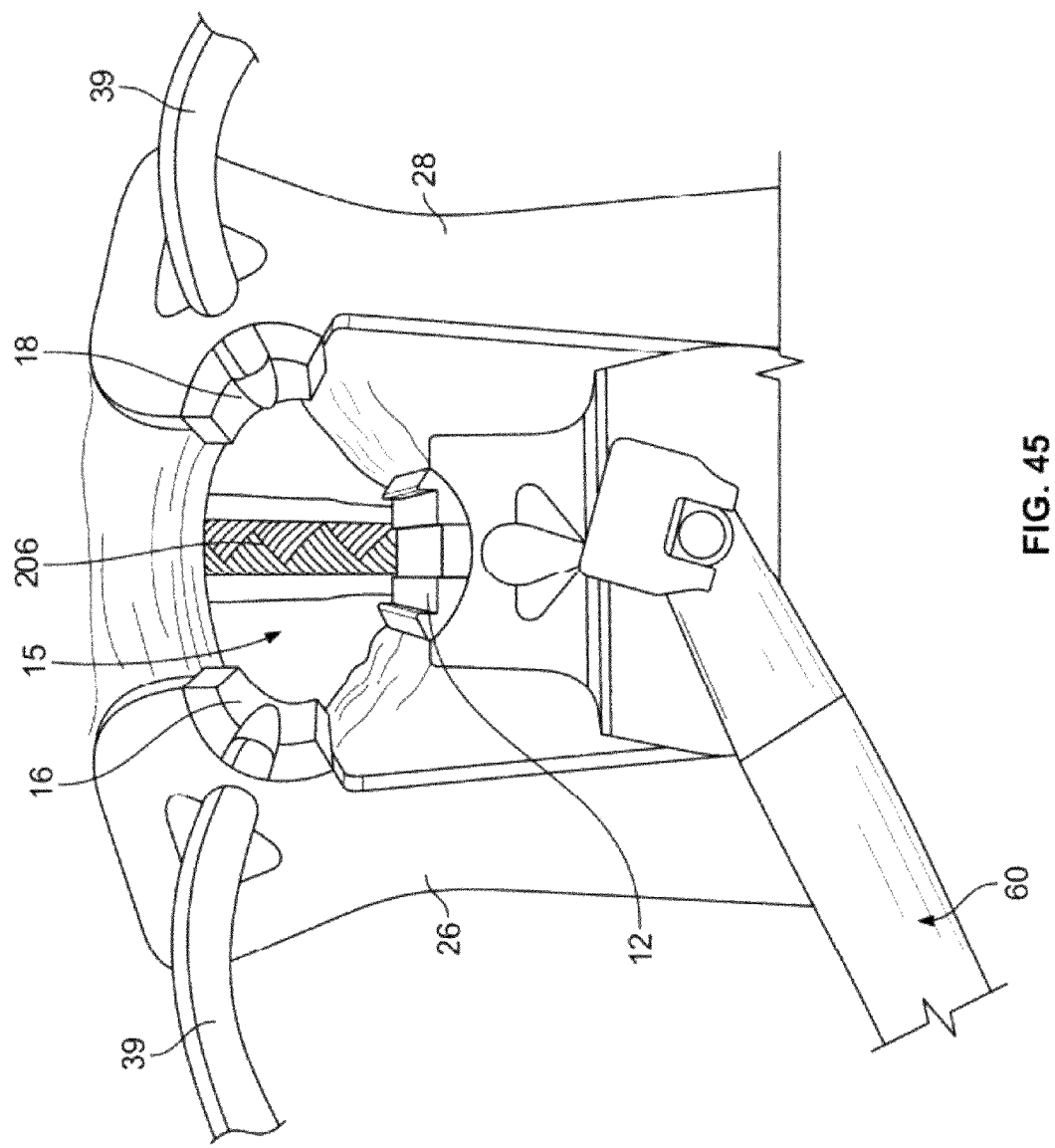

FIG. 45 shows a lateral view of the operative corridor 15 down to the targeted disc space 206 in the patient's spine. Light emitting devices 39 may be coupled to one or more of the retractor blades 12, 16, 18 to direct light down the operative corridor 15. In this embodiment, the light emitting devices 39 are coupled to a xenon arthroscopy light source. The surgeon may use direct visualization and/or a NeuroVision probe of the type disclosed in the NeuroVision PCT Applications to confirm that the operative corridor 15 is neurologically clear.

Referring to FIGS. 46-50, various instruments may be inserted through the operative corridor 15 to prepare the targeted disc space 206. In the presently preferred embodiment, the operative corridor 15 has a 15-20 mm annulotomy to provide ample space for the various instruments. In other embodiments, the operative corridor 15 may have other configurations, depending on the surgical task to be performed.

Figure 46:
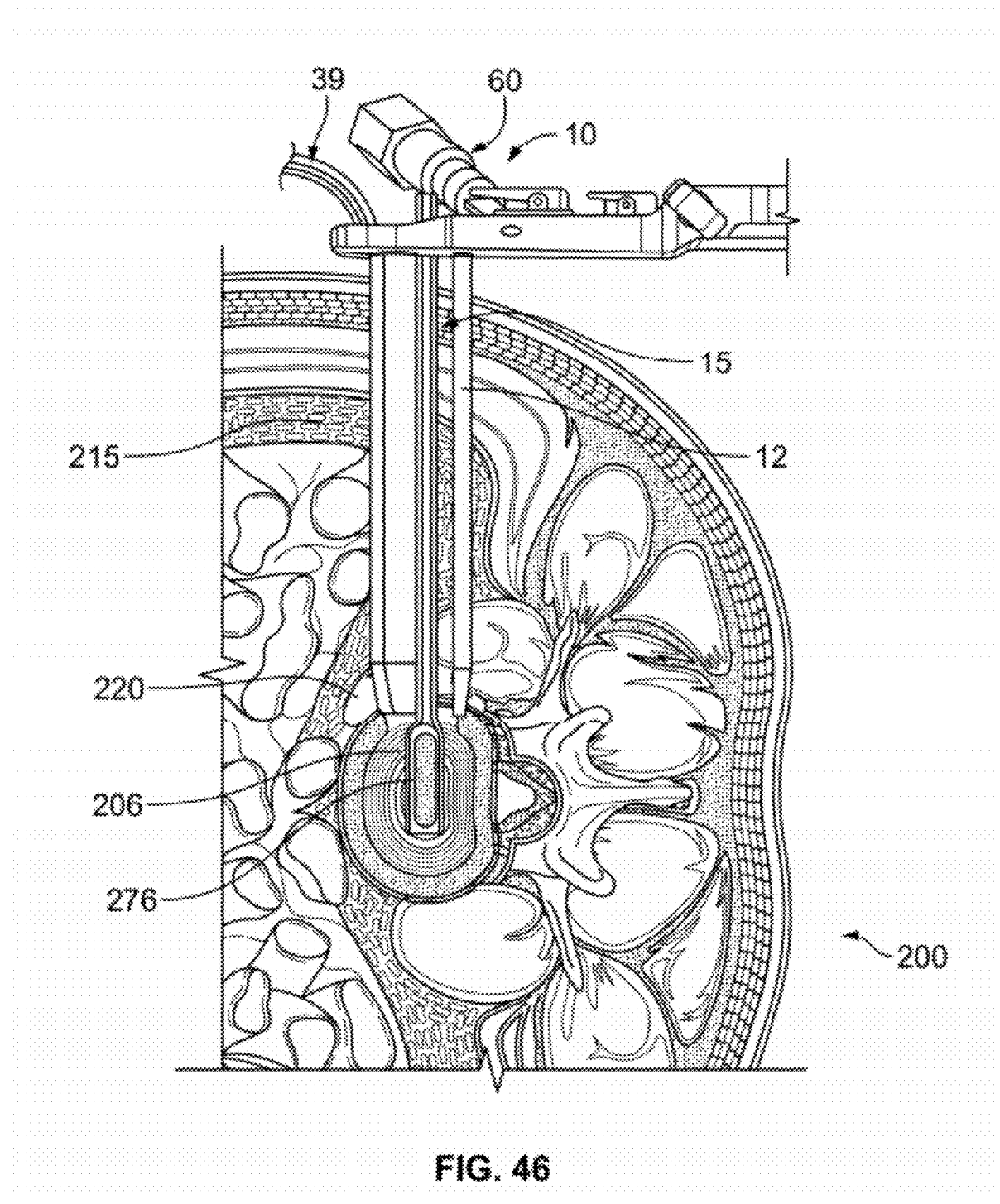
Figure 47:
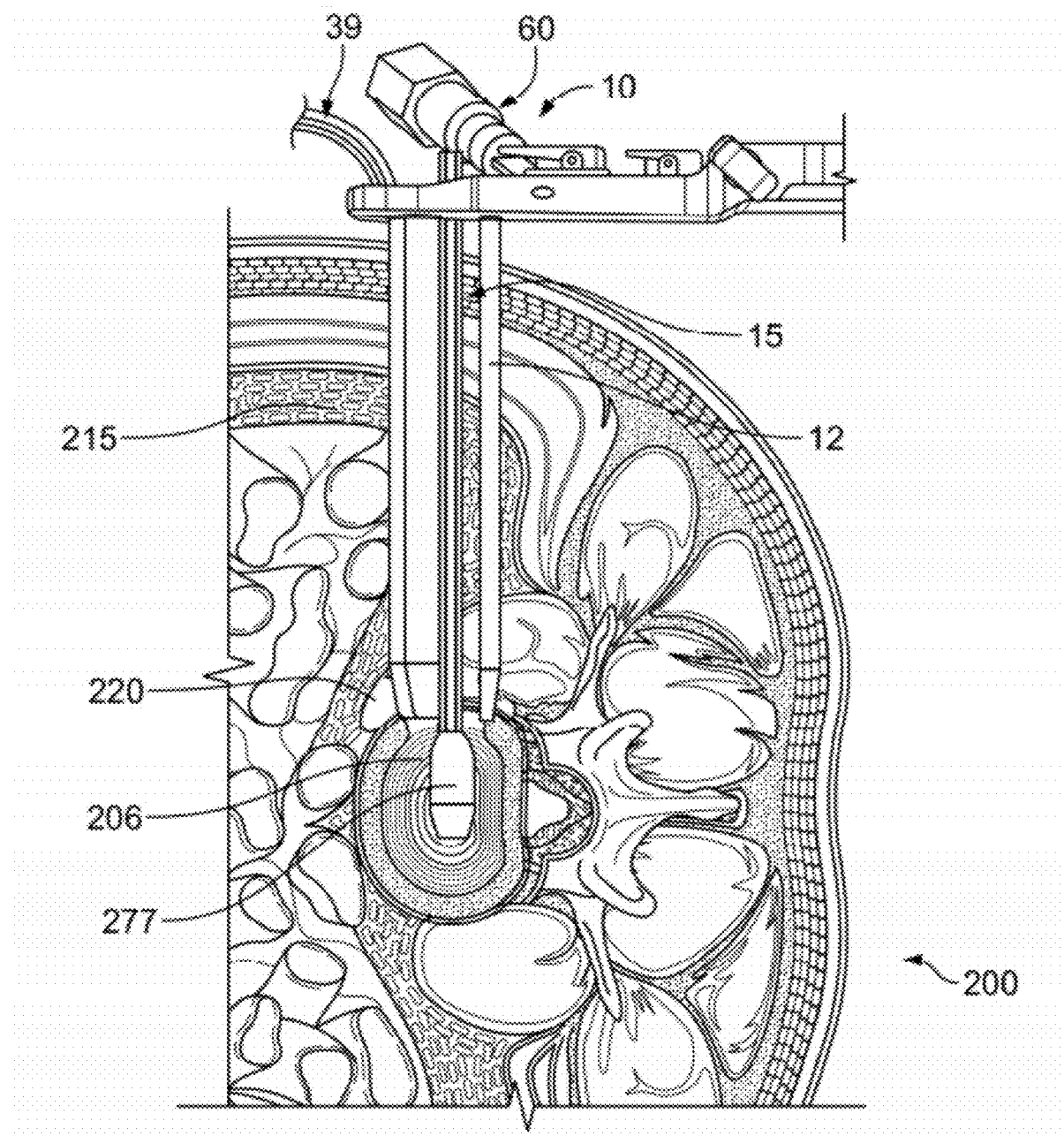
Figure 48:
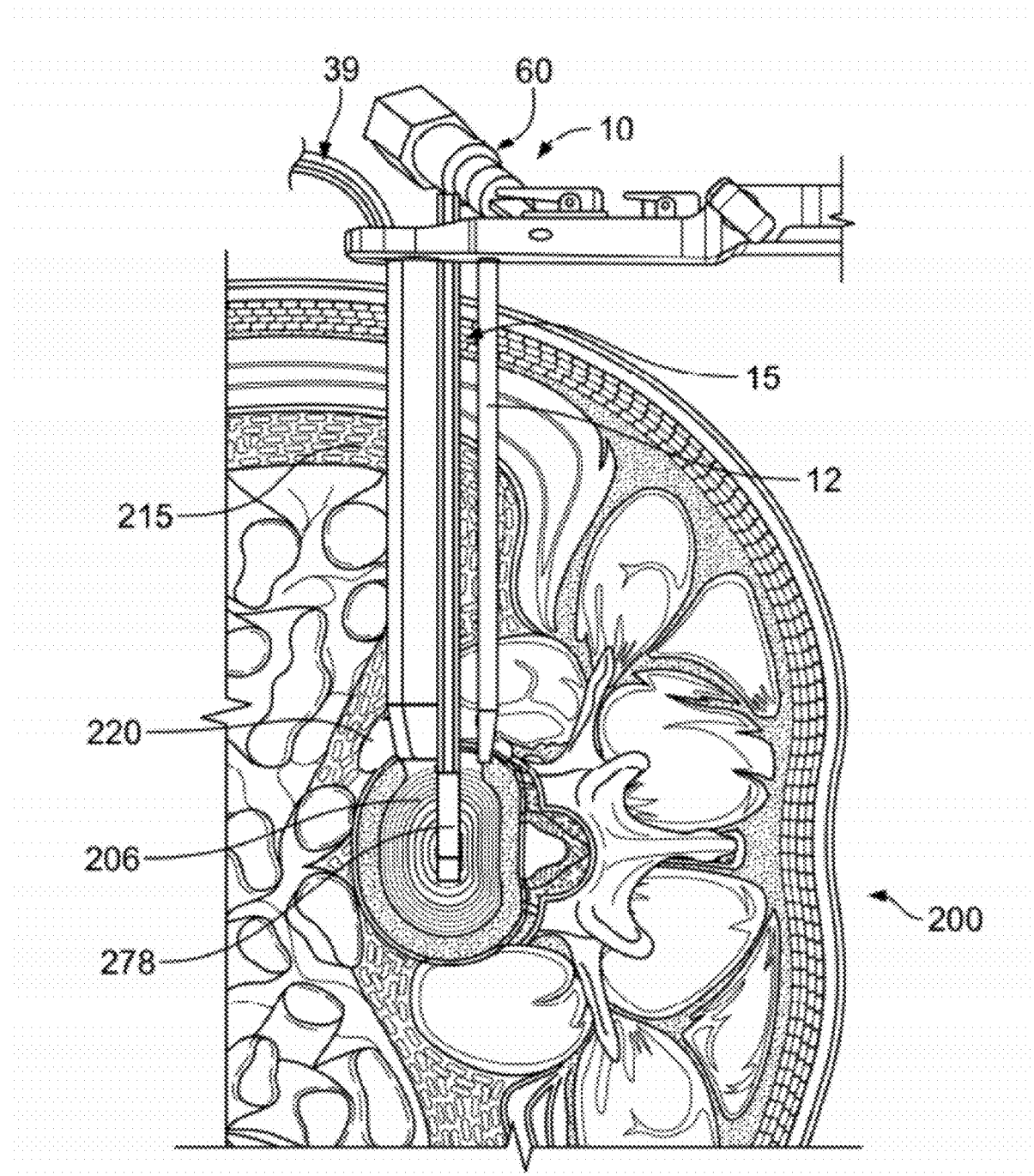

In this embodiment depicted in FIGS. 46-50, the disc space 206 is undergoing a discectomy and insertion of a spinal implant. As shown in FIG. 46, at least one preparation tool 276 such as a disc cutter, pituitary, scraper, curette, or the like is inserted through the operative corridor 15 to prepare the disc space 206. Referring more closely to FIG. 47, one or more sizers 277 are inserted to the disc space 206 to provide appropriate disc height restoration. As shown in FIG. 48, a broach 278 may be used in the disc space 206 to remove osteophytes and to facilitate implant insertion.

Figure 49:
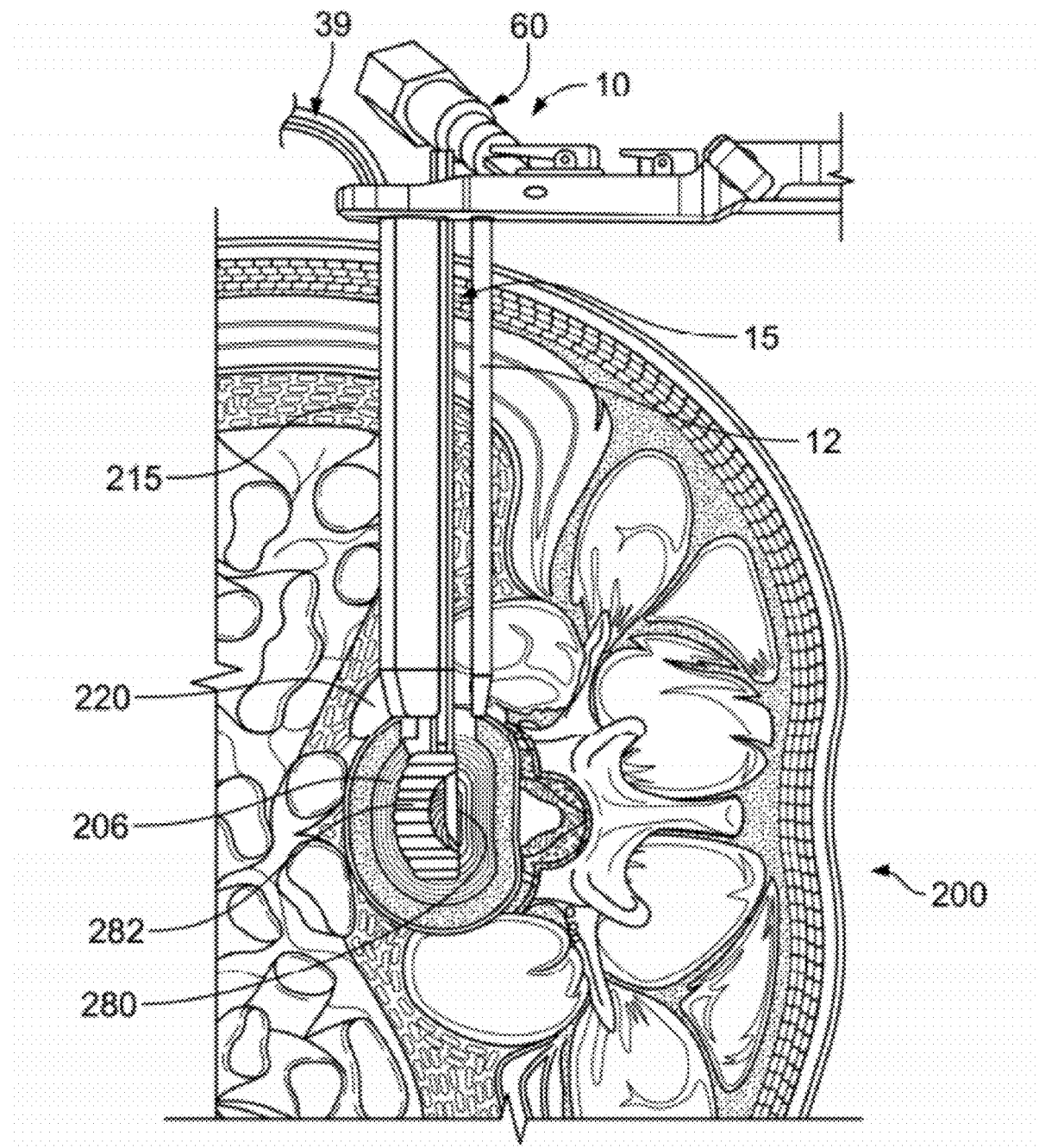
Figure 50:
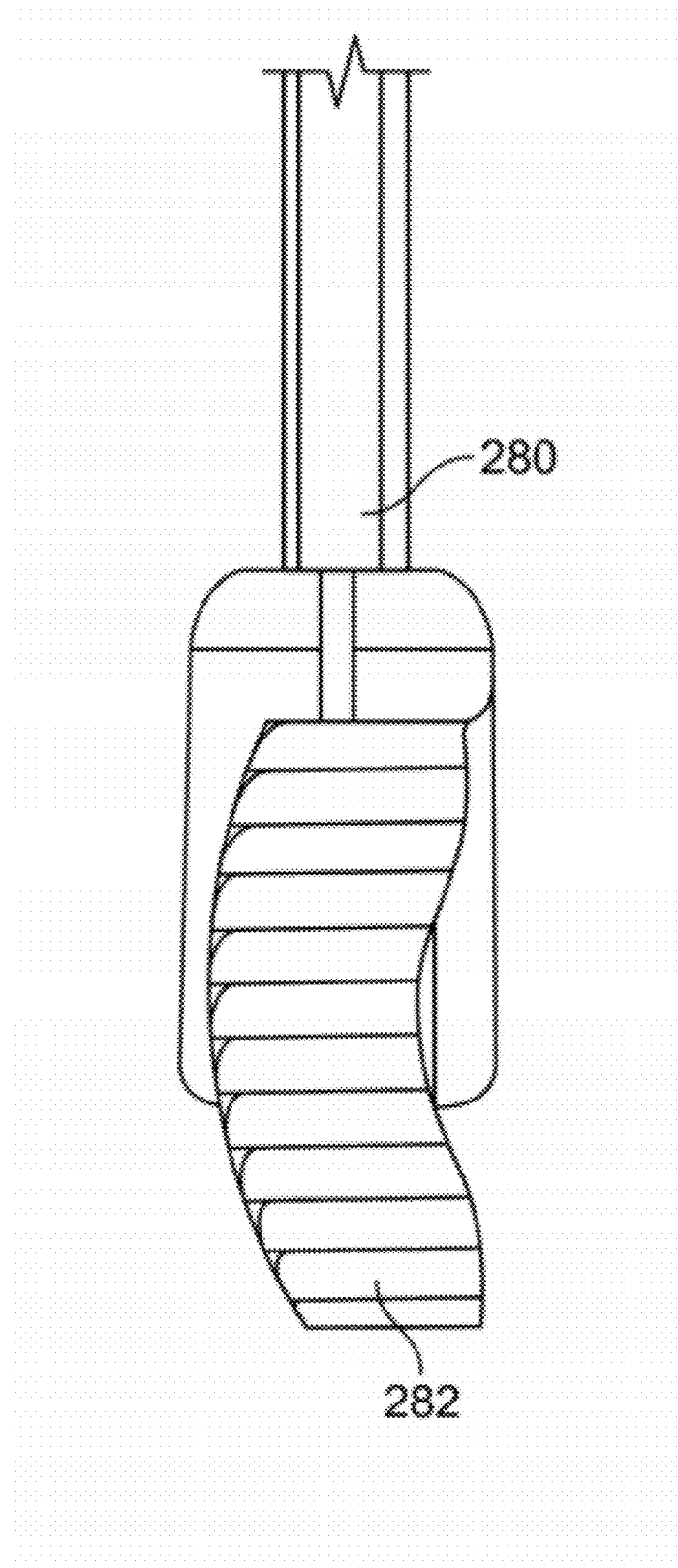

Referring now to FIGS. 49-50, an appropriately sized implant 282 is advanced into the disc space 206 with an inserter tool 280. The implant 282 is releasably secured to the inserter tool 280 such that the surgeon may release the implant when it is properly positioned in the disc space 206. The implant may comprise a material that facilitates bone fusion (such as allograft or autograft), and autograft or graft extenders may be used in the disc space 206 after the implant is inserted.

After the procedure on the targeted disc space 206 is complete, the access system 10 is carefully removed from the operative corridor 15. Direct visualization may be used to confirm the absence of significant bleeding in the disc space 206 or the psoas muscle 220. The skin around the operative corridor may be closed using a suturing method, such as a subcuticular suture.

Accordingly, certain methods of using the access system 10 can safely and effectively establish a minimally invasive operative corridor through the retroperitoneal space 215 and the psoas muscle 220 via a direct lateral, retroperitoneal approach to the spine. Such a method allows the surgeon to directly visualize the patient's anatomy without the cumbersome requirements associated with using endoscopes or operating coaxial through narrow, artificial tube. Moreover, when employing such a method to laterally approach the spine, the potential of damaging nerves while advancing dilators and other instruments through the psoas muscle 220 may be substantially reduced.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc. . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

What is claimed is:

1. A method of forming and using an operative corridor through a retroperitoneal space and a psoas muscle during a substantially lateral, retroperitoneal approach to a lumbar spine, the method comprising:
    while a user's finger is inserted through a skin incision, moving a tip portion of the user's finger through bodily tissue that is generally lateral from a lumbar spine for blunt finger dissection of the bodily tissue proximate to a retroperitoneal space;
    advancing the tip portion of the user's finger into the retroperitoneal space so as to palpate to a psoas muscle;
    advancing an elongate stimulation instrument along a lateral, trans-psoas path through the retroperitoneal space, through the psoas muscle, and to the lumbar spine such that a distal tip portion of the elongate stimulation instrument engages an annulus of a spinal disc of the lumbar spine, the distal tip portion of the elongate stimulation instrument including a stimulation electrode that outputs electrical stimulation for nerve monitoring during advancement of the elongate stimulation instrument through the psoas muscle;
    advancing a dilator system along the lateral, trans-psoas path to the lumbar spine to create a distraction corridor, the dilator system comprising at least one dilator that slidably engages an exterior of the elongate stimulation instrument, the at least one dilator being advanced to the spinal disc along the lateral, trans-psoas path to the lumbar spine;
    slidably advancing a three-bladed retractor assembly over the dilator system toward the spinal disc along the lateral, trans-psoas path, the three-bladed retractor assembly including a posterior-most retractor blade, a caudal-most retractor blade, and a cephalad-most retractor blade that extend generally perpendicularly relative to arm members of a blade holder apparatus, wherein the three-bladed retractor assembly is slidably advanced over the dilator system when in a first position in which the posterior-most retractor blade, the caudal-most retractor blade, and the cephalad-most retractor blade are positioned to simultaneously advance over the dilator system;
    adjusting the blade holder apparatus to shift the three-bladed retractor assembly to a second position in which the caudal-most retractor blade and the cephalad-most retractor blade are spaced apart from the posterior-most retractor blade to enlarge the distraction corridor and form an operative corridor along the lateral, trans-psoas path to the lumbar spine;
    inserting an implant that is releasably secured to an inserter tool through the operative corridor formed by the three-bladed retractor assembly along the lateral, trans-psoas path to the lumbar spine;
    releasing the implant from the inserter tool when the implant is positioned in a disc space of the lumbar spine.

2. The method of claim 1, wherein the step of adjusting the blade holder apparatus comprises squeezing handle portions of the blade holder apparatus toward one another so that the caudal-most retractor blade and the cephalad-most retractor blade move away from the posterior-most refractor blade.

3. The method of claim 2, further comprising releasably engaging a posterior shim element with the posterior-most retractor blade so that at least a portion of the posterior shim element extends distally from the posterior-most retractor blade and anchors into the spinal disc.

4. The method of claim 3, wherein the step of releasably engaging the posterior shim element is performed prior to the step of adjusting the blade holder apparatus to shift the three-bladed retractor assembly to the second position.

5. The method of claim 3, further comprising releasably engaging a first retractor blade extender with the caudal-most retractor blade so that at least a portion of the first retractor blade extender protrudes from the caudal-most retractor blade, and releasably engaging a second retractor blade extender with the cephalad-most refractor blade so that at least a portion of the second retractor blade extender protrudes from the cephalad-most retractor blade.

6. The method of claim 5, wherein the first and second retractor blade extenders inhibit ingress of tissue into the operative corridor after the three-bladed retractor assembly is adjusted to the second position.

7. The method of claim 1, wherein the step of moving the tip portion of the user's finger through the bodily tissue separates fatty tissue before the elongate stimulation instrument is advanced into the retroperitoneal space.

8. The method of claim 1, further comprising activating a plurality of light emitting devices to direct light through the operative corridor toward the spinal disc, the plurality of light emitting devices including a first light emitting device coupled to the cephalad-most retractor blade and a second light emitting device coupled to the caudal-most retractor blade.

9. The method of claim 8, further comprising inserting at least one preparation tool through the operative corridor formed by the three-bladed retractor assembly along the lateral, trans-psoas path to the lumbar spine so as to remove a portion of the spinal disc from the disc space.

10. The method of claim 9, further comprising inserting a sizer instrument into the disc space of the lumbar spine before the implant is inserted into the disc space.

11. The method of claim 1, wherein the step of adjusting the blade holder apparatus comprises: pivoting two of the arm members of the blade holder apparatus so as to move the caudal-most retractor blade and the cephalad-most retractor blade away from the posterior-most retractor blade, and rotating a knob element on the blade holder apparatus so as to linearly move the posterior-most retractor blade relative to the caudal-most retractor blade and the cephalad-most retractor blade.

12. The method of claim 11, wherein the two arm members of the blade holder apparatus are pivoted in response to squeezing proximal gripper portions of the blade holder apparatus so that the caudal-most retractor blade and the cephalad-most retractor blade are simultaneously moved away from one another.

13. The method of claim 12, wherein the caudal-most retractor blade and the cephalad-most retractor blade are simultaneously moved away from one another while the posterior-most retractor blade is maintained in generally fixed position relative to the lumbar spine.

14. The method of claim 1, wherein the step of advancing the elongate stimulation instrument comprises delivering the elongate stimulation instrument together with the at least one dilator cannula along the lateral, trans-psoas path to the lumbar spine.

15. The method of claim 1, wherein when the three-bladed retractor assembly is in the first position, the posterior-most retractor blade, the caudal-most retractor blade, and the cephalad-most retractor blade are positioned generally adjacent to one another.

16. The method of claim 15, wherein when the three-bladed retractor assembly is in the first position, the posterior-most refractor blade, the caudal-most retractor blade, and the cephalad-most retractor blade are in generally abutting relation with one another.

17. The method of claim 1, wherein the step of advancing the dilator system comprises sequentially advancing a plurality of supplemental dilators along the lateral, trans-psoas path to the lumbar spine.

18. The method of claim 1, wherein the elongate stimulation instrument comprises a K-wire.

19. The method of claim 1, further comprising:
activating a nerve monitoring system that delivers an electrical stimulation signal to the stimulation electrode of the elongate member during delivery of the elongate member along the lateral, trans-psoas path to the lumbar spine, the nerve monitoring system detecting electromyographic activity via a set of sensor electrodes in leg muscle myotomes associated with nerves in the vicinity of the spinal disc; and
viewing a video display device of the nerve monitoring system that contemporaneously displays: a numeric stimulation threshold required to obtain the electromyographic activity in at least one of said leg muscle myotomes, and myotomes levels being monitored.

20. The method of claim 1, wherein the skin incision through which the user's finger is inserted is different from a skin penetration point of the elongate stimulation instrument.

21. A method of forming and using an operative corridor through a retroperitoneal space and a psoas muscle during a substantially lateral, retroperitoneal approach to a lumbar spine, the method comprising:
while a user's finger is inserted through a skin incision, moving a tip portion of the user's finger through bodily tissue in a retroperitoneal space that is generally lateral from a lumbar spine and advancing the tip portion of the user's finger to palpate to a psoas muscle that is generally lateral from a lumbar spine;
advancing a dilator system along the lateral, trans-psoas path to the lumbar spine to create a distraction corridor, the dilator system comprising: an initial dilator that is advanced through the psoas muscle to a spinal disc of the lumbar spine, a first supplemental dilator that slidably advances along the lateral, trans-psoas path over an exterior of the initial dilator, and a second supplemental dilator that slidably advances along the lateral, trans-psoas path over an exterior of the first supplemental dilator, wherein at least the initial dilator includes a stimulation electrode that outputs electrical stimulation for nerve monitoring when the initial dilator is positioned in the psoas muscle;
slidably advancing a three-bladed retractor assembly over an exterior of an outermost dilator of the dilator system toward the spinal disc along the lateral, trans-psoas path, the three-bladed retractor assembly including a posterior-most retractor blade, a caudal-most retractor blade, and a cephalad-most retractor blade that extend from a blade-holder apparatus, wherein the three-bladed retractor assembly is slidably advanced over the dilator system when in a first position in which the posterior-most retractor blade, the caudal-most retractor blade, and the cephalad-most retractor blade are positioned to simultaneously advance over the outermost dilator of the dilator system;
adjusting the blade-holder apparatus of the three-bladed retractor assembly so as to shift the three-bladed retractor assembly to a second position in which the caudal-most retractor blade and the cephalad-most retractor blade are spaced away from the posterior-most retractor blade to enlarge the distraction corridor and form an operative corridor along the lateral, trans-psoas path to the lumbar spine;
inserting an implant that is releasably secured to an inserter tool through the operative corridor formed by the three-bladed retractor assembly along the lateral, trans-psoas path to the lumbar spine; and
releasing the implant from the inserter tool when the implant is positioned in a disc space of the lumbar spine.

22. The method of claim 21, wherein an inner wire member is received within a central lumen of the initial dilator and penetrates laterally into an annulus of the spinal disc of the lumbar spine prior to advancing the first and second supplemental dilators.

23. The method of claim 21, further comprising adjusting a position of a first retractor blade extender removably attached to the caudal-most retractor blade so that at least a portion of the first retractor blade extender protrudes from the caudal-most retractor blade, and adjusting a position of a second retractor blade extender removably attached to the cephalad-most retractor blade so that at least a portion of the second retractor blade extender protrudes from the cephalad-most retractor blade.

24. The method of claim 23, wherein the first and second retractor blade extenders inhibit ingress of tissue into the operative corridor after the three-bladed retractor assembly is adjusted to the opened position.

25. The method of claim 21, wherein the step of moving the tip portion of the user's finger through the bodily tissue separates fatty tissue in the retroperitoneal space before the initial dilator is advanced into the retroperitoneal space.

26. The method of claim 21, further comprising activating a light emitting device to direct light through the operative corridor toward the spinal disc, the light emitting device being coupled to one of the cephalad-most retractor blade and the caudal-most retractor blade.

27. The method of claim 21, further comprising inserting at least one preparation tool through the operative corridor formed by the three-bladed retractor assembly along the lateral, trans-psoas path to the lumbar spine so as to remove a portion of the spinal disc from the disc space.

28. The method of claim 27, further comprising inserting a sizer instrument into the disc space of the lumbar spine before the implant is inserted into the disc space.

29. The method of claim 21, wherein the step of adjusting the blade-holder apparatus comprises rotating a knob element of the blade-holder apparatus relative to a linear rack member of the blade-holder apparatus.

30. The method of claim 21, wherein the blade-holder apparatus comprises two arm portions, wherein the step of adjusting the blade-holder apparatus comprises pivoting the two arm portions.

31. The method of claim 21, wherein the initial dilator is advanced to the spinal disc together with an inner wire member received within a central lumen of the initial dilator.

32. The method of claim 21, wherein when the three-bladed retractor assembly is adjusted to the second position, the posterior-most retractor blade, the caudal-most retractor blade, and the cephalad-most retractor blade are spaced apart and maintained generally parallel to one another.

33. The method of claim 21, wherein when the three-bladed retractor assembly is in the first position, the posterior-most retractor blade, the caudal-most retractor blade, and the cephalad-most retractor blade are in generally abutting relation with one another.

34. The method of claim 21, further comprising:
activating a nerve monitoring system that delivers an electrical stimulation signal to the stimulation electrode of the initial dilator during advancement of the initial dilator through the psoas muscle, the nerve monitoring system detecting electromyographic activity via a set of sensor electrodes in leg muscle myotomes associated with nerves in the vicinity of the spinal disc; and
viewing a video display device of the nerve monitoring system that displays information in response to the electromyographic activity in at least one of said leg muscle myotomes.

35. The method of claim 21, wherein the skin incision through which the user's finger is inserted is different from a skin penetration point of the initial dilator.

36. The method of claim 21, wherein the first and second supplemental dilators include stimulation electrodes that output electrical stimulation for nerve monitoring.

* * * * *

UNITED STATES PATENT AND TRADEMARK OFFICE
CERTIFICATE OF CORRECTION

PATENT NO. : 8,303,515 B2  Page 1 of 1
APPLICATION NO. : 12/635869
DATED : November 6, 2012
INVENTOR(S) : Patrick Miles It is certified that error appears in the above-identified patent and that said Letters Patent is hereby corrected as shown below:

Column 18, Line 18 (Claim 2), delete "refractor" and insert -- retractor --, therefor.

Column 18, Line 33 (Claim 5), delete "refractor" and insert -- retractor --, therefor.

Column 19, Line 24 (Claim 16), delete "refractor" and insert -- retractor --, therefor.

Signed and Sealed this
Twenty-ninth Day of January, 2013

David J. Kappos
*Director of the United States Patent and Trademark Office*